United States Patent
Jonas et al.

(10) Patent No.: US 8,067,641 B2
(45) Date of Patent: Nov. 29, 2011

(54) SYNTHESIS OF TRIETHYLENETETRAMINES

(75) Inventors: Marco Jonas, Neuenhof (CH); Irene Vaulont, Buchs (CH); Antonio Soi, Buchs AG (CH); Gunther Schmidt, Aarau (CH)

(73) Assignee: Philera New Zealand Limited, Auckland (NZ)

( * ) Notice: Subject to any disclaimer, the term of this patent is extended or adjusted under 35 U.S.C. 154(b) by 0 days.

(21) Appl. No.: 12/460,616

(22) Filed: Jul. 21, 2009

(65) Prior Publication Data

US 2010/0173994 A1 Jul. 8, 2010

Related U.S. Application Data

(62) Division of application No. 11/184,761, filed on Jul. 19, 2005, now Pat. No. 7,582,796.

(60) Provisional application No. 60/589,080, filed on Jul. 19, 2004.

(51) Int. Cl.
*C07C 211/13* (2006.01)

(52) U.S. Cl. ...................................................... 564/512

(58) Field of Classification Search .................. None
See application file for complete search history.

(56) References Cited

OTHER PUBLICATIONS

Database CAPLUS on STN, Acc. No. 1980:495005, Witek, PL 105793 B1 (Oct. 31, 1979) (abstract).*
Database CAPLU on STN, Acc. No. 1991:234954, Fujito et al., Yakuzaigaku (1990), 50(4), p. 402-408 (abstract).*

* cited by examiner

*Primary Examiner* — Brian J Davis
(74) *Attorney, Agent, or Firm* — McDonnell Boehnen Hulbert & Berghoff LLP

(57) ABSTRACT

Methods and intermediates for synthesizing triethylenetetramine and salts thereof, as well as novel triethylenetetramine salts and their crystal structure, and triethylenetetramine salts of high purity.

25 Claims, 22 Drawing Sheets

I

II

III

SYNTHESIS OF TRIETHYLENETETRAMINES

RELATED APPLICATION

This application is a divisional of U.S. Ser. No. 11/184,761, filed Jul. 19, 2005, now U.S. Pat. No. 7,582,796, which claims the benefit of priority to U.S. Provisional Application No. 60/589,080, filed Jul. 19, 2004, the contents of which is hereby incorporated by reference in its entirety.

FIELD OF THE INVENTION

The field relates to chemicals and methods of chemical synthesis including, for example, novel methods for synthesis of triethylenetetramines and triethylenetetramine salts, and crystals and polymorphs thereof, as well as intermediates for, or within, said synthesis methods. The compounds have utility in a variety of therapeutic areas.

BACKGROUND OF THE INVENTION

The following includes information that may be useful in understanding the present inventions. It is not an admission that any of the information provided herein is prior art, or relevant, to the presently described or claimed inventions, or that any publication or document that is specifically or implicitly referenced is prior art.

Polyethylenepolyamines include triethylenetetramines that act as copper antagonists. Triethylenetetramine, sometimes also referred to as trientine, N,N'-Bis(2-aminoethyl)-1, 2-ethanediamine, 1,8-diamino-3,6-diazaoctane, 3,6-diazaoctane-1,8-diamine, 1,4,7,10-tetraazadecane, trien, TETA, TECZA, N,N'-Bis(aminoethyl)ethylenediamine, N,N'-Bis (2-aminoethyl)ethanediamine, and N,N'-Bis(2-aminoethyl)-ethylenediamine, is a copper chelating agent. Triethylenetetramine is used as an epoxy curing agent. *Merck Index*, p. 9478 (10th Edition, 1983). It has also been used as a thermosetting resin, as a lubricating oil additive, and as an analytical reagent for copper and nickel id. Triethylenetetramine dihydrochloride has also been used for treating individuals with Wilson's disease. See, for example, id.; Dubois, R. S., *Lancet* 2(7676): 775 (1970); Walshe, J. M., *Q. J. Med.* 42(167):441-52 (1973); Haslam, R. H., et al., *Dev. Pharmacol. Ther.* 1(5):318-24 (1980). It has also reportedly been used to treat individuals with primary biliary cirrhosis. See, for example, Epstein, O., et al., *Gastroenterology* 78(6):1442-45 (1980). In addition, trientine has been tested for inhibition of the spontaneous development of hepatitis and hepatic tumors in rats. See, for example, Sone, H., et al., *Hepatology* 23:764-70 (1996). U.S. Pat. Nos. 6,897,243, 6,610,693 and 6,348,465 describe the use of copper binding compounds in the treatment of various disorders, including treatment of diabetes mellitus and complications thereof, including, for example, diabetic cardiomyopathy.

Trientine was said to be used in the synthesis of benzylidene-(2-{3-[2-(benzylidene-amino)-ethyl]-2-phenyl-imidazolidin-1-yl}-ethyl)-amine in French Patent No. FR2810035 to Guilard et al. Cetinkaya, E., et al., "Synthesis and characterization of unusual tetraminoalkenes," *J. Chem. Soc.* 5:561-7 (1992), is said to be directed to synthesis of benzylidene-(2-{3-[2-(benzylidene-amino)-ethyl]-2-phenyl-imidazolidin-1-yl}-ethyl)-amine from trientine, as is Araki T., et al., "Site-selective derivatization of oligoethyleneimines using five-membered-ring protection method," *Macromol.*, 21:1995-2001 (1988). Triethylenetetramine may reportedly also be used in the synthesis of N-methylated triethylenetetramine, as reported in U.S. Pat. No. 2,390,766, to Zellhoefer et al.

Synthesis of polyethylenepolyamines, including triethylenetetramines, from ethylenediamine and monoethanolamine using pelleted group IVb metal oxide-phosphate type catalysts was reported by Vanderpool et al. in U.S. Pat. No. 4,806,517. Synthesis of triethylenetetramine from ethylenediamine and ethanolamine was also proposed in U.S. Pat. No. 4,550,209, to Unvert et al. U.S. Pat. No. 5,225,599, to King et al. is said to be directed to the synthesis of linear triethylene tetramine by condensation of ethylenediamine and ethylene glycol in the presence of a catalyst. Joint production of triethylenetetramine and 1-(2-aminoethyl)-aminoethyl-piperazine was proposed by Borisenko et al. in U.S.S.R. Patent No. SU1541204. U.S. Pat. No. 4,766,247 and European Patent No. EP262562, both to Ford et al., reported the preparation of triethylenetetramine by reaction of an alkanolamine compound, an alkaline amine and optionally either a primary or secondary amine in the presence of a phosphorous containing catalyst, for example phosphoric acid on silica-alumina or Group IIIB metal acid phosphate, at a temperature from about 175° C. to 400° C. under pressure. These patents indicate that the synthetic method used therein was as set forth in U.S. Pat. No. 4,463,193, to Johnson. The Ford et al. '247 patent is also said to be directed to color reduction of polyamines by reaction at elevated temperature and pressure in the presence of a hydrogenation catalyst and a hydrogen atmosphere. European Patent No. EP450709 to King et al. is said to be directed to a process for the preparation of triethylenetetramine and N-(2-aminoethyl)ethanolamine by condensation of an alkylenamine and an alkylene glycol in the presence of a condensation catalyst and a catalyst promoter at a temperature in excess of 260° C.

Russian Patent No. RU2186761, to Zagidullin, proposed synthesis of diethylenetriamine by reaction of dichloroethane with ethylenediamine. Ethylenediamine has previously been said to have been used in the synthesis of N-carboxylic acid esters as reported in U.S. Pat. No. 1,527,868, to Hartmann et al.

Japanese Patent No. 06065161 to Hara et al. is said to be directed to the synthesis of polyethylenepolyamines by reacting ethylenediamine with ethanolamine in the presence of silica-treated Nb205 supported on a carrier. Japanese Patent No. JP03047154 to Watanabe et al., is said to be directed to production of noncyclic polyethylenepolyamines by reaction of ammonia with monoethanolamine and ethylenediamine. Production of non-cyclic polyethylenepolyamines by reaction of ethylenediamine and monoethanolamine in the presence of hydrogen or a phosphorous-containing substance was said to be reported in Japanese Patent No. JP03048644. Regenerative preparation of linear polyethylenepolyamines using a phosphorous-bonded catalyst was proposed in European Patent No. EP115,138, to Larkin et al.

A process for preparation of alkyleneamines in the presence of a niobium catalyst was said to be provided in European Patent No. 256,516, to Tsutsumi et al. U.S. Pat. No. 4,584,405, to Vanderpool, reported the continuous synthesis of essentially noncyclic polyethylenepolyamines by reaction of monoethanolamine with ethylenediamine in the presence of an activated carbon catalyst under a pressure between about 500 to about 3000 psig., and at a temperature of between about 200° C. to about 400° C. Templeton, et al., reported on the preparation of linear polyethylenepolyamides asserted to result from reactions employing silica-alumina catalysts in European Patent No. EP150,558.

Production of triethylenetetramine dihydrochloride was said to have been reported in Kuhr et al., Czech Patent No. 197,093, via conversion of triethylenetetramine to crystalline tetrahydrochloride and subsequently to triethylenetetramine dihydrochloride. "A study of efficient preparation of triethylenetetramine dihydrochloride for the treatment of Wilson's disease and hygroscopicity of its capsule," Fujito, et al., *Yakuzaigaku*, 50:402-8 (1990), is also said to be directed to production of triethylenetetramine.

Preparation of triethylenetetramine salts used for the treatment of Wilson's disease was said to be reported in "Treatment of Wilson's Disease with Triethylene Tetramine Hydrochloride (Trientine)," Dubois, et al., *J. Pediatric Gastro. & Nutrition*, 10:77-81 (1990); "Preparation of Triethylenetetramine Dihydrochloride for the Treatment of Wilson's Disease," Dixon, et al., Lancet, 1(1775):853 (1972); "Determination of Triethylenetetramine in Plasma of Patients by High-Performance Liquid Chromatography," Miyazaki, et al., *Chem. Pharm. Bull.*, 38(4):1035-1038 (1990); "Preparation of and Clinical Experiences with Trien for the Treatment of Wilson's Disease in Absolute Intolerance of D-penicillamine," Harders, et al., *Proc. Roy. Soc. Med.*, 70:10-12 (1977); "Tetramine cupruretic agents: A comparison in dogs," Allen, et al., *Am. J. Vet. Res.*, 48(1):28-30 (1987); and "Potentiometric and Spectroscopic Study of the Equilibria in the Aqueous Copper(II)-3,6-Diazaoctane-1,8-diamine System," Laurie, et al., *J. C. S. Dalton*, 1882 (1976).

Preparation of Triethylenetetramine Salts by Reaction of Alcohol Solutions of amines and acids was said to be reported in Polish Patent No. 105793, to Witek. Preparation of triethylenetetramine salts was also asserted in "Polycondensation of polyethylene polyamines with aliphatic dicarboxylic acids," Witek, et al., *Polimery*, 20(3):118-119 (1975).

Baganz, H., and Peissker, H., *Chem. Ber.*, 1957; 90:2944-2949; Haydock, D. B., and Mulholland, T. P. C., *J. Chem. Soc.*, 1971; 2389-2395; and Rehse, K., et al., *Arch. Pharm.*, 1994; 393-398, report on Strecker syntheses. Use of Boc and other protecting groups has been described. See, for example, Spicer, J. A. et al., *Bioorganic & Medicinal Chemistry*, 2002; 10: 19-29; Klenke, B. and Gilbert, I. H., *J. Org. Chem.*, 2001; 66: 2480-2483.

Existing methods of synthesis of triethylenetetramines, and polyethylenepolyamines, are unsatisfactory. For instance, they often require high temperature and pressure. A method for production of more pure triethylenetetramines at high yield under more favorable conditions including, for example, at more manageable temperatures and pressures, would be desirable. Such methods have been invented and are described and claimed herein.

BRIEF DESCRIPTION OF THE INVENTION

The inventions described and claimed herein have many attributes and encompass many embodiments including, but not limited to, those set forth in this Summary. The inventions described and claimed herein are not limited to or by the features or embodiments identified in this Summary, which is included for purposes of illustration only and not restriction.

Methods for synthesis of triethylenetetramines are provided. Triethylenetetramines, and triethylenetetramine salts and polymorphs and crystals thereof in high yields and purity are obtained.

In one embodiment at least one intermediate is synthesized that may be crystallized. Intermediates which may, but need not be, crystallized include protected dinitrile intermediates. Crystallized dinitrile intermediates may be used in the synthesis of a triethylenetetramine.

In one embodiment, synthesis of a triethylenetetramine salt includes synthesis of a dinitrile from ethylenediamine and other starting materials, including, for instance, by alkylation by haloacetonitrile (for example, chloroacetonitrile or bromoacetonitrile). A Strecker synthesis using formaldehyde and a cyanide salt may also be used to form a dinitrile from ethylenediamine. The resulting dinitrile is derivatized (optionally in situ) with a protecting group or groups, for example, benzaldehyde to form a benzaldehyde-protected dinitrile or $Boc_2O$ (di-tert-butyl dicarbonate) to form a Boc-protected dinitrile. The resulting protected dinitrile is optionally purified by crystallization or another method. The protected dinitrile is reduced to form a protected diamine, and the protected diamine is deprotected by hydrolysis with an acid to form a triethylenetetramine salt, including a triethylenetetramine primary salt, a triethylenetetramine secondary salt, a triethylenetetramine tertiary salt and/or a triethylenetetramine quaternary salt. Optionally, further reaction of a triethylenetetramine tertiary salt or a triethylenetetramine quaternary salt with a base in a solvent, followed by reaction with a concentrated acid, may be used to form a triethylenetetramine secondary salt.

In another embodiment, synthesis of a triethylenetetramine salt includes synthesis of a dinitrile from ethylenediamine and other starting materials, including, for instance, by alkylation by haloacetonitrile (for example, chloroacetonitrile or bromoacetonitrile). A Strecker synthesis using formaldehyde and a cyanide salt may also be used to form a dinitrile from ethylenediamine. The resulting dinitrile is then derivatized (optionally in situ) with a protecting group or groups, for example, benzaldehyde to form a benzaldehyde-protected dinitrile or $Boc_2O$ (di-tert-butyl dicarbonate) to form a Boc-protected dinitrile. The resulting protected dinitrile is optionally purified by crystallization or another method. The protected dinitrile is reduced to form a protected diamine. The diamine is derivatized with a protecting group or groups to form a protected derivative, for example, with benzaldehyde to form a tri-benzaldehyde protected derivative. The protected derivative is optionally purified by crystallization or another method. A further reaction includes deprotection of the protected derivative and preparation of a triethylenetetramine salt, including a triethylenetetramine primary salt, a triethylenetetramine secondary salt, a triethylenetetramine tertiary salt, and/or a triethylenetetramine quaternary salt. Optionally, further reaction of a triethylenetetramine tertiary salt or a triethylenetetramine quaternary salt with a base in a solvent, followed by reaction with a concentrated acid, may be used to form a triethylenetetramine secondary salt.

In another embodiment the protected diamine undergoes a quenching step to remove remaining reduction materials.

In still another embodiment a triethylenetetramine salt is prepared by the addition of an acid, which optionally, has been dissolved in a solvent prior to its addition to the protected diamine. The subsequent crystals formed are then re-crystallized in solution.

The invention also provides preparation of a purified triethylenetetramine salt by derivatization of an impure triethylenetetramine with a protecting group or protecting groups to form a protected derivative. For instance, an impure triethylenetetramine may be derivatized with benzaldehyde, forming a tribenzaldehyde protected derivative. The protected derivative is purified by crystallization or another method. A further reaction includes deprotection of the protected derivative and preparation of a triethylenetetramine salt, including a triethylenetetramine primary salt, a triethylenetetramine secondary salt, a triethylenetetramine tertiary salt or a triethylenetetramine quaternary salt. Optionally, further reaction of a quaternary or tertiary triethylenetetramine salt with a base in a solvent, followed by reaction with a concentrated acid, may be used to form a triethylenetetramine secondary salt.

Also provided are polymorphs of triethylenetetramine salts and methods for their preparation. These polymorphs include polymorphs of triethylenetetramine disuccinate, triethylenetetramine tetrahydrochloride, and triethylenetetramine dihydrochloride.

In one embodiment a triethylenetetramine disuccinate polymorph has a differential scanning calorimetry (DSC) extrapolated onset/peak melting temperature of from between about 170° C. to about 190° C.

In one embodiment a Form I polymorph of triethylenetetramine dihydrochloride has a DSC extrapolated onset/peak melting temperature of from between about 111° C. to about 132° C.

In one embodiment a Form II polymorph of triethylenetetramine dihydrochloride is characterized by a DSC extrapolated onset/peak melting temperature of from between about 170° C. to about 190° C.

In certain embodiments, crystalline triethylenetetramine and salts thereof are provided. These include crystalline triethylenetetramine maleate (e.g., triethylenetetramine tetramaleate and triethylenetetramine tetramaleate dihydrate), triethylenetetramine fumarate (e.g., triethylenetetramine tetrafumarate and triethylenetetramine tetrafumarate tetrahydrate), and triethylenetetramine succinate (e.g, triethylenetetramine disuccinate anhydrate). Different triethylenetetramine crystals include those comprising the geometric structures, unit cell structures, and structural coordinates set forth herein.

In certain embodiments, substantially pure triethylenetetramine disuccinate is provided. A pharmaceutical composition comprising substantially pure triethylenetetramine disuccinate is also provided.

In certain embodiments, substantially pure triethylenetetramine disuccinate dihydrate is provided. In other embodiments, a pharmaceutical composition comprising substantially pure triethylenetetramine disuccinate anhydrate is also provided.

In other embodiments, substantially pure triethylenetetramine disuccinate tetrahydrate is provided. In certain embodiments, a pharmaceutical composition comprising substantially pure triethylenetetramine disuccinate tetrahydrate is also provided.

In certain embodiments, crystalline triethylenetetramine succinate in the form of a crystal having alternating layers of triethylenetetramine molecules and succinate molecules is provided. The triethylenetetramine succinate may be a triethylenetetramine disuccinate. The triethylenetetramine disuccinate may be a triethylenetetramine disuccinate anhydrate. Pharmaceutical compositions comprising crystalline triethylenetetramine succinate in the form of a crystal having alternating layers of triethylenetetramine molecules and succinate molecules are also provided, including pharmaceutical compositions having crystalline triethylenetetramine disuccinate anhydrate in the form of a crystal having alternating layers of triethylenetetramine molecules and succinate molecules.

In certain embodiments, substantially pure triethylenetetramine maleate is provided. A pharmaceutical composition comprising substantially pure triethylenetetramine maleate is also provided.

In certain embodiments, substantially pure triethylenetetramine tetramaleate is provided. In other embodiments, a pharmaceutical composition comprising substantially pure triethylenetetramine tetramaleate is provided.

In other embodiments, substantially pure triethylenetetramine tetramaleate dihydrate is provided. In certain embodiments, a pharmaceutical composition comprising substantially pure triethylenetetramine tetramaleate anhydrate is also provided.

In certain embodiments, a composition comprising crystalline triethylenetetramine maleate in the form of a crystal having alternating layers of triethylenetetramine molecules and maleate molecules is provided. The triethylenetetramine maleate may be a triethylenetetramine tetramaleate. The triethylenetetramine maleate may be a triethylenetetramine tetramaleate dihydrate. Pharmaceutical compositions comprising crystalline triethylenetetramine maleate in the form of a crystal having alternating layers of triethylenetetramine molecules and maleate molecules are also provided, including pharmaceutical compositions having crystalline triethylenetetramine tetramaleate dihydrate in the form of a crystal having alternating layers of triethylenetetramine molecules and maleate molecules.

In certain embodiments, substantially pure triethylenetetramine fumarate is provided. A pharmaceutical composition comprising substantially pure triethylenetetramine fumarate and/or a pharmaceutically acceptable excipient is also provided.

In certain embodiments, substantially pure triethylenetetramine tetrafumarate is provided. In other embodiments, a pharmaceutical composition comprising substantially pure triethylenetetramine tetrafumarate is provided.

In other embodiments, substantially pure triethylenetetramine tetrafumarate tetrahydrate is provided. In certain embodiments, a pharmaceutical composition comprising substantially pure triethylenetetramine tetrafumarate tetrahydrate is provided.

In certain embodiments, a composition comprising crystalline triethylenetetramine fumarate in the form of a crystal having alternating layers of triethylenetetramine molecules and fumarate molecules is provided. The triethylenetetramine fumarate may be a triethylenetetramine tetrafumarate. The triethylenetetramine fumarate may be a triethylenetetramine tetrafumarate tetrahydrate. Pharmaceutical compositions comprising crystalline triethylenetetramine fumarate in the form of a crystal having alternating layers of triethylenetetramine molecules and fumarate molecules are also provided, including pharmaceutical compositions having crystalline triethylenetetramine tetrafumarate tetrahydrate in the form of a crystal having alternating layers of triethylenetetramine molecules and fumarate molecules.

In certain embodiments, a crystal of a triethylenetetramine disuccinate having a C 2/c (no. 15) space group with measured unit cell dimensions of a=14.059(5) Å, b=9.169(5) Å, c=13.647(5) Å, and β=92.47(0) Å, is provided. Cell volume is 1757.56(130) Å$^3$.

In certain embodiments, A crystal of a triethylenetetramine tetramaleate having a P 1 2/c 1 (no. 13) space group with measured unit cell dimensions of a=13.261(5) Å, b=9.342 Å, c=11.266 Å, and β=91.01(0) Å, is provided. Cell volume is 1395.46(110) Å$^3$.

In certain embodiments, a crystal of a triethylenetetramine tetrafumarate having a P m n a (no. 53) space group with measured unit cell dimensions of a=13.9031(3) Å, b=7.9589(2) Å, c=14.6554(3) Å, and β=90 Å, is provided. Cell volume is 1621.67(6) Å$^3$.

In certain embodiments, a crystal of a triethylenetetramine disuccinate having the structure defined by the co-ordinates of Tables 1A-1C is provided.

In certain embodiments, a crystal of a triethylenetetramine tetramaleate dihydrate having the structure defined by the co-ordinates of Tables 2A-2C is provided.

In certain embodiments, a crystal of a triethylenetetramine tetrafumarate tetrahydrate having the structure defined by the co-ordinates of Tables 3A-3C is provided.

Also provided are pharmaceutical compositions, including pharmaceutical compositions comprising substantially pure triethylenetetramine disuccinate. triethylenetetramine disuccinate anhydrate, triethylenetetramine tetramaleate, triethylenetetramine tetramaleate dihydrate, triethylenetetramine tetrafumarate, or triethylenetetramine tetrafumarate tetrahydrate, that also include one or more pharmaceutically acceptable excipients, carriers, and/or additives suitable for oral or parenteral application.

Uses of the disclosed and claimed compounds and pharmaceutical compositions in the treatment of various diseases, disorders and conditions are also provided.

DETAILED DESCRIPTION OF THE INVENTION

Figure 1:
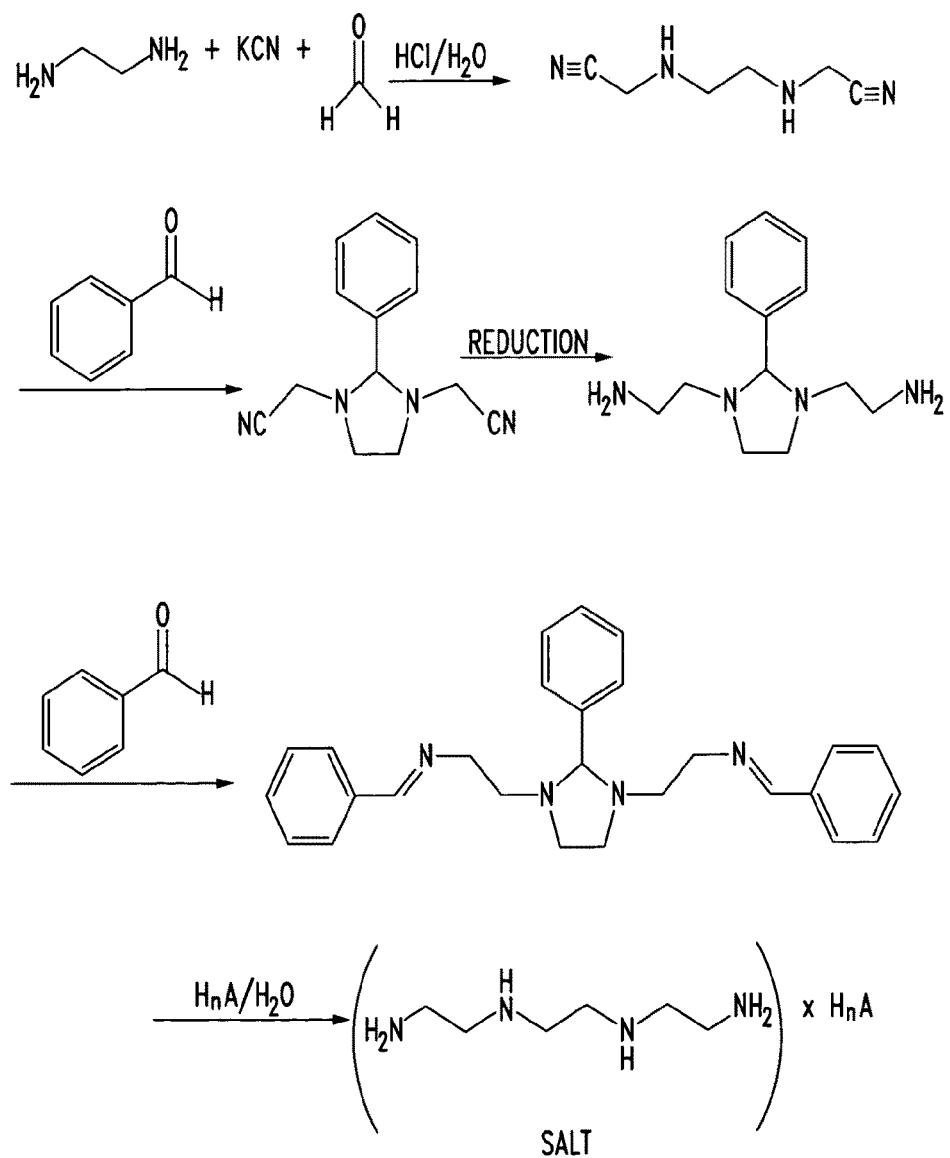
FIG. 1 shows a reaction scheme according to one embodiment of the invention for synthesizing a triethylenetetramine salt.

The subject matter of this patent is also illustrated with reference to the figures, including accompanying FIG. 1. FIG. 1 shows a summary of a preferred reaction scheme for the preparation of triethylenetetramine salts based generally on the Strecker-synthesis of a dinitrile followed by reduction of the dinitrile. The reaction includes formation of a dinitrile from ethylenediamine using formaldehyde and a cyanide salt under acidic conditions. The resulting dinitrile is derivitized to form a benzaldehyde-protected dinitrile. The protected dinitrile is reduced to form a protected diamine, and the diamine is derivatized with benzaldehyde to form a benzaldehyde protected derivative. The protected derivative is deprotected by hydrolysis with an acid to form a triethylenetetramine salt, which may include a triethylenetetramine primary salt, a triethylenetetramine secondary salt, a triethylenetetramine tertiary salt, or a triethylenetetramine quaternary salt. Other reaction schemes, including reaction schemes such as those shown in FIGS. 2 and 3, are also provided.

Figure 2:
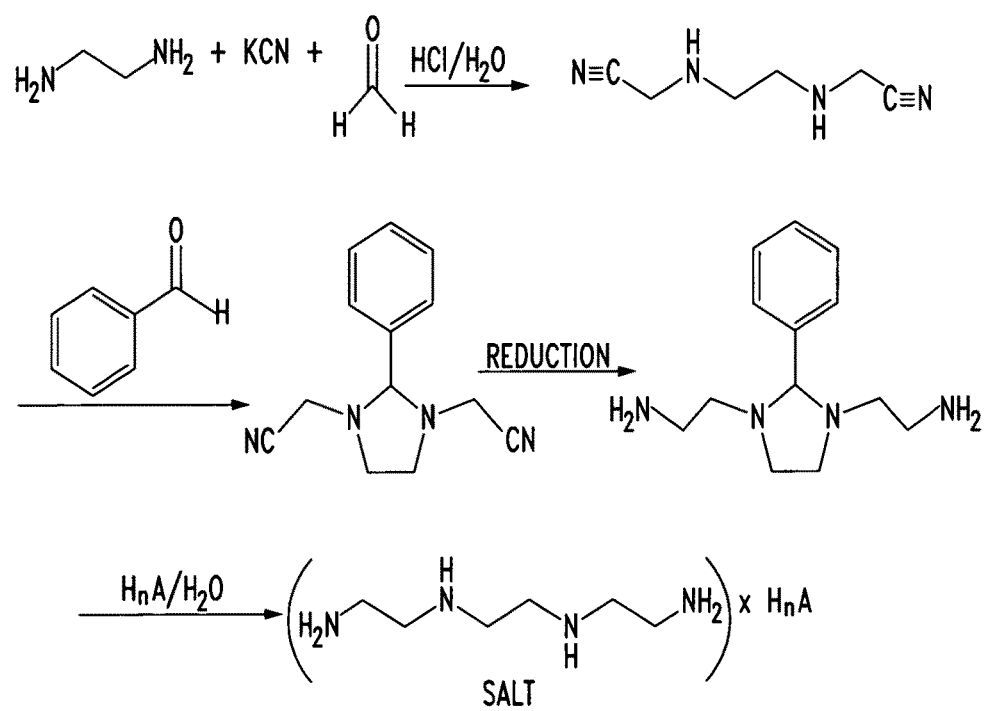
FIG. 2 shows a reaction scheme according to another embodiment of the invention for synthesizing a triethylenetetramine salt.

FIG. 2 shows a reaction scheme, similar to that of FIG. 1, wherein the protected diamine is directly hydrolyzed to form a triethylenetetramine salt, which may be a triethylenetetramine primary salt, a triethylenetetramine secondary salt, a triethylenetetramine tertiary salt, or a triethylenetetramine quaternary salt.

Figure 3:
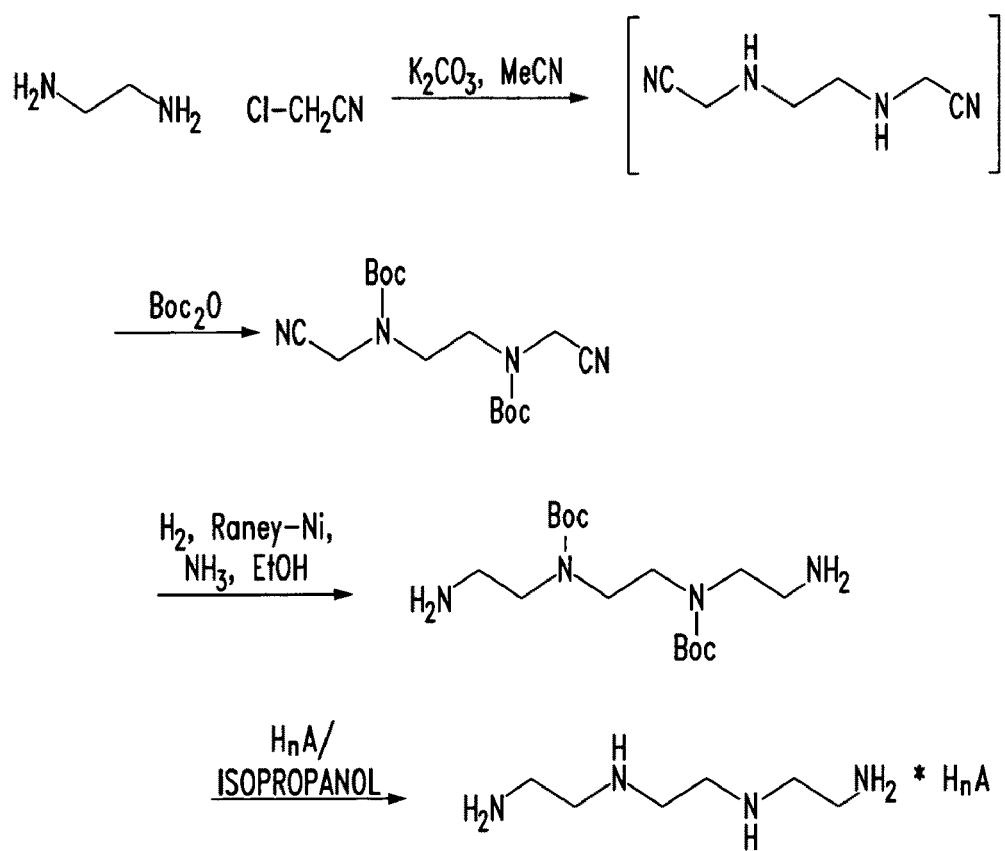
FIG. 3 shows a reaction scheme according to a further embodiment of the invention for synthesizing a triethylenetetramine salt.

FIG. 3 shows another reaction scheme for the preparation of triethylenetetramine salts based generally on the Strecker-synthesis of a dinitrile, wherein dinitrile is derivatized with $Boc_2O$ (di-tert-butyl dicarbonate) to form a Boc-protected dinitrile, the Boc-protected dinitrile is reduced in an aqueous solution of ethanol and ammonia in the presence of Raney-nickel and dihydrogen to form a protected diamine, and the protected diamine is purified by precipitation in isopropanol. The resulting compound is deprotected and hydrolyzed with an acid to form a triethylenetetramine salt, which may include a triethylenetetramine primary salt, a triethylenetetramine secondary salt, a triethylenetetramine tertiary salt, or a triethylenetetramine quaternary salt.

The patented invention includes individual steps, reaction conditions, and reactants and chemicals, as well as routes for synthesis of triethylenetetramines in high yield and purity, including by reduction of a protected dinitrile or by reduction of other intermediates or starting materials.

The patented inventions also include certain compounds that have utility, for example, as intermediates for synthesis of triethylenetetramine. Intermediates may be independently isolated and purified and/or crystallized, including during and as a part of the methods of synthesis provided herein. Isolated and purified and/or crystallized intermediates may also be stored for later use.

The steps and routes of synthesis are effective for preparation of a variety of triethylenetetramine salts. Such salts include, for example, triethylenetetramine succinate, triethylenetetramine diuccinate, triethylenetetramine diuccinate anhydrate, triethylenetetramine maleate, triethylenetetramine tetramaleate, triethylenetetramine tetramaleate dihydrate, triethylenetetramine fumarate, triethylenetetramine tetrafumarate, triethylenetetramine tetrafumarate tetrahydrate.

Also provided are polymorphs of various triethylenetetramine salts and methods for their production. In one embodiment a triethylenetetramine disuccinate polymorph has a differential scanning calorimetry (DSC) extrapolated onset/peak melting temperature of from between about 170° C. to about 190° C. See FIGS. 7 and 8.

In another embodiment a Form I polymorph of triethylenetetramine dihydrochloride has a DSC extrapolated onset/peak melting temperature of from between about 111° C. to about 132° C. See FIGS. 9 and 10. In yet another embodiment a Form II polymorph of triethylenetetramine dihydrochloride is characterized by a DSC extrapolated onset/peak melting temperature of from between about 170° C. to about 190° C. See FIGS. 11 and 12.

Also provided are triethylenetetramine salts of high purity, methods for their preparation, and dosage forms including triethylenetetramine salts.

Especially preferred individual compounds of the invention are triethylenetetramine succinate, triethylenetetramine disuccinate, and triethylenetetramine disuccinate hydrates.

Triethylenetetramine pharmaceutical compositions including one or more of, for example, triethylenetetramine succinate, triethylenetetramine disuccinate, triethylenetetramine disuccinate hydrate, triethylenetetramine maleate, triethylenetetramine tetramaleate, triethylenetetramine tetramaleate dihydrate, triethylenetetramine fumarate, triethylenetetramine tetrafumarate, triethylenetetramine tetrafumarate tetrahydrate are also provided, as are methods for their use. The pharmaceutical compositions may include, for example, one or more pharmaceutically acceptable excipients, carriers, and/or additives suitable for oral or parenteral administration.

The product formed by the described processes is substantially pure, that is, substantially free from any other compounds. Preferably, it contains less than 10% impurities, and more preferably, less than about 5% impurities, and even more preferably, less than about 1% impurities. The product thus formed is also preferably substantially pure, i.e., contains less than 10% impurity, more preferably less than 5% impurity, and still more preferably less than 1% impurity. The present invention also includes a substantially pure anhydrous crystalline form of triethylenetetramine disuccinate. The term "substantially pure" means that a sample of the relevant anhydrous crystalline form of triethylenetetramine disuccinate contains more than 90% of a single polymorphic form, preferably more than 95% of a single polymorphic form, and still more preferably more than 99% of a single polymorphic form. The present invention also provides substantially pure crystalline forms of triethylenetetramine tetramaleate dihydrate and triethylenetetramine tetrafumarate tetrahydrate, as described herein.

The term "amine protecting group" as used herein refers to any moiety that is used to protect at least one —NH— moiety and/or at least one —NH$_2$ moiety by replacement of hydrogen. Any moiety that is, for example, relatively inert to reaction conditions under which a nitrile is reduced may be used. The resulting protected structure may be linear or cyclic, and may include one or more amine protecting groups. Examples of amine protecting groups useful in the present invention include, by way of example only, methyl carbamate, ethyl carbamate, benzyl carbamate, tert-butyl carbamate, tert-butyloxycarbonyl (Boc), cyclohexanone, 2,2,6,6-tetramethyl cyclohexanone, anthrone, an alkyl group, an aryl group, or an aromatic alkyl group. Other amine protecting groups suitable for use in the invention are described, for example, in *Protective Groups in Organic Synthesis*, Third Edition, T. W. Green and P. G. M. Wuts (Wiley-Interscience, 1999). Others will be known to those in the art.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which comprise oxygen, nitrogen, sulfur or phosphorous atoms replacing one or more carbons of the hydrocarbon backbone. The term "aromatic-alkyl" includes alkyl groups substituted with one or more aryl groups.

The term "aryl" includes groups with aromaticity, including 5-and 6-membered single-ring aromatic groups that may include from zero to four heteroatoms as well as multicyclic systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a multicyclic system (e.g., tetralin, methylenedioxyphenyl).

The term "imidazolidine derivative-forming amine protecting group reagent" as used herein refers to a reactant used to protect more than one —NH— moiety by formation of an imidazolidine derivative. Examples of imidazolidine derivative-forming amine protecting group reagents include, for example, but are not limited to, an aldehyde, a ketone, formaldehyde, a substituted aromatic aldehyde, a substituted aliphatic aldehyde, a substituted alkyl-aromatic aldehyde, a substituted aromatic ketone, a substituted aliphatic ketone, and a substituted alkyl-aromatic ketone.

The term "amine protecting group reagent" as used herein refers to a reactant used to protect at least one —NH— moiety or at least one —NH$_2$ moiety including imidazolidine derivative-forming amine protecting group reagents. For example, the reagent di-tert-butyl dicarbonate (Boc$_2$O) may be used to protect about two equivalents of —NH— moiety for every one equivalent of Boc$_2$O used in a reaction. Amine protecting group reagents include, for example, Boc$_2$O, an aldehyde, a ketone, formaldehyde, a substituted aromatic aldehyde, a substituted aliphatic aldehyde, a substituted alkyl-aromatic aldehyde, a substituted aromatic ketone, a substituted aliphatic ketone, and a substituted alkyl-aromatic ketone.

The term "treating", "treat" or "treatment" as used herein includes preventative (e.g., prophylactic) and palliative treatment.

By "pharmaceutically acceptable" is meant the carrier, diluent, excipients, and/or salt must be compatible with the other ingredients of the formulation, and not deleterious to the recipient thereof.

In one embodiment, synthesis of a triethylenetetramine includes synthesis of a dinitrile from ethylenediamine and other starting materials, including, for instance, by alkylation using an haloacetonitrile (for example, chloroacetonitrile or bromoacetonitrile). A Strecker synthesis using formaldehye and a cyanide salt, for example, KCN, may be used to form a dinitrile from ethylenediamine. The resulting dinitrile is derivatized (optionally in situ) with a protecting group or groups. For example, the dinitrile may be derivatized with benzaldehyde to form a benzaldehyde-protected dinitrile or with Boc$_2$O (di-tert-butyl dicarbonate) to form a Boc-protected dinitrile. The resulting protected dinitrile is optionally purified by crystallization or another method. The protected dinitrile is reduced to form a protected diamine, and the protected diamine is deprotected by hydrolysis with an acid to form a triethylenetetramine salt, for example, a triethylenetetramine primary salt, a triethylenetetramine secondary salt, a triethylenetetramine tertiary salt or a triethylenetetramine quaternary salt. Optionally, further reaction of a triethylenetetramine tertiary salt or a triethylenetetramine quaternary salt with a base in a solvent, followed by reaction with a concentrated acid, may be used to form a triethylenetetramine secondary salt.

In another embodiment, synthesis of a triethylenetetramine salt includes synthesis of a dinitrile from ethylenediamine and other starting materials, including, for instance, by alkylation by haloacetonitrile (for example, chloroacetonitrile or bromoacetonitrile). A Strecker synthesis using formaldehye and a cyanide salt may also be used to form a dinitrile from ethylenediamine. The resulting dinitrile is the derivatized (optionally in situ) with a protecting group or groups, for example, benzaldehyde to form a benzaldehyde-protected dinitrile or Boc$_2$O (di-tert-butyl dicarbonate) to form a Boc-protected dinitrile. The resulting protected dinitrile is optionally purified by crystallization or another method. The protected dinitrile is reduced to form a protected diamine. The diamine is derivatized with a protecting group or groups to form a protected derivative, for example, with benzaldehyde to form a tri-benzaldehyde protected derivative. The protected derivative is optionally purified by crystallization or another method. A further reaction includes deprotection of the protected derivative and preparation of a triethylenetetramine salt, including a triethylenetetramine primary salt, a triethylenetetramine tertiary salt, a triethylenetetramine secondary salt, or a triethylenetetramine quaternary salt. Optionally, further reaction of a triethylenetetramine tertiary salt or a triethylenetetramine quaternary salt with a base in a solvent, followed by reaction with a concentrated acid, may be used to form a triethylenetetramine secondary salt.

In another embodiment the protected diamine undergoes a quenching step to remove remaining reduction materials.

In another embodiment a triethylenetetramine salt is prepared by the addition of an acid, which optionally, has been dissolved in a solvent prior to its addition to the protected diamine. The subsequent crystals formed are then re-crystallized in solution.

The invention also provides preparation of a purified triethylenetetramine salt by derivatization of an impure triethylenetetramine with a protecting group or protecting groups to form a protected derivative. For instance, an impure triethylenetetramine may be derivatized with benzaldehyde, forming a tribenzaldehyde protected derivative. The protected derivative is purified by crystallization or another method. A further reaction includes deprotection of the protected derivative and preparation of a triethylenetetramine salt, including a triethylenetetramine primary salt, a triethylenetetramine secondary salt, a triethylenetetramine tertiary salt or a triethylenetetramine quaternary salt. Optionally, further reaction of a quaternary or tertiary triethylenetetramine salt with a base in a solvent, followed by reaction with a concentrated acid, may be used to form a triethylenetetramine secondary salt.

A. Preparation of a Dinitrile

In one embodiment, a dinitrile intermediate such as that shown as (V) or a derivative thereof is formed.

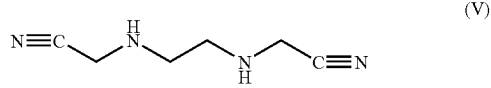

(V)

The dinitrile intermediate may be formed by a variety of routes, from a number of reagents, and under a variety of conditions. Routes, reagents and conditions include those set forth in more detail herein, and in the below Examples.

1. Dinitrile Preparation by Alkylation

One method for forming a dinitrile intermediate is by alkylation of a starting compound. In one route, a dinitrile intermediate is formed by alkylation of a diamine with a haloacetonitrile in the presence of a base and in a solvent. Suitable diamines for use as starting material for the preparation of triethylenetetramine include but are not limited to, for example, ethylenediamine, ethylenediamine hydrochloride salt, ethylenediamine hydrobromide salt, ethylenediamine diacetate salt, or other salts of ethylenediamine. Other suitable starting materials include those materials that may be changed to ethylenediamine in situ, including but not limited to ethene-1,2-diamine.

A number of haloacetonitriles are suitable for use in the alkylation, including but not limited to, for example, chloroacetonitrile and bromoacetonitrile. Although at least about two equivalents of haloacetonitrile are generally necessary for full reaction of each equivalent of ethylenediamine, the reaction may be conducted with less haloacetonitrile if incomplete conversion is desired. Greater than about two equivalents of haloacetonitrile may be used to increase the rate of the reaction. Use of greater than about three equivalents of haloacetonitrile is less favored as it may result in overalkylation of the expected dinitrile.

Bases suitable for use in alkylation include but are not limited to, for example, potassium carbonate, sodium carbonate, sodium hydroxide, potassium hydroxide, and sodium tert-butylate. The amount of base added to the reaction may vary between about 0.1 equivalents and about 2.0 equivalents of diamine starting material; the more soluble the base is in the selected solvent, the less base need be used. For example, in one embodiment of the invention, the solvent used is acetonitrile and about 2 equivalents of potassium carbonate are used; potassium carbonate is sparingly soluble in acetonitrile.

The alkylation may be performed in a number of solvents, including but not limited to acetonitrile, tetrahydrofuran (also referred to herein as "THF"), an ether, a hydrocarbon such as an alkane, or mixtures thereof. Preferably the solvent used in the reaction is non reactive at the temperature at which the reaction is conducted. The reaction may be conducted at a temperature from about the melting point of the selected solvent to about 25° C. Lower temperatures will generally lead to a slower rate of reaction.

In one embodiment of the invention, alkylation is performed by adding a solution of about 2 equivalents of chloroacetonitrile in acetonitrile to a mixture of about 1 equivalent of ethylenediamine and about 2 equivalents of potassium carbonate in acetonitrile. The addition occurs over about 30 minutes at a temperature of about 25° C., leading to completion of the reaction in about 21 hours and formation of a dinitrile intermediate.

2. Dinitrile Preparation with a Formaldehyde Starting Material

Another route for formation of a dinitrile intermediate such as (V), or a derivative thereof, is through reaction of formaldehyde with other starting materials. In one route, a dinitrile intermediate is formed by reaction of formaldehyde with an inorganic cyanide salt, an ethylenediamine source, and an acid in a solvent.

Suitable ethylenediamine sources include but are not limited to ethylenediamine, ethylenediamine dihydrochloride salt, ethylenediamine dihydrobromide salt, ethylenediamine diacetate salt, or other salts of ethylenediamine. Other suitable starting materials include materials that are reacted to form ethylenediamine in situ, including but not limited to ethene -1,2-diamine. Ethylenediamine is preferred.

Acids suitable for use in the reaction include but are not limited to hydrochloric acid hydrobromic acid, and phosphoric acid, though an acid need not be added to the reaction if an ethylenediamine salt is used as a starting material. About 2 equivalents of acid are generally used for every equivalent of ethylenediamine starting material. Fewer equivalents of acid may be used, including between about 1 and about 2 equivalents of acid, though use of fewer than about two equivalents of acid is likely to decrease the yield of the dinitrile intermediate. Between about 2 and about 3 equivalents of acid may be used, although use of excess acid is not preferred due to the possibility for the reaction to liberate hydrogen cyanide gas and this liberation will reduce the amount of cyanide available to produce the dinitrile intermediate. Liberation of hydrogen cyanide gas requires that precautions be taken due to the toxicity of hydrogen cyanide. If an ethylenediamine salt in solution is used as a starting material, 2 equivalents of acid for every 1 equivalent of ethylenediamine are generally preferred. If an acid is used, hydrochloric acid is preferred.

The formaldehyde is, for example, formaldehyde in aqueous solution or formaldehyde trimer in paraffin. Formaldehyde may be present in an amount between about 1.8 equivalents for each equivalent of ethylenediamine to about 3.0 equivalents for each equivalent of ethylenediamine. In a preferred embodiment of the invention, about 2.2 equivalents of formaldehyde are used for every equivalent of ethylenediamine.

Cyanide salts used to practice the invention include but are not limited to inorganic cyanide salts such as sodium cyanide, potassium cyanide, lithium cyanide, magnesium cyanide, and hydrogen cyanide. Use of hydrogen cyanide, a gas, is not preferred due to toxicity and the requirement that the reaction be conducted under pressure. Heavy metal cyanides such as silver cyanide, gold cyanide and copper cyanide may also be used but are not preferred due to the tendency of complexation with the dinitrile product. About two equivalents of cyanide salt are used in the reaction for every equivalent of ethylenediamine. Fewer equivalents of cyanide salt may be used, for instance between about 1 equivalents and about 2 equivalents, but use of fewer than about 2 equivalents of cyanide salt will decrease yield of the dinitrile. Cyanide salts may also be used in amounts greater than about two equivalents for each equivalent of ethylenediamine. In one preferred embodiment, 1.98 eq of cyanide, e.g., KCN, is used for the reaction.

The reaction may be conducted over a range of temperatures, including but not limited to temperatures between about −5° C. and about 35° C., including, for example, from about 4° C. and about 25° C. In one more preferred embodiment of the invention the reaction is conducted at about 20° C. The reaction may be conducted at, but is not limited to being conducted at, a pH in the range of from about 8 to about 14, from about 9 to about 12, or from about 10 to about 11. After the complete addition of formaldehyde the pH may be adjusted to the ranges of from about 1 to about 8, from about 2 to about 7, from about 3 to about 7, from about 4 to about 7, from about 5 to about 6, or from about 6 to about 7. In a preferred embodiment of the invention, the temperature is from about 4° C. and about 25° C. and the pH is from about 9 to about 12.

A variety of solvents may be used, including water and other miscible non reactive solvents that do not alter the reaction pH beyond an operative range. The pH can be adjusted with any suitable buffer, including but not limited to, for example, acetic acid, any acetic buffer or a phosphate buffer.

In one embodiment a dinitrile intermediate as shown in (V) is prepared by adding about two equivalents of potassium cyanide to about one equivalent of ethylenediamine hydrochloride salt in water. A solution of about 2.2 equivalents of formaldehyde in water is added over about 75 minutes, with the pH of the solution adjusted to about 5 with acetic acid following addition of the formaldehyde. A reaction to produce a dinitrile intermediate is complete after about 17 hours at about 20° C.

In one embodiment, a solution of 1 equivalent of ethylenediamine HCl and 1.98 equivalents of KCN in water are treated with 1.98 equivalents of formaldehyde to form the dinitrile intermediate as shown in (V). The intermediate may be isolated by the addition of benzaldehyde at a pH of from about 6 to about 7 in a two-phase system (water/n -butanol).

In a preferred embodiment, a solution of 1 equivalent of ethylenediamine and 1.98 equivalents of HCl are combined, together with 1.98 equivalents of formaldehyde. A pH range of about 7.0 is used for the reaction. In one preferred embodiment, a slight excess of ethylene diamine starting material is used to achieve the desired pH range. Preferably, the formaldehyde is added last to enhance yield, and the formaldehyde is added over 45 minutes followed by a reaction time of 2.5 hours at 17-20° C. for complete conversion of the Strecker reaction.

B. Protection of Secondary Amines and Isolation of Protected Intermediate

In another embodiment of the invention, a dinitrile as shown in (V), or a derivative thereof, is reacted with a suitable amine protecting group reagent to protect secondary amines of the dinitrile as tertiary amines. The dinitrile may be formed as described above, for example, and may but need not be first isolated.

Reaction with an amine protecting group reagent forms a protected dinitrile. Protection of the secondary amines will prevent unfavorable oxidation or reduction of amine groups of the protected dinitrile during subsequent reactions, including reduction of the nitrile groups. Optionally, a protected dinitrile is purified by crystallization prior to further reaction.

1. Protection by Formation of an Acyclic Intermediate

In one embodiment of the invention, a dinitrile such as (V) is protected by reaction with a suitable amine protecting group reagent to form a protected dinitrile as shown in Formula (VI), where the compound formed is a [{2-[cyanomethyl-R-amino]-ethyl}-R-amino]-acetonitrile, in which R is an amine protecting group. R may include, for example, but is not limited to, methyl carbamate, ethyl carbamate, benzyl carbamate, tert-butyl carbamate, tert

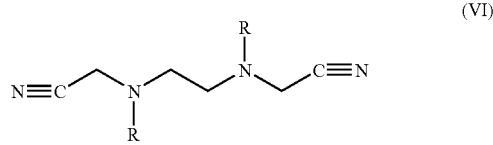

(VI)

-butyloxycarbonyl (Boc), cyclohexanone, 2,2,6,6-tetramethyl cyclohexanone, anthrone, an alkyl group, an aryl group, or an aromatic alkyl group. Other suitable amine protecting groups are described, for example, in *Protective Groups in Organic Synthesis*, Third Edition, T. W. Green and P. G. M. Wuts (Wiley-Interscience, 1999), or otherwise known in the art.

A dinitrile intermediate, such as (V), may be reacted with a number of amine protecting group reagents to affix the desired protecting groups. The dinitrile intermediate may be reacted with, for example, di-tert-butyl dicarbonate, tert-butyl carbonate, an aldehyde, a ketone, formaldehyde, a substituted aromatic aldehyde, a substituted aliphatic aldehyde, a substituted alkyl-aromatic aldehyde, a substituted aromatic ketone, a substituted aliphatic ketone, or a substituted alkyl-aromatic ketone. For complete reaction to occur, at least about two equivalents of an amine protecting group should be available in the reaction. Where two equivalents of an amine protecting group are liberated from one equivalent of an amine protecting group reagent (for example, when $Boc_2O$ is used), only one equivalent of the amine protecting group reagent need be used. Amine protecting group reagent(s) may be added to excess.

The reaction is conducted in at least one of a variety of solvents, including but not limited to water and acetonitrile. Solvent selection will be based on the identity of the protecting group. Preferably the solvent used in the addition of the protecting group is the same as that used in the formation of the dinitrile intermediate, which favors conducting reactions serially and in the same vessel. The reaction is generally performed at temperatures between about −5° C. to about 35° C., for example, from about 4° C. to about 25° C.

The protected dinitrile is optionally purified and crystallized prior to subsequent use or reaction. Purification and crystallization may be performed by extraction, crystallization, or extraction and crystallization from a solvent. Suitable solvents include, for example, ethers, alkanes including methylcyclohexane, ethyl acetate, or a mixture of solvents including a mixture of ethyl acetate and methylcyclohexane in a ratio of about 3 parts ethyl acetate to about 10 parts methylcyclohexane.

In one embodiment, an acyclic protected dinitrile is prepared by reacting a dinitrile such as (V) with about 1.2 equivalents of $Boc_2O$ in acetonitrile. Complete conversion to a Boc-protected dinitrile (Formula VI, where R is Boc) is achieved after about one hour at about 20° C. Purification and crystallization give a Boc-protected dinitrile in greater than 80% yield.

2. Protection by Formation of a Dinitrile Including an Imidazolidine Derivative

In another embodiment of the invention, a dinitrile such as (V) is protected by reaction with a suitable imidazolidine derivative-forming amine protecting group reagent to form a protected dinitrile as shown in Formula (IV), where the compound formed is (3-cyanomethyl-2-$R_1$-2-$R_2$-imidazolidin-1-yl)-acetonitrile, and where $R_1$ and $R_2$ may be the same or different, and may be, for example, hydrogen, an alkyl group including from one to twelve carbon atoms, an aryl group, or an aromatic alkyl group.

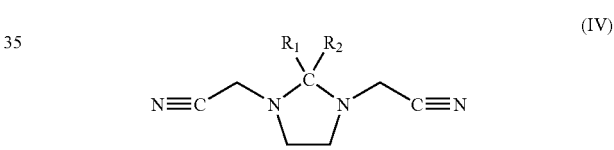

(IV)

The protected dinitrile of Formula (IV) may be formed by reaction of a dinitrile with between about 0.9 equivalents and about two equivalents of an imidazolidine derivative -forming amine protecting group reagent, including, for example, an aldehyde, a ketone, formaldehyde, a substituted aromatic aldehyde, a substituted aliphatic aldehyde, a substituted alkyl-aromatic aldehyde, a substituted aromatic ketone, a substituted aliphatic ketone, or a substituted alkyl-aromatic ketone. The reaction is conducted at a pH in the range of from about 4 to about 8, from about 6 to about 8, or from about 7 to about 8. A buffer is optionally included to maintain a desired pH. The preferred pH is about 7. Suitable buffers include but are not limited to sodium dihydrogen phosphate.

The reaction is conducted in a least one of a variety of solvents, which include, for example, water or acetonitrile. Solvent selection is based on the identity of the imidazolidine derivative-forming amine protecting group reagent. Preferably the solvent used is the same as that used in the formation of the dinitrile, so that the reactions may be conducted serially and in the same vessel. The reaction is generally performed at temperatures between about −5° C. and about 35° C., or from about 4° C. to about 25° C.

Following synthesis of a protected dinitrile, the protected dinitrile is optionally extracted with a solvent, including for example, ethyl acetate, and optionally crystallized from a mixture of butanol and cyclohexane, for example. In another embodiment a protected dinitrile is removed from solution by precipitation after addition of an alcohol. Suitable alcohols include, for example, but are not limited to, isopropanol, n-butanol, and t-butanol.

In one embodiment, a dinitrile is reacted with about 1 equivalent of benzaldehyde in water and stirred at about 20° C. for about 2 hours. Purification by crystallization in cyclohexane gives the protected dinitrile in about 40% yield of crystalline product.

In another embodiment, a dinitrile is reacted with about 1.1 equivalents of benzaldehyde in water and in the presence of a phosphate buffer. The reaction is conducted at a pH of from about 6 to about 7. An excess of butanol is added to the reaction mixture to produce a biphasic mixture. The protected dinitrile derivative (I) precipitates in about two hours, resulting in about 76% to about 78% yield of crystalline product with a purity greater than about 99 area %. The protected dinitrile derivative (I) may be isolated and crystallized. In a preferred embodiment, the crystallization step is carried out for at least 6 hours at 0° C.

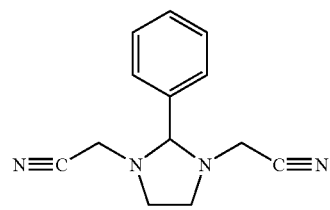

(I)

In another embodiment, an intermediate for the production of triethylenetetramines and salts thereof is 2-(3-cyanomethyl-2-phenyl-imidazolidin-1-yl)-acetamide (shown in (VII), below) or 2-(3-carbamoylmethyl-2-phenyl-imidazolidin-1-yl)-acetamide (shown in (VIII), below), both of which may be reduced and converted to triethylenetetramine as set forth herein for (I).

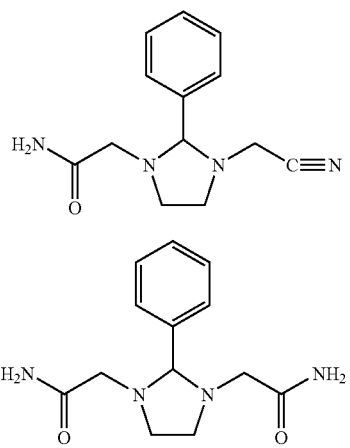

(VII)

(VIII)

C. Reduction of Nitrile Groups to Form Protected Diamine Intermediate

In a further step, a protected dinitrile is reacted with a reducing agent to create a protected diamine. As discussed further in Section D, below, the protected diamine is then either deprotected by hydrolysis in the presence of an acid to form a triethylenetetramine salt (as shown and discussed in Section D(1)), for example, or the protected diamine is reacted with further protecting groups and purified by crystallization, then hydrolyzed to form a triethylenetetramine salt (as discussed in Section D(2)).

To form a protected diamine, a protected dinitrile is reduced with a reducing agent in a solvent. Reducing agents that may be used include, for example, LiAlH$_4$ (also referred to herein as "LAH"), nickel-aluminum catalyst/H$_2$, Raney-Nickel/H$_2$, NaAlH$_4$, Li(MeO)$_3$AlH, di-isobutyl aluminum hydride, sodium bis(2-methoxyethoxy)aluminum hydride, charcoal catalyst/H$_2$ and platinum catalyst/H$_2$. Raney nickel may be recognized as a finely divided alloy of about 90% nickel and about 10% aluminum. "Raney" is a registered trademark of W.R. Grace and Company. When reduction is conducted with dihydrogen and using a catalyst, hydrogen may be applied under a pressure from between about 1.4 bar and about 5 bar, preferably under a pressure from between about 4 bar to about 5 bar. A reducing agent may be used in an amount between about 1.2 equivalents of reducing agent for every equivalent of protected dinitrile to an excess of reducing agent, or between about 1.2 equivalents of reducing agent for every equivalent of protected dinitrile to about 8 equivalents of reducing agent for every equivalent of protected dinitrile.

The reaction may be conducted at a temperature at which the solvent used is liquid. For example, if the solvent used is tetrahydrofuran, the reaction is conducted in a temperature range between about –108° C. to about 67° C. In a preferred embodiment of the invention the reaction is carried out in THF at a temperature of about 65° C.

Solvents are chosen based on the reducing agent used, and include, for example, alcohols such as methanol and ethanol, acetic anhydride, dimethylformamide (DMF), tetrahydrofuran, diglyme, dimethoxyethane, toluene, and a mixture of alcohol and water. Alcohol solvents and mixtures of alcohol and water may optionally include liquid or gaseous ammonia.

In one embodiment, a dinitrile protected by Boc groups is placed in an aqueous solution of ethanol and ammonia and hydrogenated in the presence of Raney-nickel under a hydrogen atmosphere of about 4 bar to about 5 bar. The reduction is allowed to proceed for about 15 hours at between about 20° C. and about 25° C. Concentration to dryness affords a protected diamine of Formula (II), where R is Boc, in greater than 95% yield.

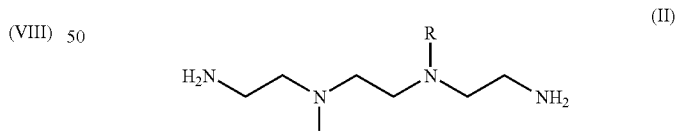

(II)

In a further embodiment, a protected dinitrile as shown in Formula (IV) where R$_1$ is hydrogen and R$_2$ is phenyl, is added to a solution of about 2.2 equivalents of lithium aluminum hydride in THF. By way of example, the reaction begins at about –30° C. and the reaction temperature is raised over the course of about 80 minutes to about 20° C. A solution of sodium hydroxide of about 4% concentration is added to the reaction until lithium aluminum hydride precipitates. A protected diamine of Formula (I), where one of R$_1$ or R$_2$ is hydrogen and one of R$_1$ or R$_2$ is phenyl, remains in THF.

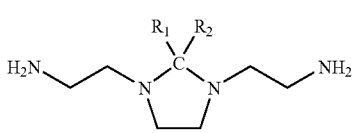

In yet another embodiment, for example, the reaction mixture containing lithium aluminum hydride in THF is treated with about one equivalent of an alcohol. The alcohol may be, for example, ethanol or methanol and is preferably methanol. The addition may take place at about 40° C. Where the alcohol used is methanol, the LiAlH$_4$ is converted to LiAlH$_3$OMe. To the LiAlH$_3$OMe is added a protected dinitrile as shown in Formula (IV), where one of $R_1$ or $R_2$ is hydrogen and one of $R_1$ or $R_2$ is phenyl, in THF at a temperature of about 40° C. followed by an aqueous quench, resulting in an increased yield of protected diamine and an eventual yield of greater than about 66% of tribenzaldehyde protected intermediate. Purity is greater than about 99 area % (ion chromatography) when the protected diamine is treated with benzaldehyde as described below in Section D(2) and the resulting tribenzaldehyde protected intermediate is crystallized and isolated. In another embodiment of the invention, the alcohol is in excess of the reducing agent.

An LAH reduction leading to the production of, for example can be considered as a four step process: the reduction itself, the aqueous quench and the removal of Al and Li salts, formation of the protected trientine, and crystallization. One such scheme for preparation of benzylidene-(2-{3-[2-(benzylidene-amino)-ethyl]-2-phenyl-imidazolidin-1-yl}-ethyl)-amine is set forth below.

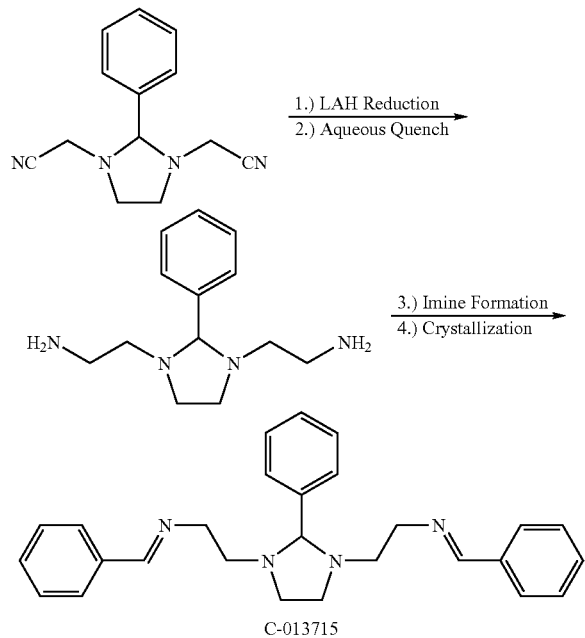

C-013715

In a certain preferred embodiment, the reducing agent LAH is treated with 1 equivalent of MeOH to increase yield and/or to facilitate filtration. In yet another embodiment, the alcohol is in excess of the reducing agent. In a certain embodiment, the equivalents of the reducing agent and the alcohol are selected in a manner sufficient to ensure complete dissolution of the reaction product and/or to increase product yield or recovery. In a certain preferred embodiment, at least about 2.5 equivalents of LAH and at least about 3.9 equivalents of MeOH are used. In another preferred embodiment, about 2.4 equivalents of LAH and at about 4.0 equivalents of MeOH are used. In another preferred embodiment, about 2.5 equivalents of LAH and at about 3.95 equivalents of MeOH are used. Use of more than about 2.5 equivalents of LAH and more than about 3.9 equivalents of MeOH, with the use of 2.7 equivalents of LAH and 3.95 equivalents of MeOH being most preferred. Quench conditions using stoichiometric amounts of MeOH are superior to aqueous conditions, which can lead to suspensions or viscous gels. In a preferred embodiment, coagulants NaOH and solid Na$_2$SO$_4$ are added to the reaction mixture followed by the addition of a saturated Na$_2$CO$_3$-solution to facilitate filtration and recovery.

For crystallization and solvent exchange, in a certain embodiment, about 2.2 equivalents of benzaldehyde are added to the reaction to obtain the tri-benzylidene-protected trientine, which is then crystallized from isopropanol. Hexane may be used as an intermediate solvent to facilitate the solvent exchange step in the reaction. In one preferred embodiment, crystallization of the protected intermediate (for example, tri-benzylidene-protected trientine) is carried out at a concentration of approximately 4-5 L/mol to increase product yield.

D. Formation of a Triethylenetetramine Salt

1. Deprotection of Protected Diamine and Formation of Triethylenetetramine Salt

In another embodiment, amine protecting groups on a protected diamine are cleaved from a diamine by reaction of an acid with a protected diamine of Formula (II) or Formula (I), forming a triethylenetetramine salt.

A triethylenetetramine salt with a triethylenetetramine to salt ratio of about 1 mole of trientine to about 3 moles of salt is formed by reacting between about 2 equivalents of acid to about 3 equivalents of acid with about one equivalent of protected diamine. In one embodiment of the invention, about 2.25 equivalents of hydrochloric acid are reacted with about one equivalent of a protected diamine of Formula (I) to form triethylenetetramine trihydrochloride salt. In another embodiment of the invention, about 4 equivalents of succinic acid are reacted with about one equivalent of a protected diamine of Formula (II) to form triethylenetetramine disuccinate salt.

A salt with a triethylenetetramine to salt ratio of about 1 mole of triethylenetetramine to about 4 moles of salt or of about 1 mole of triethylenetetramine to about 2 moles of salt is formed by reacting more than about 3 equivalents of acid for each equivalent of protected diamine. The resulting ratio of moles of triethylenetetramine to salt is determined by the acid used. For example, hydrochloric acid forms triethylenetetramine tetrahydrochloride, while succinic acid forms triethylenetetramine disuccinic acid.

The hydrolysis reaction is conducted in a solvent. Solvents suitable for the reaction include but are not limited to water, isopropanol, ethanol, methanol, or combinations thereof. Acids used in the reaction include but are not limited to hydrochloric acid, hydrobromic acid, sulfuric acid, nitric acid, or phosphoric acid and the like, or organic acids, including but not limited to acetic acid, propanoic acid, hydroxyacetic acid, pyruvic acid, oxalic acid, malonic acid, methanesulfonic acid, ethanesulfonic acid, benzenesulfonic acid, p-toluenesulfonic acid, p-sulfonic acid, cyclamic acid, tartaric acid, succinic acid, malic acid, lactic acid, citric acid, maleic acid, salicyclic acid, p-aminosalicyclic acid, pamoic acid, or fumaric acid and the like. Other suitable acids for the preparation of desired salts are described, for example, in

*Handbook of Pharmaceutical Salts Properties, Selection, and Use*, P. Heinrich Stahl and Camille G. Wermuth (Eds.) (John Wiley & Sons, 2002). Preferred acids for use in the reaction include fumaric acid, succinic acid, and maleic acid, which form triethylenetetramine fumarate, triethylenetetramine succinate, and triethylenetetramine maleate salts. Succinic acid salts are preferred, and the triethylenetetramine disuccinate salt anhydrate is most preferred. If hydrobromic acid or an organic acid is used in the reaction, heat is generally applied for salt formation to occur, although heat is not necessary.

In one embodiment, a protected diamine of Formula (II), where R is Boc, may be prepared by reacting with an aqueous solution of isopropanol and about 32% hydrochloric acid. Reaction at about 70° C. for about 30 minutes cleaves the protecting groups, and triethylenetetramine is isolated by filtration in greater than 90% yield.

In another embodiment, a protected diamine of Formula (I), where one of $R_1$ or $R_2$ is hydrogen and one of $R_1$ or $R_2$ is phenyl, is reacted with an excess of aqueous hydrochloric acid to form triethylenetetramine tetrahydrochloride salt.

2. Protection of a Diamine, Purification of a Protected Diamine, and Formation of a Triethylenetetramine Salt A protected diamine of Formula (I), in which, for example, $R_1$ may be hydrogen and $R_2$ may be phenyl, is reacted with at least two equivalents, and preferably 2.2 equivalents, of an aldehyde or ketone including for example but not limited to, formaldehyde, a substituted aromatic aldehyde, a substituted aliphatic aldehyde, a substituted aromatic ketone, a substituted aliphatic ketone, or a substituted alkyl-aromatic ketone to form the protected imidazolidine derivative of Formula (III), where $R_1$, $R_2$, $R_3$, $R_4$, $R_5$, and $R_6$ may be the same or different, and may be hydrogen, an alkyl group including from one to twelve carbon atoms, aryl group, or an aromatic alkyl group. Optionally, additional additives are also used, including but not limited to, for example, radical scavengers. Radical scavengers include, for example, BHT (2,6-di-tert-butyl-4-methyl-phenol) and lithium chloride.

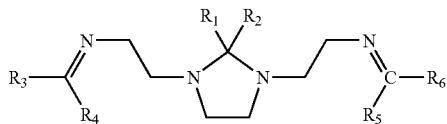

(III)

The reaction is conducted in a solvent. Solvents suitable for the reaction include but are not limited to water, isopropanol, ethanol, acetonitrile, methanol, or combinations thereof. In one embodiment, isopropanol is used as a solvent, resulting in a protected product that precipitates and is easily purified. The crystallized product is optionally washed with a solvent, preferably isopropanol, and recrystallized.

After the protected product is crystallized and purified the protecting groups are cleaved by hydrolysis in the presence of an acid, forming a triethylenetetramine salt. As discussed above, the molar ratio of triethylenetetramine to salt varies with the type and amount of acid used. Succinate salts are preferred, and most preferred is the disuccinate salt.

In one embodiment, a solution in THF of protected diamine of Formula (I), where one of $R_1$ or $R_2$ is hydrogen and one of $R_1$ or $R_2$ is phenyl, is transferred by solvent exchange to isopropanol. About 2.2 equivalents of benzaldehyde are added to the reaction mixture over about two hours, and the reaction is stirred for about 24 hours. After crystallization from isopropanol, a product of the Formula (III) is formed, wherein $R_1$, $R_3$, and $R_5$ are hydrogen and $R_2$, $R_4$, and $R_5$ are phenyl. The crystalline product, a tribenzaldehyde protected intermediate, is isolated in greater than 30% yield and at greater than 95% purity. Where, as discussed above, a protected diamine is reduced with lithium aluminum hydride that has been treated with an alcohol, yield of tribenzaldehyde protected intermediate is greater than about 66%, with purity of greater than about 99% by gas chromatography.

Also provided are the formation of triethylenetetramine quaternary salts. In an additional embodiment, a tribenzaldehyde protected intermediate is reacted with at least more than about three equivalents of aqueous hydrochloric acid, for example, to form triethylenetetramine tetrahydrochloride, which is precipitated in greater than about 90% yield and greater than about 98% purity from isopropanol.

In an additional embodiment, for example, a tribenzaldehyde intermediate is reacted with at least more than about three equivalents of aqueous maleic acid to form triethylenetetramine tetramaleate, which is precipitated from isopropanol.

In an additional embodiment, for example, a tribenzaldehyde intermediate is reacted with about three equivalents of aqueous hydrochloric acid to form triethylenetetramine trihydrochloride.

In an additional embodiment, for example, a tribenzaldehyde intermediate is reacted with about three equivalents of aqueous succinic acid to form triethylenetetramine disuccinate.

In an additional embodiment, for example, a tribenzaldehyde intermediate is reacted with about three equivalents of aqueous maleic acid to form triethylenetetramine trimaleate.

In an additional embodiment, for example, a tribenzaldehyde intermediate is reacted with about three equivalents of aqueous fumaric acid to form triethylenetetramine trifumarate.

Primary salts of triethylenetetramine are also contemplated by the processes described herein.

In a certain embodiment, the reaction is facilitated by a reduction in reaction volume to 17 L/kg of product without the TBME extraction step to ensure a high product yield. The reaction produced a fine-powder product.

In another embodiment, the reaction is facilitated by the addition of succinic acid in methanol to a solution of tribenzylidene-protected trientine in isopropanol/water. The resultant product is a sand-like product following removal of methanol by distillation, cooling to about 0° C., and subsequent recrystallization.

In a certain preferred embodiment, the removal of residual benzaldehyde is facilitated by dissolution of the product in $H_2O$ at about 30° C., followed by precipitation from $H_2O$/MeOH (3/4) at about 0° C.

In a certain preferred embodiment, the removal of residual benzaldehyde is facilitated by dissolution of the product in $H_2O$ at about 40° C., followed by precipitation from $H_2O$/MeOH (4/1) at about 0° C.

In a certain preferred embodiment, the removal of residual benzaldehyde is facilitated by dissolution of the product in $H_2O$ at about 30° C., followed by precipitation from $H_2O$/iPrOH/MeOH (3/4/4) at about 0° C.

In a certain preferred embodiment, the removal of residual benzaldehyde is facilitated by dapting the volumes of the re-crystallization procedure to increase recovery.

In a certain embodiment, a repreciptation is performed by the addition of alcohol.

3. Formation of a Triethylenetetramine Secondary Salt

In an additional embodiment, for example, a triethylenetetramine hydrochloride salt with molar ratio of about 1 mole triethylenetetramine to about two moles salt (that is, a secondary salt) is formed by reacting a triethylenetetramine hydrochloride salt with a molar ratio of about 1 mole triethylenetetramine to about 4 moles salt with a base in a solvent to produce free triethylenetetramine and free salt that is removed as a precipitate. Optionally the precipitate is washed with a solvent, for example tert-butylmethylether. Free triethylenetetramine is then reacted with at least about two equivalents of a concentrated acid, that is, an acid with a pH of less than about 1, to form a triethylenetetramine salt with a molar ratio of 1 mole of triethylenetetramine to 2 moles of salt. The triethylenetetramine secondary salt is precipitated from solution by addition of an alcohol. The triethylenetetramine secondary salt may be precipitated in high purity without successive fractionation.

In a further embodiment, for example, the acid has been pre-dissolved in a solvent prior to its addition to the free triethylenetetramine.

Also provided herein is the synthesis of polymorphs of triethylenetetramine salts.

Triethylenetetramine salts suitable for use in this embodiment include salts of a molar ratio of triethylenetetramine to salt of about 1 to about 4, including salts of the acids described above. A suitable salt is triethylenetetramine tetrahydrochloride. A particularly suitable salt is triethylenetetramine disuccinate, which is preferred.

Suitable bases for use in this embodiment include, for example, sodium methoxide and sodium ethoxide. Suitable solvents include, for example, ethanol or methanol. Suitable acids include concentrated forms of hydrochloric acid, hydrobromic acid, sulfuric acid, nitric acid, or phosphoric acid and the like, or organic acids, including, for example, acetic acid, propanoic acid, hydroxyacetic acid, pyruvic acid, oxalic (i.e., ethanedioic) acid, malonic acid, methanesulfonic acid, ethanesulfonic acid, benzenesulfonic acid, p-toluenesulfonic acid, cyclamic acid, tartaric acid, succinic acid, malic acid, lactic acid, citric acid, maleic acid, salicyclic acid, p-aminosalicyclic acid, pamoic acid, or fumaric acid and the like. Suitable alcohols for precipitation of the product include, for example, ethanol, methanol, and isopropanol.

In one embodiment about 4 equivalents of sodium methoxide are mixed with about 1 equivalent of triethylenetetramine tetrahydrochloride in a mixture of methanol and ethanol, for example. The reaction mixture is filtered, the solvent is evaporated, and the product is dissolved in tert-butylmethylether and again filtered and dissolved, giving triethylenetetramine in yield greater than about 95%. The triethylenetetramine is dissolved in about 2.0 equivalents of concentrated hydrochloric acid. Less than about 2 equivalents of concentrated hydrochloric acid may also be used. Ethanol is added and triethylenetetramine dihydrochloride precipitates in yield greater than about 86%. Purity of triethylenetetramine dihydrochloride so produced is about 100%, as determined using the methods set forth in USP27-NF22 (page 1890) for analysis of trientine, with less than about 10 ppm heavy metals as determined by USP <231> II.

E. Purification of Triethylenetetramine

The compound of Formula (III) may be used for the preparation of substantially pure triethylenetetramine. For example, triethylenetetramine in solution is reacted with between about 2 equivalents and about 4 equivalents of a suitable aldehyde or ketone, including for example, formaldehyde, a substituted aromatic aldehyde, a substituted aliphatic aldehyde, a substituted aromatic ketone, a substituted aliphatic ketone, or a substituted alkyl-aromatic ketone to form the protected imidazolidine derivative of Formula (III), where $R_1$ and $R_2$ may be the same or different, and may be for example but are not limited to, hydrogen, an alkyl group including between one and twelve carbon atoms, aryl group, or an aromatic alkyl group. In one embodiment, the aldehyde is benzaldehyde.

Suitable solvents for the reaction include but are not limited to water, isopropanol, ethanol, acetonitrile, methanol, or combinations thereof. In one embodiment, isopropanol is used as a solvent and the protected product precipitates and is easily purified. The crystallized product is optionally washed with a solvent, preferably isopropanol, and recrystallized, further purifying the product. The protected product is deprotected by reaction with an aqueous acid to form a triethylenetetramine salt as set forth in Section D(2), supra.

In another embodiment, triethylenetetramine is reacted with about 3.3 equivalents of benzaldehyde in acetonitrile at 20° C. to form a protected tribenzaldehyde intermediate. The protected tribenzaldehyde intermediate is crystallized from isopropanol and reacted in aqueous hydrochloric acid to form triethylenetetramine tetrahydrochloride in yield of about 90%.

Crystal production and analysis was performed on triethylenetetramine tetramaleate, triethylenetetramine tetrafumarate and triethylenetetramine disuccinate synthesised according to synthetic schemes described herein. Crystals of x-ray quality for triethylenetetramine tetramaleate may be grown, for example, by slow evaporation of a supersaturated solution of triethylenetetramine tetramaleate in water. The triethylenetetramine disuccinate and triethylenetetramine tetrafumarate may be grown, for example, by slow evaporation of a solution of 12.58 mg triethylenetetramine disuccinate and 7.42 mg triethylenetetramine tetrafumarate in a water/ethanol mixture (1:1, 2 ml) over a period of 3 weeks. The structural coordinates of Tables 1-3, and characterization of the crystalline structure, were determined based on measurements by x-ray powder diffraction.

The triethylenetetramine salts provided herein are of high purity. Triethylenetetramine salts may be produced with purity (calculated on a dry basis) of, for example, at least about 80% triethylenetetramine salt, at least about 85% triethylenetetramine salt, at least about 90% triethylenetetramine salt, at least about 95% triethylenetetramine salt, at least about 96% triethylenetetramine salt, at least about 97% triethylenetetramine salt, at least about 98% triethylenetetramine salt, at least about 99% triethylenetetramine salt, and about 100% triethylenetetramine salt. For example, triethylenetetramine succinate salts, such as triethylenetetramine disuccinate, may also be produced with purity (calculated on a dry basis) of, for example, at least about 80% triethylenetetramine succinate salt, at least about 85% triethylenetetramine succinate salt, at least about 90% triethylenetetramine succinate salt, at least about 95% triethylenetetramine succinate salt, at least about 96% triethylenetetramine succinate salt, at least about 97% triethylenetetramine succinate salt, at least about 98% triethylenetetramine succinate salt, at least about 99% triethylenetetramine succinate salt, and about 100% triethylenetetramine succinate salt.

In addition to the compounds and salt forms provided herein, the invention includes pharmaceutical compositions, including tablets, capsules, solutions, and suspensions for parenteral and oral delivery forms and formulations, comprising a pharmaceutically acceptable carrier and therapeutically effective amounts of one or more of the triethylenetetramine compounds herein provided. Pharmaceutical compositions including the triethylenetetramine disuccinate salt are preferred, and pharmaceutical compositions including triethylenetetramine disuccinate anhydrate are most preferred.

In human and animal therapy for the treatment of undesired copper levels, for example in the treatment of diabetes, cardiovascular disease, and other disorders, diseases and conditions noted herein, the compounds and their crystal forms described and provided herein, their pharmaceutically acceptable salts, and pharmaceutically acceptable solvates of either entity, can be administered alone, but will generally be administered in admixture with a pharmaceutical carrier selected with regard to the intended route of administration and standard pharmaceutical practice. Preferably, they are administered orally in the form of tablets containing pharmaceutically acceptable excipients, such as starch or lactose, or in capsules or ovules either alone or in admixture with excipients, or in the form of elixirs, solutions or suspensions containing flavouring or colouring agents. They can also be injected parenterally, for example, intravenously, intramuscularly or subcutaneously. For parenteral administration, they are best used in the form of a sterile aqueous solution which may contain other substances, for example enough salts or monosaccharides to make the solution isotonic with blood. For buccal or sublingual administration they may be administered in the form of tablets or lozenges which can be formulated in a conventional manner.

Doses include those previously described. See Cooper, G. J., et al., "Preventing and/or treating cardiovascular disease and/or associated heart failure," U.S. Pat. application No. 2003/0203973, published Oct. 30, 2003; and Cooper, G. J., et al., "Dosage forms and related therapies," PCT Publication No. WO2004/017956, published Mar. 4, 2004. See also U.S. Pat. No. 6,897,243, which relates in part to the use of triethylenetetramine in the treatment of diabetes.

For oral, parenteral, buccal and sublingual administration to patients, for example, the daily dosage level of the compounds herein and their pharmaceutically acceptable salts and solvates may be from about 1 mg to about 2400 mg per day (in single or divided doses). Other doses include doses from about 5 mg to about 10 mg per day, from about 10 to about 50 mg per day, from about 50 to about 100 mg per day, from about 100 mg to about 200 mg per day, about from 200 mg to about 400 mg per day, from about 400 mg to about 600 mg per day, from about 600 mg to about 1200 mg per day, from about 600 mg to about 800 mg per day, from about 800 mg to about 1000 mg per day, from about 1000 mg to about 1200 mg per day, and from about 1200 to about 2400 mg per day.

Thus, for example, tablets or capsules may contain from about 5 to about 100 mg, and up to about 300 mg or more, of active compound for administration singly, or two or more at a time, as appropriate. The physician will determine the actual dosage which will be most suitable for an individual patient and it will vary with the age, weight and response of the particular patient. The above dosages are exemplary of the average case; there can, of course, be individual instances where higher or lower dosage ranges are merited and such are within the scope of this invention.

Generally, in humans, oral administration of the compounds of the invention is the preferred route. A preferred oral dosing regimen in diabetes and heart disease for a typical man is from about 400 mg to about 1200 mg per day of compound when required. Preventative doses are lower, typically from about 1/10 to about 1/20 of the above amounts, including from about 20-40 mg to about 60-120 mg per day.

For veterinary use, a compound provided herein or a veterinarily acceptable salt thereof, or a veterinarily acceptable solvate of either entity, is administered as a suitably acceptable formulation.

Thus the invention provides a pharmaceutical composition comprising a triethylenetetramine compound provided herein, or a pharmaceutically acceptable salt thereof, or a pharmaceutically acceptable solvate of either entity, together with a pharmaceutically acceptable diluent or carrier.

It further provides a veterinary formulation comprising a triethylenetetramine compound provided herein, or a veterinarily acceptable salt thereof, or a veterinarily acceptable solvate of either entity, together with a veterinarily acceptable diluent or carrier.

The invention also provides a triethylenetetramine compound provided herein, or a pharmaceutically acceptable salt thereof, or a pharmaceutically acceptable solvate of either entity, or a pharmaceutical composition containing any of the foregoing, for use as a human medicament.

In addition, it provides a triethylenetetramine compound provided herein, or a veterinarily acceptable salt thereof, or a veterinarily acceptable solvate of either entity, or a veterinary formulation containing any of the foregoing, for use as an animal medicament.

In yet another aspect, the invention provides the use of a triethylenetetramine compound provided herein, or a pharmaceutically acceptable salt thereof, or a pharmaceutically acceptable solvate of either entity, for the manufacture of a human medicament for the curative or prophylactic treatment of a medical condition for which a copper antagonist, particularly a copper (II) antagonist, is indicated.

It also provides the use of a triethylenetetramine compound provided herein, or a veterinarily acceptable salt thereof, or a veterinarily acceptable solvate of either entity, for the manufacture of an animal medicament for the curative or prophylactic treatment of a medical condition for which a a copper antagonist, particularly a copper (II) antagonist, is indicated.

Moreover, the invention includes use of the compounds and compositions provided herein for methods for treating and/or preventing, in whole or in part, various diseases, disorders and conditions, including but not limited to glucose metabolism disorders; cardiovascular disorders; neurodegenerative disorders (e.g., Alzheimer's disease, Parkinson's disease, and Huntington's disease); insulin disorders; liver disorders; lipid/cholesterol disorders; diseases, disorders, and conditions treated or treatable with insulin; diseases, disorders, and conditions treated or treatable with hypoglycemic agents; diseases, disorders, and conditions treated or treatable with statins and the like; diseases, disorders, and conditions treated or treatable with antihypertensive agents; diseases, disorders, and conditions treated or treatable with anti-obesity agents; diseases, disorders or conditions treated or treatable with biologically active protein C or a protein C derivative; and diseases, disorders, and conditions treated or treatable with copper antagonists including, for example, copper (II) chelators.

Diseases, disorders and conditions that may be treated include, for example, atherosclerosis; peripheral vascular disease; cardiovascular disease; heart disease; coronary heart disease; restenosis; angina; ischemia; heart failure; stroke; impaired glucose tolerance; impaired fasting glucose; prediabetes; diabetes and/or its complications, including type 1 and type 2 diabetes and their complications; insulin resistance; glucose metabolism diseases and disorders; chronic hepatitis; fatty liver disease, including non-alcoholic and alcoholic fatty liver disease; steatohepatitis, including non-alcohlic and alcoholic steatohepatitis, and other conditions involving inflammation of the liver; Syndrome X; obesity and other weight related disorders; cardiomyopathy, including diabetic cardiomyopathy; hyperglycemia; hypercholesterolemia (e.g., elevated cholesterol in low-density lipoprotein (LDL- C)); pre-hypertension, hypertension, secondary hypertension, malignant hypertension, isolated systolic hypertension, and portal hypertension; hyperinsulinemia; hyperlipidemia; Alzheimer's disease Huntington's disease, and Parkinson's disease; degenerative diseases, including lupus and arthritis; nerve disease, including diabetic neuropathy; kidney disease, including diabetic nephropathy; eye disease, including diabetic retinopathy and cataracts; acute coronary syndromes, including myocardial infarction; vascular occlusive disorders; diseases, disorders associated with a hypercoagulable state or protein C deficiency, including but not limited to arterial thrombosis, arterial embolism, pulmonary embolism, deep venous thrombosis, venous thrombosis, renal vein thrombosis, mesenteric vein thrombosis, atheroembolic renal disease, thrombophlebitis, stroke, heart attack or angina, viral hemorrhagic fever, disseminated intravascular coagulation, purpura fulminans, bone marrow and other transplantations, severe burns, major surgery, severe trauma, adult respiratory distress syndrome, postphlebic syndrome, coumarin-induced skin necrosis; thrombotic diseases, disorders or conditions; sepsis and related diseases, disorders or conditions; diseases, disorders or conditions relating to undesired inflammation; thrombotic or embolic complications related to diseases, disorders or conditions including, but not limited to, diabetes, hypertension, pre-hypertension, portal hypertension, hyperlipidemia, hypercholesteremia, and/or atherosclerosis.

Diseases, disorders and conditions that may be treated also include, for example, (1) diseases, disorders and conditions characterized in part by any one or more of hyperlipidemia, hypercholesterolemia, hyperglycemia, hypertension, and/or hyperinsulinemia; (2) diseases, disorders or conditions characterized in whole or in part by (a) hypercupremia and/or copper-related tissue damage and (b) hyperglycemia, insulin resistance, impaired glucose tolerance, and/or impaired fasting glucose, and/or elevated or undesired levels of LDL-C, or predisposition to, or risk for, (a) and (b); (3) diseases, disorders and conditions characterized in whole or in part by (a) excess copper and/or copper-related tissue damage and (b) a BMI from about 25 to about 29.9 or a BMI greater than about 30 (including subjects having a BMI from about 30 to about 34.9 (obesity class I), from about 35 to 39.9 (obesity class II), and greater than about 40 (obesity class III)); (4) diseases, disorders or conditions characterized in whole or in part by (a) excess copper and/or copper-related tissue damage, and (b) protein C deficiency and/or undesired coagulation activity, or predisposition to, or risk for, (a) and (b); (5) diseases, disorders or conditions characterized in whole or in part by (a) excess copper and/or copper -related tissue damage, and (b) excess body fat; and subjects within the World Health Organization (WHO) classification for overweight and obesity (including subclassifications based on race and waist circumference), who are at risk for comorbid conditions, including hypertension, type 2 diabetes mellitus, and cardiovascular disease.

The invention includes methods for treating a subject having or suspected of having or predisposed to, or at risk for, for example, any diseases, disorders and/or conditions described or referenced herein. Such compounds may be administered in amounts, for example, that are effective to (1) decrease body and/or tissue copper levels, (2) increase copper output in the urine of said subject, and/or (3) decrease copper uptake, for example, in the gastrointestinal tract. Such compositions include, for example, tablets, capsules, solutions and suspensions for parenteral and oral delivery forms and formulations.

The invention includes methods for administering a therapeutically effective amount of a triethylenetetramine compound provided herein in a delayed release preparation, a slow release preparation, an extended release preparation, a controlled release preparation, and/or in a repeat action preparation. Such preparations may be administered to a subject having or suspected of having or predisposed to diseases, disorders and/or conditions referenced herein. Such compounds may be administered in amounts, for example, that are effective to (1) decrease body and/or tissue copper levels, (2) increase copper output in the urine of said subject, (3) decrease copper uptake, for example, in the gastrointestinal tract, and/or (4) lower LDL-C. Such compositions include, for example, tablets, capsules, solutions and suspensions for parenteral and oral delivery forms and formulations.

The invention also includes pharmaceutical compositions, including tablets and capsules and other oral delivery forms and formulations, comprising a pharmaceutically acceptable carrier and therapeutically effective amounts of a 3-hydroxy-3-methylglutaryl coenzyme A reductase inhibitor and a triethylenetetramine compound as provided herein, with triethylenetetramine disuccinate anhydrate being preferred, particularly in the disclosed crystal form. Suitable 3-hydroxy-3-methylglutaryl coenzyme A reductase inhibitors include the statins. Preferred statins are simvastatin, atorvastatin, lovastatin, pravastatin, fluvastatin, and rosuvastatin. Other statins include itavastatin and visastatin. 3-hydroxy-3-methylglutaryl coenzyme A reductase inhibitors are present in the compositions of the invention amounts, for example, that are effective to lower LDL-C. The pharmaceutical compositions may be administered in amounts, for example, that are effective to (1) decrease body and/or tissue copper levels, (2) increase copper output in the urine of said subject, (3) decrease copper uptake, for example, in the gastrointestinal tract, and/or (4) lower LDL-C. The pharmaceutical compositions may be used for treating and/or preventing, in whole or in part, various diseases, disorders and conditions, including, for example, atherosclerosis; coronary heart disease; impaired glucose tolerance; impaired fasting glucose; diabetes and/or its complications, including type 1 and type 2 diabetes and their complications; insulin resistance; Syndrome X; obesity and other weight related disorders; cardiomyopathy, including diabetic cardiomyopathy; hyperglycemia, hypercholesterolemia (e.g., elevated cholesterol in low-density lipoprotein (LDL -C)), hypertension, hyperinsulinemia, and/or hyperlipidemia; diseases, disorders and conditions characterized in part by any one or more of hyperlipidemia, hypercholesterolemia, hyperglycemia, hypertension, and/or hyperinsulinemia; and, diseases, disorders or conditions characterized in whole or in part by (a) hypercupremia and/or copper-related tissue damage and (b) hyperglycemia, insulin resistance, impaired glucose tolerance, and/or impaired fasting glucose, and/or elevated or undesired levels of LDL-C, or predisposition to, or risk for, (a) and (b).

The invention also includes pharmaceutical compositions, including tablets and capsules and other oral delivery forms and formulations, comprising a pharmaceutically acceptable carrier and therapeutically effective amounts of a hypoglycemic agent and a triethylenetetramine compound as provided herein, with triethylenetetramine disuccinate anhydrate being preferred, particularly in the disclosed crystal form. Suitable hypoglycemic agents include biguanides (for example, metformin), thiazolidinediones (for example, troglitazone, rosiglitazone, and pioglitazone), α-glucosidase inhibitors (for example, acarbose and miglitol), and sulfonylureas (for example, tolbutamide, chlorpropamide, gliclazide, glibenclamide, glipizide, and glimepiride). Other hypoglycemic agents include amylin and amylin agonists (e.g., pramlintide, which is $^{25,28,29}$Pro-h-amylin), GLP-1 and GLP-1 agonists (e.g., Arg(34)Lys(26)-(N-ε-(γ-Glu(N-α-hexadecanoyl))-GLP-1(7-37), or GLP-1LA)), and exendin and exendin agonists (e.g., exendin-4). Such compounds may be present in the compositions of the invention in amounts, for example, that are effective to (1) lower blood glucose, (2) lower serum glucose, (3) lower urine glucose, (4) lower glycosylated hemoglobin ($HbA_{1c}$) levels, (5) lower fructosamine, (6) lower postprandial glycemia, (7) ameliorate impaired glucose tolerance, (8) ameliorate impaired fasting glucose, and/or (9) lower the rate and/or severity of hypoglycemic events, including severe hypoglycemic events. The pharmaceutical compositions may be used for treating and/or preventing, in whole or in part, various diseases, disorders and conditions, including, for example, impaired glucose tolerance; impaired fasting glucose; diabetes and/or its complications, including type 1 and type 2 diabetes and their complications; insulin resistance; Syndrome X; obesity and other weight related disorders; cardiomyopathy, including diabetic cardiomyopathy; nerve diseases, including diabetic neuropathy; kidney disease, including diabetic nephropathy; eye disease, including diabetic retinopathy and cataracts; hyperglycemia, hypercholesterolemia, hypertension, hyperinsulinemia, hyperlipidemia, atherosclerosis, and/or tissue ischemia, and diseases and disorders characterized at least in part by any one or more of hyperglycemia, hypercholesterolemia, hypertension, hyperinsulinemia, hyperlipidemia, atherosclerosis, and tissue ischemia; neurodegenerative disorders, including Alzheimer's disease and Parkinson's disease; and, diseases, disorders or conditions characterized in whole or in part by (a) hypercupremia and/or copper-related tissue damage and (b) hyperglycemia; insulin resistance, impaired glucose tolerance, and/or impaired fasting glucose, or predisposition to, or risk for, (a) and (b).

The invention also includes pharmaceutical compositions, including tablets and capsules and other oral delivery forms and formulations, comprising a pharmaceutically acceptable carrier and therapeutically effective amounts of an antihypertensive agent and a triethylenetetramine compound as provided herein, with triethylenetetramine disuccinate anhydrate being preferred, particularly in the disclosed crystal form. Suitable antihypertensive agents include are those that lower blood pressure and include, for example, diuretics (including hydrochloride and chlorthalidone), α-adrenergic receptor antagonists (including prazosin, terazosin, doxazosin, ketanserin, indoramin, urapidil, clonideine, guanabenz, guanfacine, guanadrel, reserpine, and metyrosine), $β_1$-selective adrenergic antagonist (including metoprolol, atenolol, esmolol, acebutolol, bopindolol, carteolol, oxprenolol, penbutolol, medroxalol, bucindolol, levobunolol, metipranolol, bisoprolol, nebivolol, betaxolol, celiprolol, sotalol, propafenone, propranolol, timolol maleate, and nadolol), ACE inhibitors (including captopriol, fentiapril, pivalopril, zofenopril, alacepril, enalapril, enalaprilat, enalaprilo, lisinopril, benazepril, quinapril, moexipril), calcium channel blockers (including nisoldipine, verapamil, diltiazem, nifedipine, nimodipine, felodipine, nicardipine, isradipine, amlodipine, and bepridil), angiotensin II receptor antagonists (including losartan, candesartan, irbesartan, valsartan, telmisartan, eprosartan, and olmesartan medoxomil), and vasodilators (including hydralazine, Minoxidil, sodium nitroprusside, diazoxide, bosentan, eporprostenol, treprostinil, and iloprost). Other antihypertensive agents include sympatholytic agents (e.g., methyldopa), ganglionic blocking agents (including mecamylamine and trimethaphan), and endothelin receptor antagonists (including bosentan and sitaxsentan). The compounds may be present in amounts, for example, that are effective to (1) decrease body and/or tissue copper levels, (2) increase copper output in the urine of said subject, (3) decrease copper uptake, for example, in the gastrointestinal tract, and/or (4) lower blood pressure. The invention also relates to methods of using such compositions to treat subjects suffering from or at risk for various diseases, disorders, and conditions, including prehypertension, hypertension (including essential hypertension and grades 1, 2 and 3 hypertension) and related cardiovascular diseases; secondary hypertension; malignant hypertension; isolated systolic hypertension; atherosclerosis; coronary heart disease; impaired glucose tolerance; impaired fasting glucose; diabetes, including type 1 and type 2 diabetes, and their complications; insulin resistance; Syndrome X; obesity and other weight related disorders; cardiomyopathy, including diabetic cardiomyopathy; diseases and disorders characterized in part by any one or more of hypertension, hyperlipidemia, hypercholesterolemia (e.g., elevated cholesterol in low-density lipoprotein (LDL-C)), hyperglycemia, and/or hyperinsulinemia; and, characterized in whole or in part by (a) hypercupremia and/or copper-related tissue damage and (b) hypertension, insulin, or predisposition to, or risk for, (a) and (b). The invention includes methods for the use of therapeutically effective amounts of a triethylenetetramine compound provided herein in the manufacture of a medicament. Such medicaments include, for example, tablets, capsules, solutions and suspensions for parenteral and oral delivery forms and formulations. Such medicaments include those for the treatment of a subject as disclosed herein.

The compounds of the invention, particularly triethylenetetramine disuccinate anhydrate, for example, in the disclosed crystal form, may also be prepared with an anti-obesity agent or an insulin.

Doses for such triethylenetetramine compounds, salts and/or solvates as provided herein are envisage to be administered in a therapeutically effective amount, for example, to lower copper values in a subject.

The compounds of the invention may also be pre-complexed with a non-copper metal ion prior to administration for therapy. Metal ions used for pre-complexing are pharmaceutically acceptable and have a lower association constant for the copper antagonist than that of copper. For example, a metal ion for pre-complexing a copper antagonist that chelates $Cu^{2+}$ is one that has a lower binding affinity for the copper antagonist than $Cu^{2+}$. Preferably, the non-copper metal ion has an association constant for triethylenetetramine that is equal to or less than about $10^{-19}$, more preferably less than or equal to about $10^{-18}$, still more preferably less than or equal to about $10^{-15}$, even more preferably less than or equal to about $10^{-12}$, $10^{-10}$, or $10^{-9}$, and most preferably less than or equal to about $10^{-8}$, $10^{-7}$ or $10^{-5}$.

Preferred metal ions for precomplexing include, for example, calcium (e.g., $Ca^{2+}$), magnesium (e.g., $Mg^{2+}$), chromium (e.g., $Cr^{2+}$ and $Cr^{3+}$), manganese (e.g., $Mn^{2+}$), zinc (e.g., $Zn^{2+}$), and iron (e.g., $Fe^{2+}$). Most preferred metal ions for precomplexing are calcium, zinc, and iron. Other metals include, for example, cobalt (e.g., $Co^{2+}$), nickel (e.g., $Ni^{2+}$), silver (e.g., $Ag^{1+}$), and selenium (e.g., $Se^{4+}$). Non-copper metals are chosen with regard, for example, to their relative binding to the triethylenetetramine, the dose of the triethylenetetramine to be administered, and relative to potential toxicity following displacement of the non-copper metal ion. Examples of pre-complexed triethylenetetramines include triethylenetetramine disuccinate pre-complexed with a metal ion having a binding constant lower than copper, for example, triethylenetetramine disuccinate pre-complexed with zinc or calcium (e.g., $Zn^{2+}$ and $Ca^{2+}$). Without intending to be bound to any particular mechanism or mode of action, precomplexing allows lower dosing.

The invention includes methods for the use of a therapeutically effective amount of a triethylenetetramine compound provided herein in the manufacture of a dosage form. Such dosage forms include, for example, tablets, capsules, solutions and suspensions for parenteral and oral delivery forms and formulations. Such dosage forms include those for the treatment of a subject as disclosed herein.

The invention includes an article of manufacture comprising a vessel containing a therapeutically effective amount of a triethylenetetramine compound provided herein and instructions for use, including use for the treatment of a subject.

The invention includes an article of manufacture comprising packaging material containing one or more dosage forms containing a triethylenetetramine compound provided herein, wherein the packaging material has a label that indicates that the dosage form can be used for a subject having or suspected of having or predisposed to any of the diseases, disorders and/or conditions described or referenced herein. Such dosage forms include, for example, tablets, capsules, solutions and suspensions for parenteral and oral delivery forms and formulations.

In yet another aspect of this invention is a kit comprising (a) at least one triethylenetetramine compound, or salt or crystal thereof, and a pharmaceutically acceptable carrier, excipient and/or additive in a unit dosage form, and (b) means for containing the unit form. Since the present invention has an aspect that relates to the treatment of the disease/conditions described herein with a combination of active ingredients, the invention also relates to combining separate pharmaceutical compositions in kit form. A kit may contain a pharmaceutical composition comprising triethylenetetramine compound, or salt or crystal thereof, as provided herein, either alone or together with a second compound as described herein.

The kit comprises means for containing the composition such as a container, a bottle or a foil packet. Typically the kit comprises directions for the administration of the composition.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening. It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The invention includes a formulation comprising a triethylenetetramine compound provided herein in amounts effective to remove copper from the body of a subject and reduce elevated copper levels. Such formulations include, for example, tablets, capsules, solutions and suspensions for parenteral and oral delivery forms and formulations.

The following experiments set forth in the following examples are illustrative of the present inventions and are not intended to limit the inventions.

EXAMPLES

Raw materials used in the Examples were purchased from Fluka Company (Switzerland) and Aldrich Chemicals (Milwaukee, Wis.). Product purity was assessed by thin-layer chromatography and/or NMR. In some cases a gas chromatography analysis was performed. Qualitative thin layer chromatography (TLC) was generally used for in process controls to monitor conversions.

TLC parameters for those examples related to Boc were as follows:

| TLC-plate: | $SiO_2$ F60 | |
|---|---|---|
| Eluent: | Methanol | |
| Detection | 1) 0.2 g Ninhydrin in 100 ml ethanol | |
| | 2) Heating to 110° C. | |
| $R_f$-values: | Ethylenediamine (1) | $R_f$ = 0.0-0.30 (yellow) |
| | Dinitrile (2) | $R_f$ = 0.45-0.48 (orange/pink) |
| | Boc-protected Dinitrile (3) | $R_f$ = 0.49-0.52 (light brown) |
| | Boc-protected Diamine (4) | $R_f$ = 0.19-0.21 (brown) |
| | Triethylenetetramine | $R_f$ = 0.0-0.10 (yellow) |

Gas chromatography analysis was used to assess the purity of the benzaldehyde derivatized intermediates. The gas chromatography analysis was combined with NMR, and was not used to monitor conversions due to column degradation after a few injections.

Gas chromatography parameters were as follows:

| Column: | DB-5, 15 m × 0.25 mm i.d. × 0.25 μm film | | |
|---|---|---|---|
| Mobile Phase: | $H_2$ @ 1.5 mL/min const. flow | | |
| | Time [min] | Temp. [° C.] | Heating Rate [° C./min] |
| Temp. program: | 0 | 40 | 0 |
| | 1.2 | 40 | 0 |
| | 4.2 | 70 | 10 |
| | 13.2 | 300 | 33.3 |
| | 17.2 | 300 | 0 |
| Injector Temp. | 250° C. | | |
| Detector Temp. | 300° C. (FID) | | |
| Detection: | Step: Auto | | |
| | Average: on | | |

| | |
|---|---|
| Split flow/Split Ratio: | 75 mL/min/1:50 |
| Injection Volume: | 1.0 μL |

Example 1

Example 1 describes the preparation of (3-cyanomethyl-2-phenyl-imidazolidin -1-yl)-acetonitrile.

Ethylenediamine hydrochloride salt (66.5 g, 0.5 mol, 1.0 eq) was dissolved in water (350 ml). KCN (65.1 g, 1.0 mol, 2.0 eq) was added to the reaction mixture endothermically. A solution of formaldehyde (36.5% in water) (83 ml, 1.1 mol, 2.2 eq) was added to the reaction mixture over about 75 min, so that the internal temperature stayed below about 25° C. The reaction mixture was cooled with an ice bath. After the addition of 50% of the formaldehyde solution the pH was brought from about 12 to about 10 by adding acetic acid.

After complete addition of the formaldehyde solution the pH was adjusted to about 5 with acetic acid. The reaction mixture was slowly stirred at 20° C. for 17 hours. Thin layer chromatography showed complete conversion. Benzaldehyde (53.05 g, 50.8 mL, 0.5 mol, 1.0 eq) was added, and the reaction mixture was stirred at 20° C. for 40 min. The reaction mixture was extracted with ethyl acetate (100 mL). The aqueous phase was extracted 3 times with ethyl acetate (3×100 mL).

Figure 4:
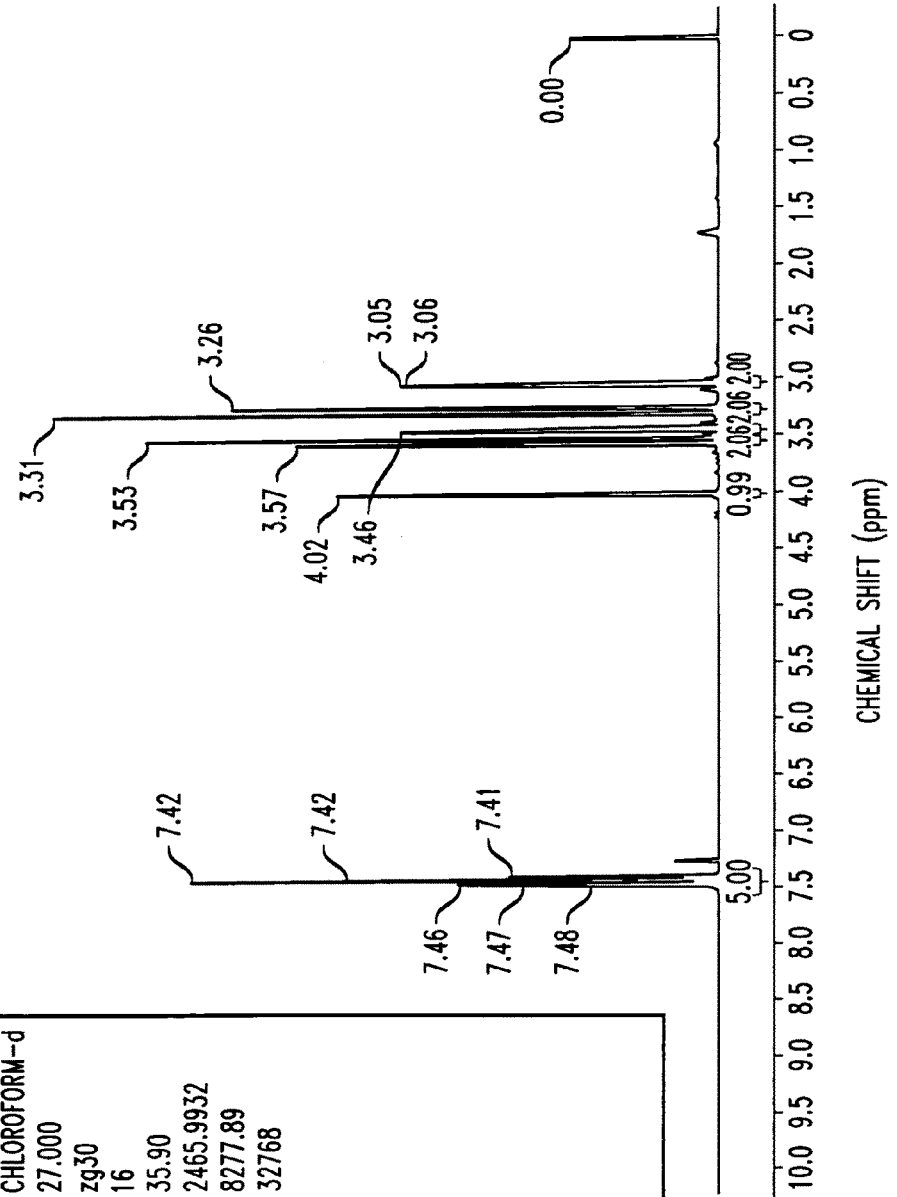
FIG. 4 shows an $^1$H-NMR spectrum of benzaldehyde-protected dinitrile (3-cyanomethyl-2-phenyl-imidazolidin-1-yl)-acetonitrile as synthesized in Example 1. NMR values include a frequency of 400.13 Mhz, a 1H nucleus, number of transients is 16, points count of 32768, pulse sequence of zg30, and sweep width of 8278.15 Hz.

The combined organic phases were concentrated to dryness on a rotary evaporator to afford 203 g of crude (3-cyanomethyl-2-phenyl-imidazolidin-1-yl) -acetonitrile. The crude product was crystallized from n-butanol/cyclohexane (125 mL/75 mL). The product was filtered, washed with n-butanol/cyclohexane (35 mL/35 mL) and dried on a rotary evaporator (external temperature: 40° C., p=20 mbar). 22.7 g (3-cyanomethyl -2-phenyl-imidazolidin-1-yl) -acetonitrile was obtained as a white solid, corresponding to a yield of 20%. The purity was 99.5 area % as measured by gas chromatography. The $^1$H-NMR spectrum of (3-cyanomethyl-2-phenyl-imidazolidin-1-yl)-acetonitrile is shown in FIG. 4.

Example 2

This example demonstrates another preparation of a 3-cyanomethyl-2-phenyl -imidazolidin-1-yl)-acetonitrile.

1 equal molar of ethylenediamine and 2 equal moles of KCN were mixed in a reaction vessel pre-purged with nitrogen gas. Water was added to the reaction mixture and the feeding vessel was rinsed with water. The feeding vessel was then charged with 2 equal moles of HCl (32%) and the solution was then slowly added to the mixture so that the internal temperature of the reaction did not exceed 25° C. Following the HCl addition, the reaction mixture was cooled to about 3° C. 2 equal moles of formaldehyde solution (30% dissolved in water) was added to the reaction mixture with cooling over 40 minutes. The reaction mixture was then stirred for 2.5 hours at a temperature range of 15° C. to 20° C. For NMR analysis, 5-10 mg of the reaction mixture was dissolved in 1000 μL D2O and analyzed by proton -NMR. The spectrum indicated complete disappearance of ethylenediamine. Thirty minutes after the addition of formaldehyde, a 0.5 equal molar of NaH$_2$PO$_4$ solution was added to the reaction mixture at an internal reaction temperature of between 10° C. to 12° C. The resultant pH of the reaction mixture dropped to about 6. N-butyl alcohol was added to the reaction mixture at an internal temperature of 11.6° C. Thirty minutes after the addition of n-butyl alcohol, 1 equal mole of benzaldehyde was added to the reaction mixture at an internal reaction temperature of 11° C. to 12° C. After half of the benzaldehyde has been added, 3-cyanomethyl-2-phenyl -imidazolidin-1-yl)-acetonitrile seed crystals were added to the solution. The reaction mixture was then cooled to −4° C. over the span of 4 hours then stirred at −4° C. for 11.5 hours. The filter cake was washed with deionized water at 15-19° C., then washed with n-butyl alcohol at 0° C. in two portions; the reaction mixture was then washed with isopropyl alcohol at −2° C. Crude (3-cyanomethyl-2-phenyl-imidazolidin-1-yl)-acetonitrile was transferred into a PROVATEC-dryer and dried at 50° C. under 4 mbar of pressure. The reaction produced (3-cyanomethyl-2-phenyl -imidazolidin-1-yl)-acetonitrile at 99.31% purity, at 86.7% yield.

In another run, the reaction produced (3-cyanomethyl-2-phenyl-imidazolidin-1-yl)-acetonitrile at 99.63% purity, at 85.1% yield.

Example 3

This Example demonstrates the preparation of benzylidene-(2-{3-[2-(benzylidene-amino)-ethyl]-2-phenyl-imidazolidin-1-yl}-ethyl)-amine.

A solution of LiAlH$_4$ (34.5 mmol, 3.0 eq) in THF (112.5 mL) was cooled to −30° C. A solution of the compound of Example 1, (3-cyanomethyl-2-phenyl -imidazolidin-1-yl) -acetonitrile (2.6 g, 11.5 mmol, 1.0 eq), in THF (78 mL), was added over about 25 min. The reaction mixture was stirred at −30° C. for 10 min and then warmed to 20° C. over 80 min. A while solid precipitated. Thin-layer chromatography showed complete consumption of the starting material. Diethyl ether (8 mL) was added to the reaction mixture. Water (6 mL) was exothermically added to the reaction mixture at 0° C. over 20 min, and H$_2$ evolution occurred. Benzaldehyde (2.7 g, 2.6 mL, 25.3 mmol, 2.2 eq) was added at 20° C. and the reaction mixture stirred for 45 min.

Figure 5:
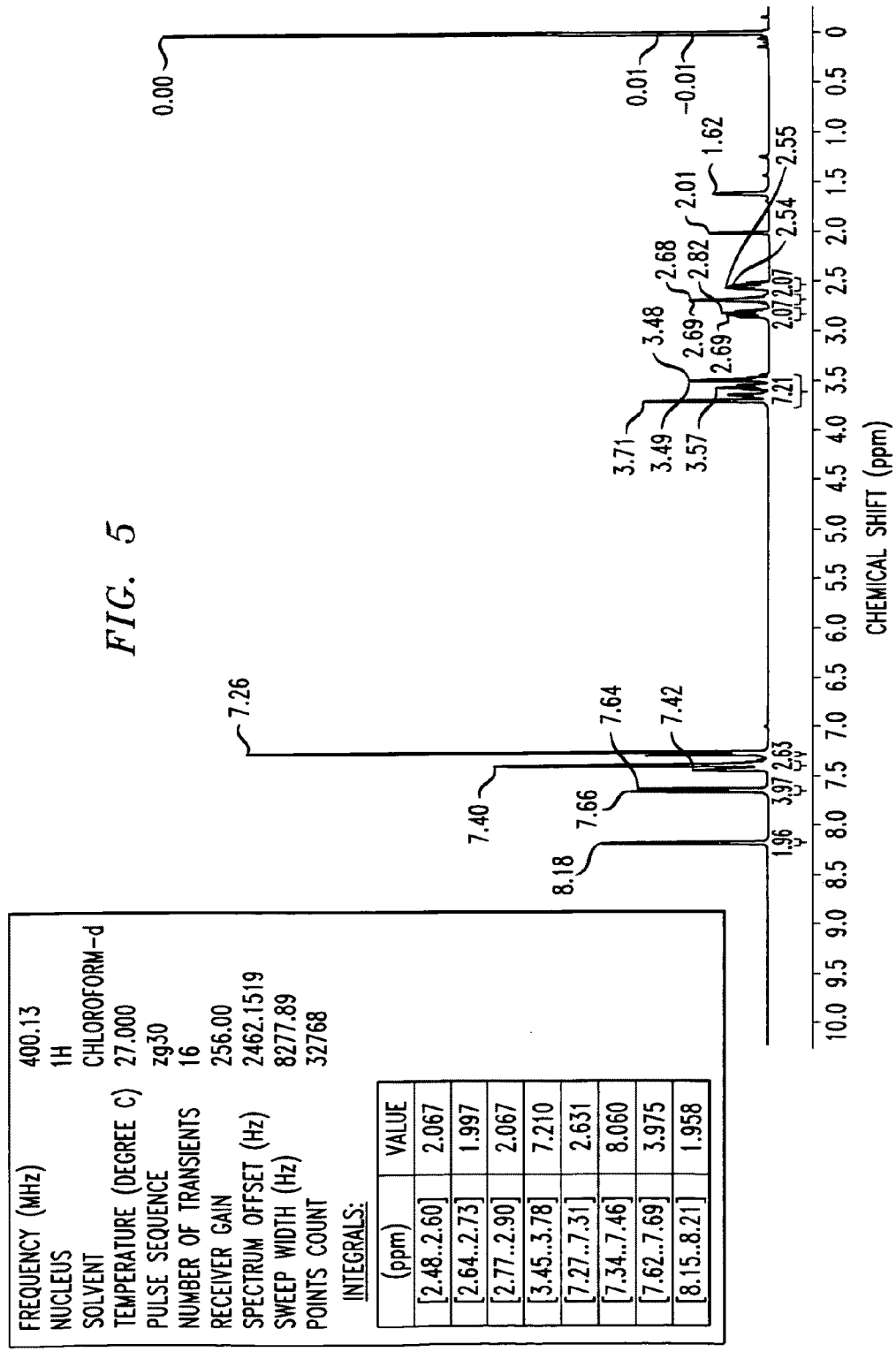
FIG. 5 shows an $^1$H-NMR spectrum of the tri-benzaldehyde derivative benzylidene-(2-{3-[2-(benzylidene-amino)-ethyl]-2-phenyl-imidazolidin-1-yl}-ethyl)-amine in $CDCl_3$, as synthesized in Example 2. NMR values include a frequency of 400.13 Mhz, a 1H nucleus, number of transients is 16, points count of 32768, pulse sequence of zg30, and sweep width of 8278.15 Hz.

The suspension was filtered and washed twice with diethyl ether (2×15 mL). The filtrate was concentrated to dryness to afford 4.0 g of crude benzylidene-(2-{3-[2-(benzylidene-amino)-ethyl]-2-phenyl-imidazolidin-1-yl}-ethyl)-amine. The crude product was recrystallized from acetonitrile. Filtration at 0° C. and drying on a rotary evaporator gave 1.2 g of benzylidene-(2-{3-[2-(benzylidene-amino)-ethyl]-2-phenyl -imidazolidin-1-yl}-ethyl)-amine as a white solid (purity: 95.8 area % by gas chromatography). A second crystallization from the mother liquor gave 0.3 g of product. The total yield was 32%. The $^1$H-NMR spectrum of the benzylidene-(2-{3-[2-(benzylidene-amino)-ethyl]-2-phenyl -imidazolidin-1-yl}-ethyl)-amine in CDCl$_3$ is shown in FIG. 5.

Example 4

This example demonstrates another preparation of a benzylidene-(2-{3-[2-(benzylidene-amino)-ethyl]-2-phenyl-imidazolidin-1-yl}-ethyl)-amine.

1 equal mole of (3-cyanomethyl-2-phenyl-imidazolidin-1-yl) -acetonitrile and THF were mixed in a reactor and the reactor was purged with nitrogen gas. The reaction mixture was then transferred to a feeding vessel. The reactor was washed with THF and the solution was added into the mixture in the feeding vessel. 3 equal moles of LiAlH$_4$ in THF solution was added to the reactor. 4 equal moles of methanol and THF were mixed in another feeding vessel, this mixture was added over the next 40 minutes at an internal temperature of 35 to 40° C. into the main reaction mixture. The solution was then heated to an internal temperature of 40° C. under constant stirring for one additional hour. The mixture of methanol and THF was slowly added to the mixture in the feeding vessel at an internal temperature of 39° C.-45° C. The mixture was stirred at an internal temperature of 40° C. for an additional 30 minutes. The mixture was then cooled to an internal temperature of 10° C. within 1 hour. Na₂SO₄ and NaOH were added to the reaction mixture. Saturated Na₂CO₃-solution was added at an internal temperature of 10-18° C. via a feeding vessel. The reaction mixture was stirred at an internal temperature of 10° C. overnight. Na₂HPO₄ was added to the mixture and the reaction suspension was filtered into the stirring vessel. The filter cake was washed with two volumes of THF. The suspension of Na2HPO4 and the filtrate was stirred for one hour in the stirring vessel and then filtered over a nutsch. The filter cake was washed with THF. Both filtrates (filtration and washing) were then transferred into the second reactor (via inline-filter). 2 equal moles of benzaldehyde was added to the filtrate at 20° C. (via inline filter). THF was distilled off at an internal temperature of 10-20° C. and at a pressure of 130-210 mbar, external temperature (ET)=50° C. Hexane was then added (ET=40° C.) to the mixture. Water was then distilled off at an internal temperature of 16-20° C., with a pressure of 170-190 mbar and a ΔT of 40-43° C. The hexane was further distilled off at an internal temperature of 16° C., at a pressure of 160-180 mbar and ET=44° C. Isopropanol was added to the reactor via a feeding vessel. Isopropanol was distilled off at IT=10-27° C., p=30-114 mbar and ET=50° C. The reaction mixture was stirred for an hour at an internal temperature of 35° C. The reaction mixture was then cooled to −5° C. and stirred overnight. The nutsch was again purged with nitrogen and the suspension was again filtered. The filter cake was washed with cold (6° C.) isopropanol. The product, benzylidene-(2-{3-[2-(benzylidene-amino)-ethyl]-2-phenyl-imidazolidin-1-yl}-ethyl)-amine, was allowed to dry in a PROVATECH dryer at a temperature of 30-40° C. at a pressure of less than or equal to 30 mbar. The reaction was carried out in five independent reaction vessels with the following results: Flask 1 gave benzylidene-(2-{3-[2-(benzylidene-amino)-ethyl]-2-phenyl-imidazolidin-1-yl}-ethyl)-amine as an off-white solid with a purity of 99.93% as measured by gas chromatography, which represented a total yield of 84.85%. Flask 2 gave benzylidene-(2-{3-[2-(benzylidene -amino)-ethyl]-2-phenyl-imidazolidin-1-yl}-ethyl)-amine as an off-white solid with a purity of 99.42% as measured by gas chromatography, which represented a total yield of 77.1%. Flask 3 gave benzylidene-(2-{3-[2-(benzylidene-amino)-ethyl]-2-phenyl -imidazolidin-1-yl}-ethyl)-amine as an off-white solid with a purity of 99.89% as measured by gas chromatography, which represented a total yield of 78.3%. Flask 4 gave benzylidene-(2-{3-[2-(benzylidene-amino) -ethyl]-2-phenyl-imidazolidin-1-yl}-ethyl)-amine as an off-white solid with a purity of 99.87% as measured by gas chromatography, which represented a total yield of 82.7%.

Example 5

Figure 6:
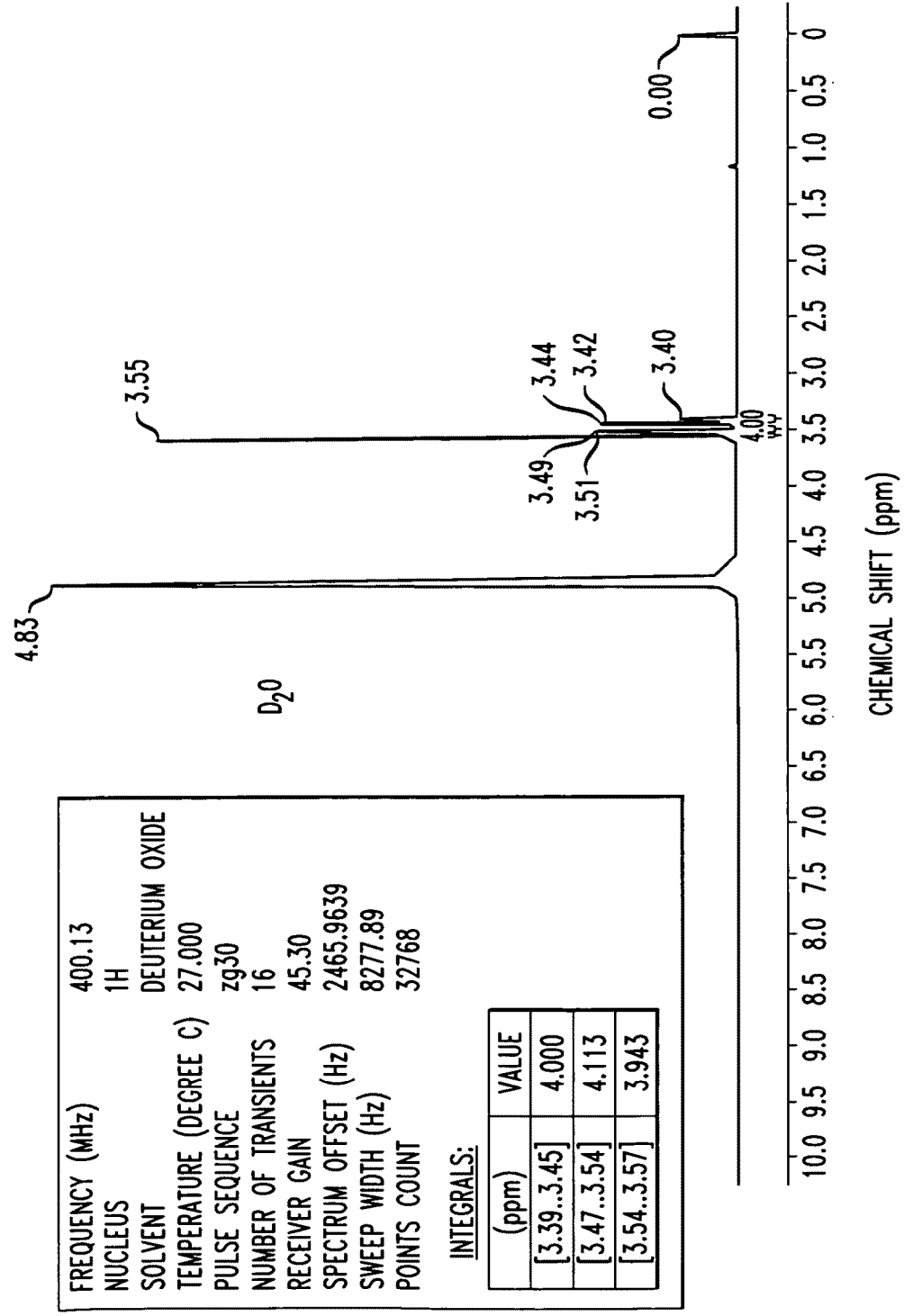
FIG. 6 shows an $^1$H-NMR spectrum of a triethylenetetramine hydrochloride salt in $D_2O$, as synthesized in Example 3. NMR values include a frequency of 400.13 Mhz, a 1H nucleus, number of transients is 16, points count of 32768, pulse sequence of zg30, and sweep width of 8278.15 Hz.

This Example demonstrates the preparation of a triethylenetetramine tetrahydrochloride. Benzylidene-(2-{3-[2-(benzylidene-amino)-ethyl]-2-phenyl-imidazolidin-1-yl}-ethyl)-amine (3.15 g, 7.67 mmol), was dissolved in water (5 mL) and concentrated HCl (5 ml) and stirred for 5 min at 20° C. The reaction mixture was extracted once with TBME (10 mL). The aqueous phase was treated with isopropanol (30 mL), whereupon the product, triethylenetetramine tetrahydrochloride, precipitated. The product was filtered, washed with isopropanol (10 mL) and dried on a rotary evaporator. 2.01 g of crystallized triethylenetetramine tetrahydrochloride was obtained as a white solid. FIG. 6 shows an ¹H-NMR spectrum of triethylenetetramine tetrahydrochloride in D₂O.

Example 6

This Example demonstrates a dinitrile reduction of an intermediate that was protected by, for example, a benzaldehyde protecting group. A benzaldehyde protecting group was be used as shown in Scheme 1, in which a solution of a [2-(cyanomethyl-amino) -ethylamino]-acetonitrile intermediate (2) was treated with 1 equivalent of benzaldehyde and stirred at 20° C. for about 2 hours. Work-up resulted in crude (3-cyanomethyl-2-phenyl -imidazolidin-1-yl)-acetonitrile (5) in 84% yield. Purification by crystallization from cyclohexane resulted in (3-cyanomethyl-2-phenyl-imidazolidin-1-yl)-acetonitrile (5) in 40% yield.

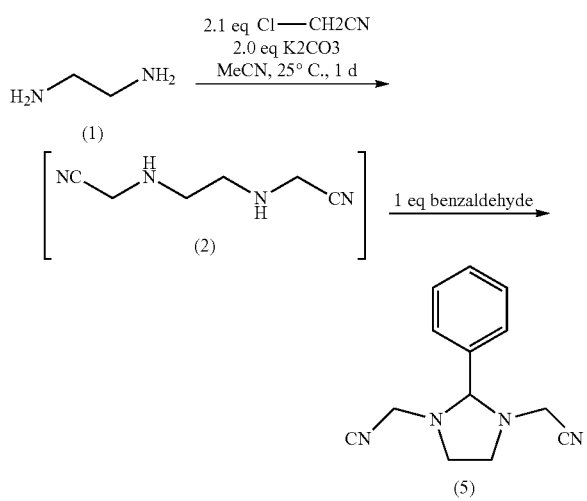

The synthesis of [2-(cyanomethyl-amino)-ethylamino]-acetonitrile intermediate (2) was accomplished by a Strecker-type synthesis as shown, for example, in Scheme 2.

A solution of 1 equivalent of ethylenediamine hydrochloride salt in water was treated with 2 equivalents of KCN. A solution of 2.2 equivalents of formaldehyde in water was added over about 75 minutes and the pH was adjusted to 5 with acetic acid. Thin-layer chromatography showed complete conversion after about 17 hours at 20° C. The intermediate (2) was not isolated but was treated with 1 equivalent of benzaldehyde. Extraction with ethyl acetate and crystallization from butanol/cyclohexane resulted in (3-cyanomethyl-2-phenyl

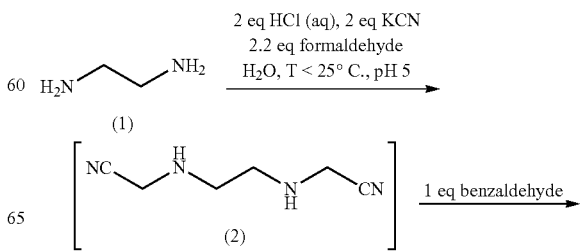

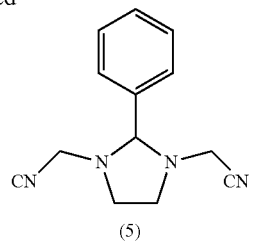

-imidazolidin-1-yl)-acetonitrile (5) in 20% yield with a purity of 99.5 area % by gas chromatography. The crystallinity of (3-cyanomethyl-2-phenyl-imidazolidin-1-yl)-acetonitrile (5) allowed simple purification of the intermediate.

Alternatively, a dinitrile intermediate is treated with sodium phosphate monobasic (NaH$_2$PO$_4$) and benzaldehyde at a temperature of about 10° C. and a pH of about 6 to 7, followed by addition of n-butylalcohol, resulting in the production of (3-cyanomethyl-2-phenyl-imidazolidin-1-yl)-acetonitrile (5).

Example 7

This Example demonstrates the reduction of (3-cyanomethyl-2-phenyl-imidazolidin-1-yl)-acetonitrile (5) with LiAlH$_4$ and protection using benzaldehyde. As shown in Scheme 3, a solution of 1 equivalent of (3-cyanomethyl-2-phenyl-imidazolidin-1-yl)-acetonitrile (5) was added to a solution of 3 equivalents of LiAlH$_4$ in THF at about −30° C. The reaction mixture was warmed to about 20° C. over 80 minutes, whereupon thin-layer chromatography showed complete conversion. The reaction mixture was treated with water (vigorous, exothermic reaction with H$_2$-evolution) and aluminum salts were removed by filtration. Isolation of the amine intermediate 2-[3-(2-Amino-ethyl)-2-phenyl-imidazolidin-1-yl]-ethylamine (8) as a pure compound was not readily achieved. To add protecting groups and allow isolation the amine intermediate (8) was reacted in situ with 2.2 equivalents of benzaldehyde after aqueous quench. After work-up and crystallization from acetonitrile, crystalline benzylidene-(2-{3-[2-(benzylidene-amino)-ethyl]-2-phenyl-imidazolidin-1-yl}-ethyl)-amine (7) was obtained in 32% yield and with a purity of 95.8 area % by gas chromatography.

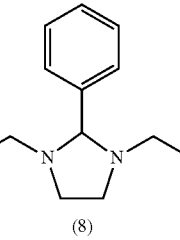

Example 8

This Example demonstrates the preparation of crystalline intermediate benzylidene-(2-{3-[2-(benzylidene-amino)-ethyl]-2-phenyl-imidazolidin-1-yl}-ethyl)-amine (7). This preparation is significant, for example, because the crystalline intermediate (7) may be hydrolyzed in the presence of an acid to form a triethylenetetramine salt. Hydrochloric acid is used for the production of triethylenetetramine tetrahydrochloride, as shown in Scheme 4. The formation of triethylenetetramine dihydrochloride is shown in Scheme 5. The use of succinic acid for the production of a disuccinate salt is shown in Scheme 6. The use of fumaric acid and maleic acid to produce triethylenetetramine tetrafumaric salt and triethylenetetramine tetramaleic salt, respectively, is depicted in Scheme 7 and Scheme 8, respectively.

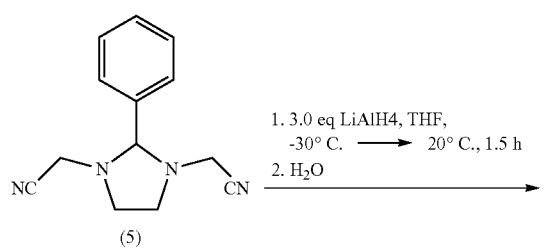

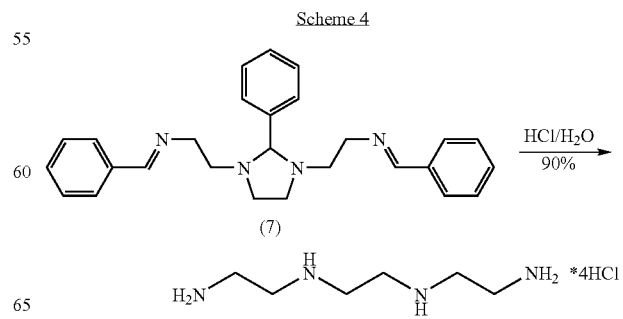

Scheme 6
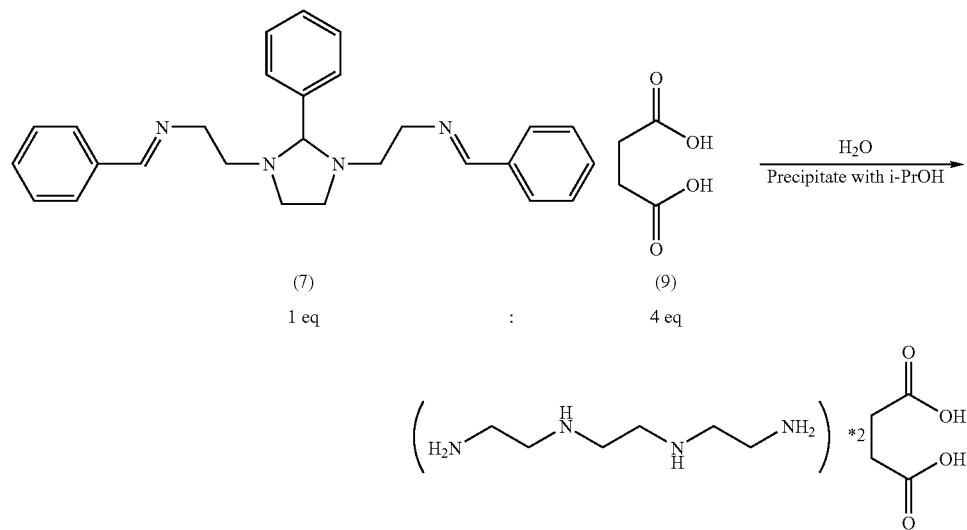
Scheme 7
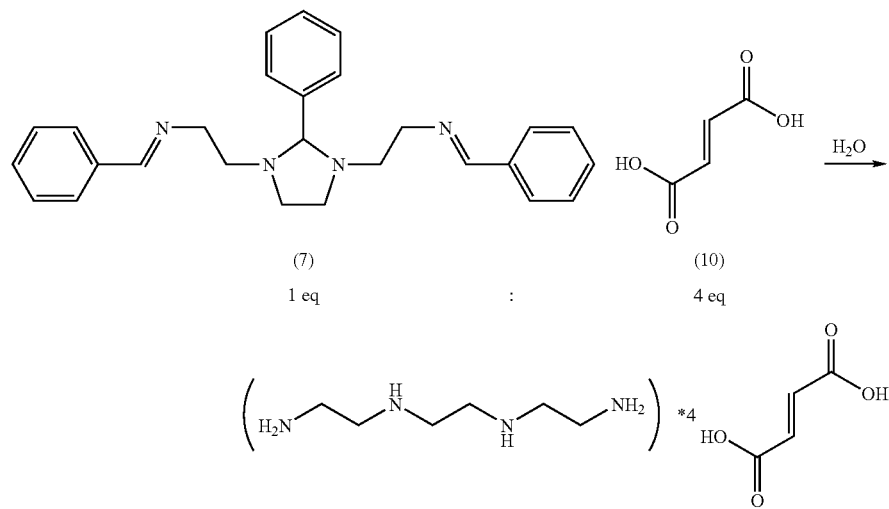
Scheme 8
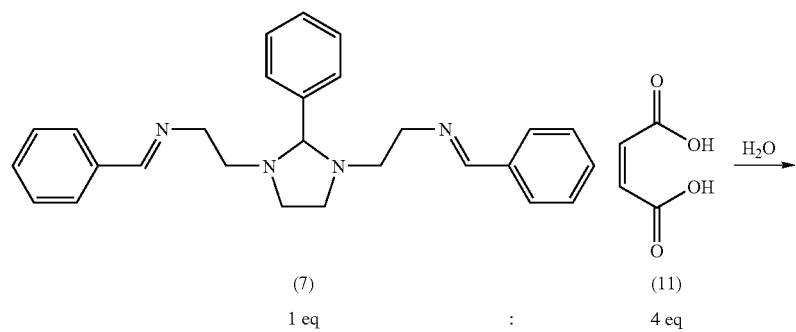

-continued

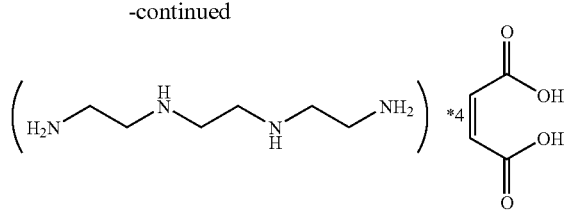

Salts formed from succinic acid and maleic acid exhibited non-hygroscopic properties. Phosphate, mesylate, benzoate, citrate, and malate salts exhibited low crystal formation, sulfate salt exhibited a low melting point, and tartrate salt was hygroscopic. Salts in all manner of stoichiometric and nonstoichiometric ratios are contemplated by the invention, including salts present in an acid to triethylenetetramine ratio of 1 to 1, 2 to 1, 3 to 1, and 4 to 1. The properties of a number of triethylenetetramine salts produced by a method of the invention are set forth in Table 1. All of the salts set forth in Table 1 were found to be colorless, and the salts of the hydrochloric, succinic, and maleic acid were obtained as free flowing crystalline powders. The salt of fumaric acid was obtained as a wooly solid. The fumarate, succinate, and maleic acid salts were exposed to 80° C. for nine days, and the IR, $^1$H-NMR, and DSC after that time showed no changes.

TABLE 1

| Salt | Yield [%] | Stoichiometry $n_{acid}:n_{trientine}$ $^1$H-NMR; EL. Analysis | Triethylenetetramine [% w/w] | Bulk Density [g/cm$^3$] | Melting point [° C.] DSC (onset/peak) | Solubility (water) [g/L] | pH |
| --- | --- | --- | --- | --- | --- | --- | --- |
| Fumaric | 83 | 4:1 | 23.9 | 0.09 | 186.01/ 187.97 | 10.3 | 3.32 (Sat. Sol'n) |
| Maleic | 78 | 4:1 | 23.9 | 0.19 | 180.34/ 181.86 | 10.8 | 2.91 (Sat. Sol'n) |
| Succinic | 87 | 2:1 | 38.2 | 0.33 | 180.05/ 179.91 | >389 | 5.22 (0.16 M) |
| Hydrochloric | 82 | 2:1 | 66.7 | 0.21 | 122.53/ 122.92 | very soluble | 8.0 (0.02 M) |

Salts of the invention were also analyzed for hygroscopicity, as shown in Table 2, after exposure to a controlled humidity atmosphere (38.6% relative humidity, 19° C.) for several days. The succinate and the maleic acid salts may be considered non-hygroscopic salts. The dihydrochloride salt absorbed water in a reversible fashion; the DSC of a dried sample was identical to that of a sample with almost 0% water content. The fumarate salt absorbed water to a constant amount of about 3.51%, which was interpreted as the formation of a monohydrate. In some embodiments of the invention, seed crystals may be added to aid salt crystal formation.

TABLE 2

Results of Karl Fischer Water Determination (in % assay)

| | initial | 24 hours | 3 days | 7 days |
| --- | --- | --- | --- | --- |
| Dihydrochloride | | | | |
| Sample 1 | 0.07 | 0.24 | 10.63 | — |
| Comparison Maleate | | | | 0.21 |
| Sample 1 | 0.04 | 0.04 | 0.04 | 0.03 |
| Comparison Succinate | | — | — | — |
| Sample 1 | 0.01 | 0.02 | 0.02 | 0.01 |

TABLE 2-continued

Results of Karl Fischer Water Determination (in % assay)

| | initial | 24 hours | 3 days | 7 days |
| --- | --- | --- | --- | --- |
| Comparison Fumarate | | — | — | — |
| Sample 1 Comparison | 1.00 | 3.51 | 3.51 | |

Figure 7:
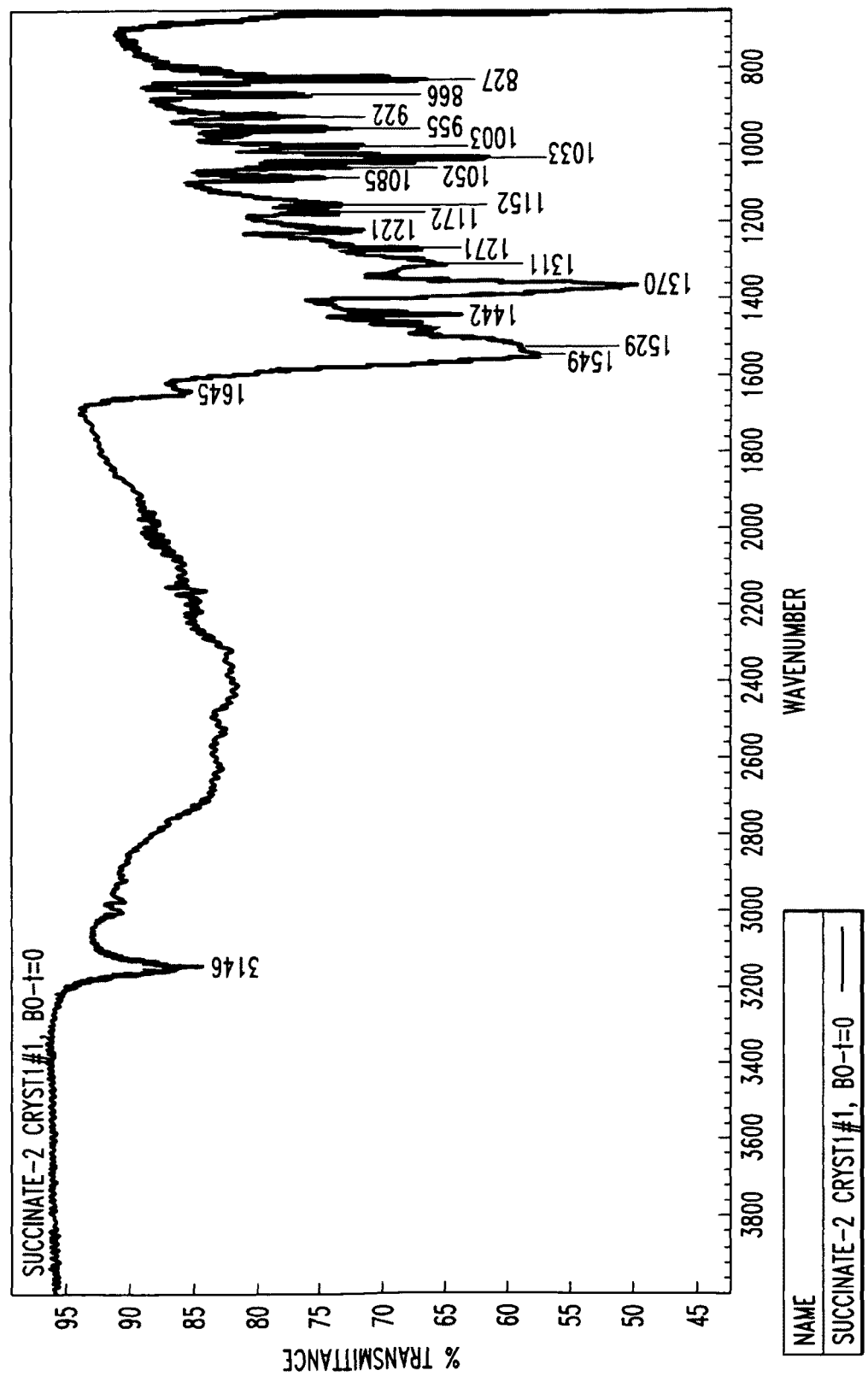
FIG. 7 shows an infrared spectrum of a polymorph of triethylenetetramine disuccinate.
Figure 8:
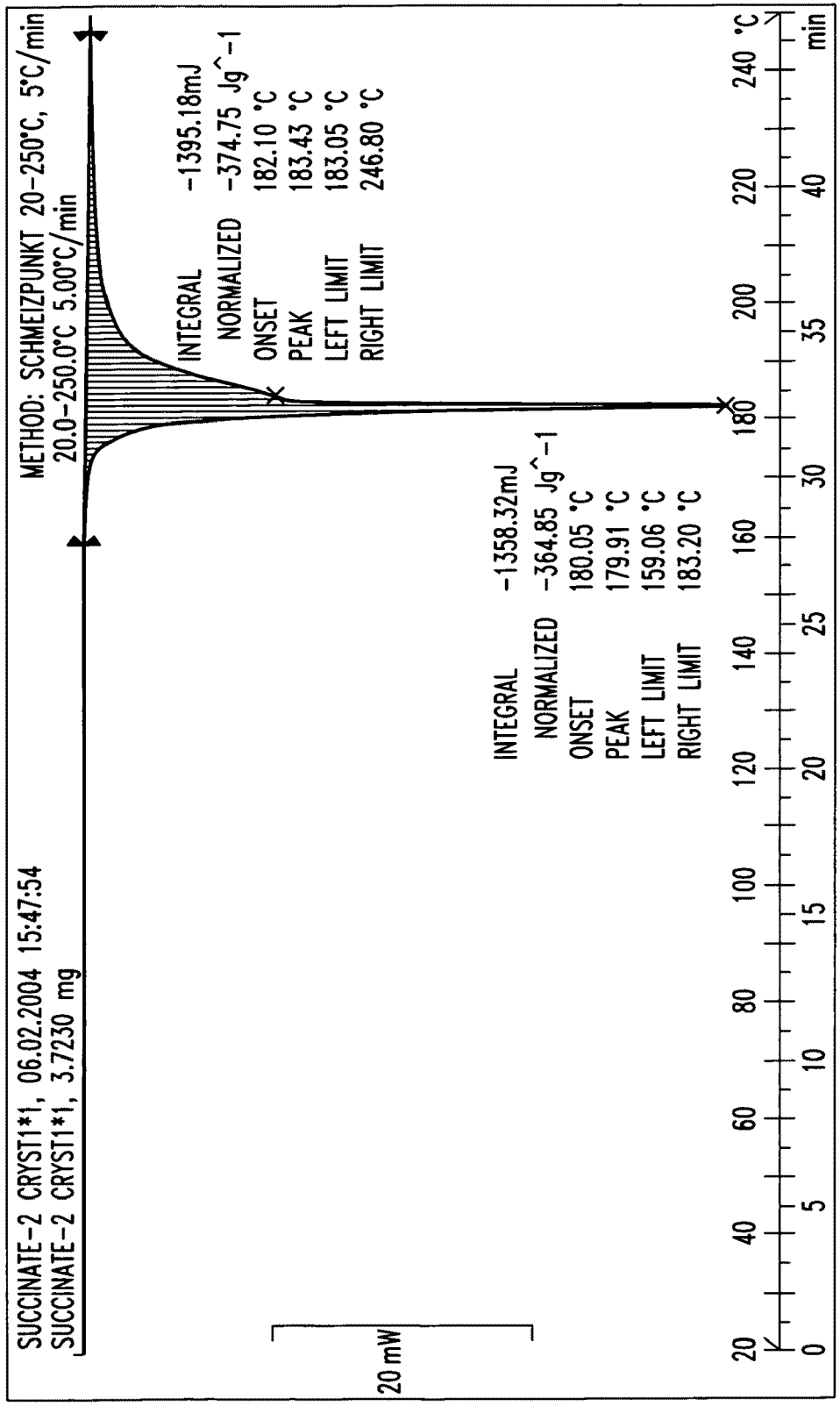
FIG. 8 shows a DSC graph of a polymorph of triethylenetetramine disuccinate.

Various polymorphs of triethylenetetramine salts may be formed by the invention. Infrared analysis of a triethylenetetramine disuccinate produced by an embodiment of the invention is set forth in FIG. 7. Infrared peaks were located at wavenumbers 3148, 1645, 1549, 1529, 1442, 1370, 1311, 1271, 1221, 1172, 1152, 1085, 1052, 1033, 1003, 955, 922, 866, and 827. Characteristic peaks of interest to identify the triethylenetetramine disuccinate include 3148, 1549, 1529, 1442, 1370, and 1311 corresponding to —OH, —NH$_2$, —NH$_2$, —O, —CH$_2$, CH$_2$ respectively. DSC analysis of a triethylenetetramine disuccinate, with onset/peak melting points of 180.05/179.91° C. is shown in FIG. 8.

Figure 9:
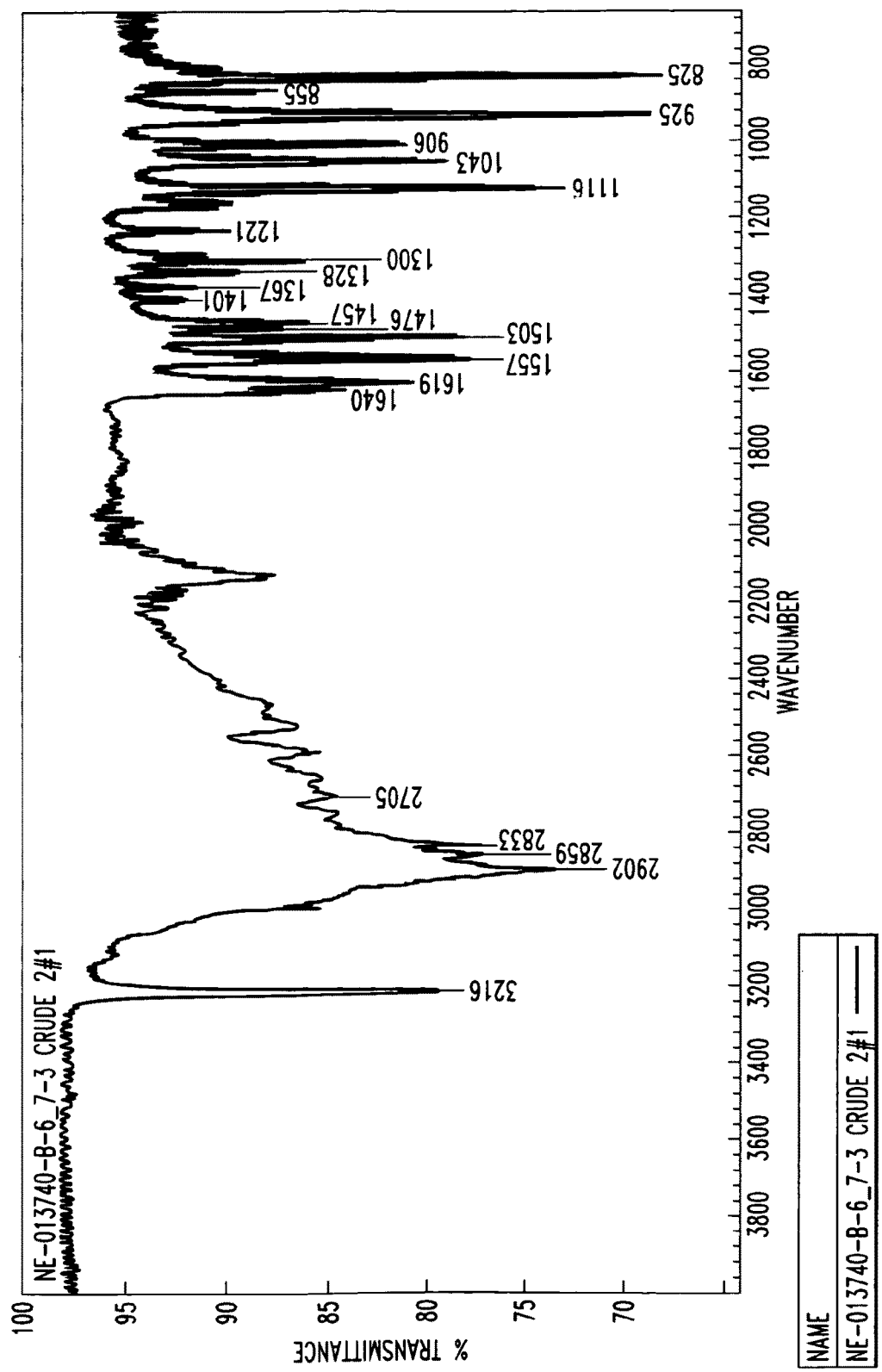
FIG. 9 shows an infrared spectrum of the Form I polymorph of triethylenetetramine dihydrochloride.
Figure 10:
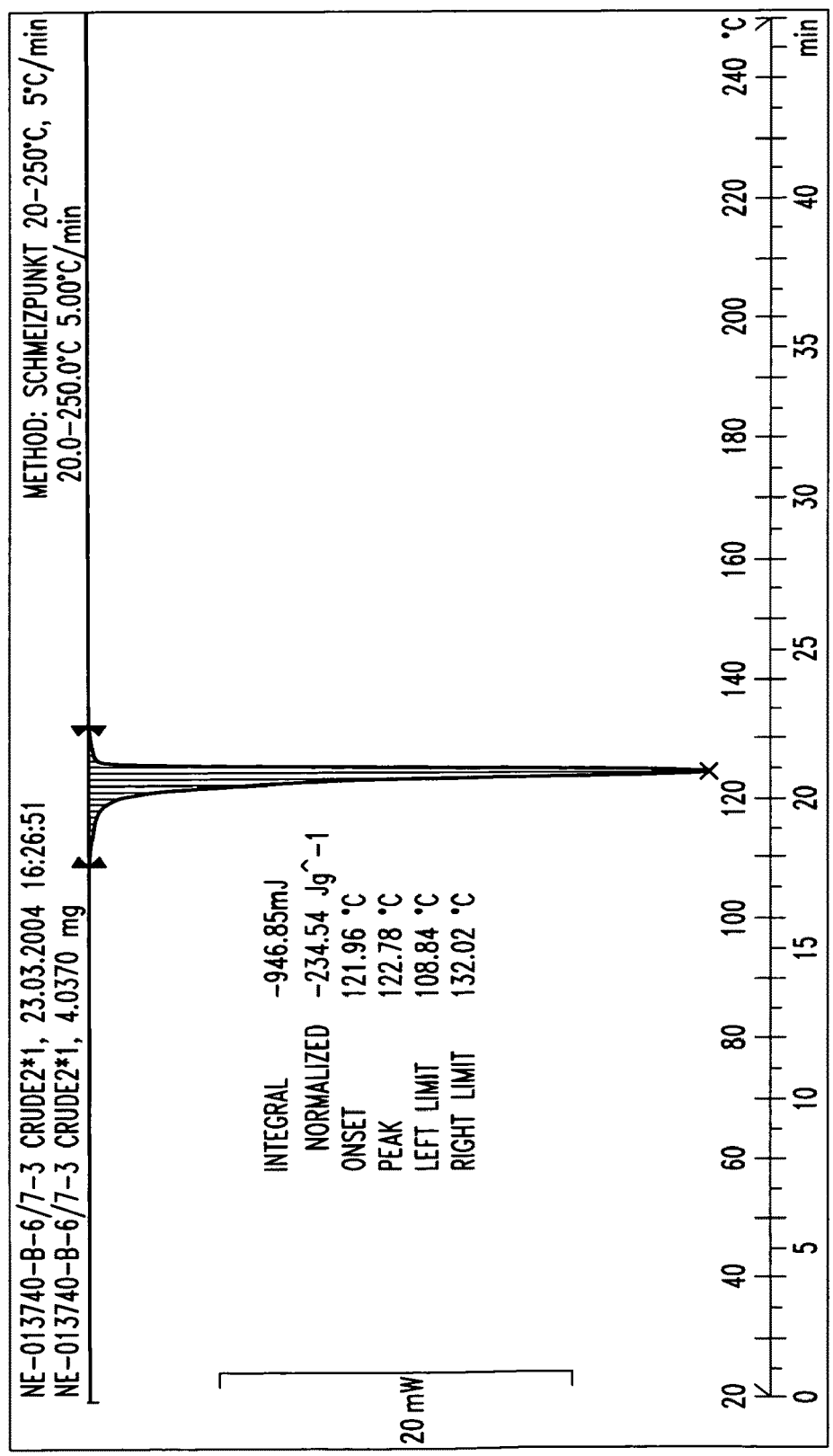
FIG. 10 shows a DSC graph of the Form I polymorph of triethylenetetramine dihydrochloride.
Figure 11:
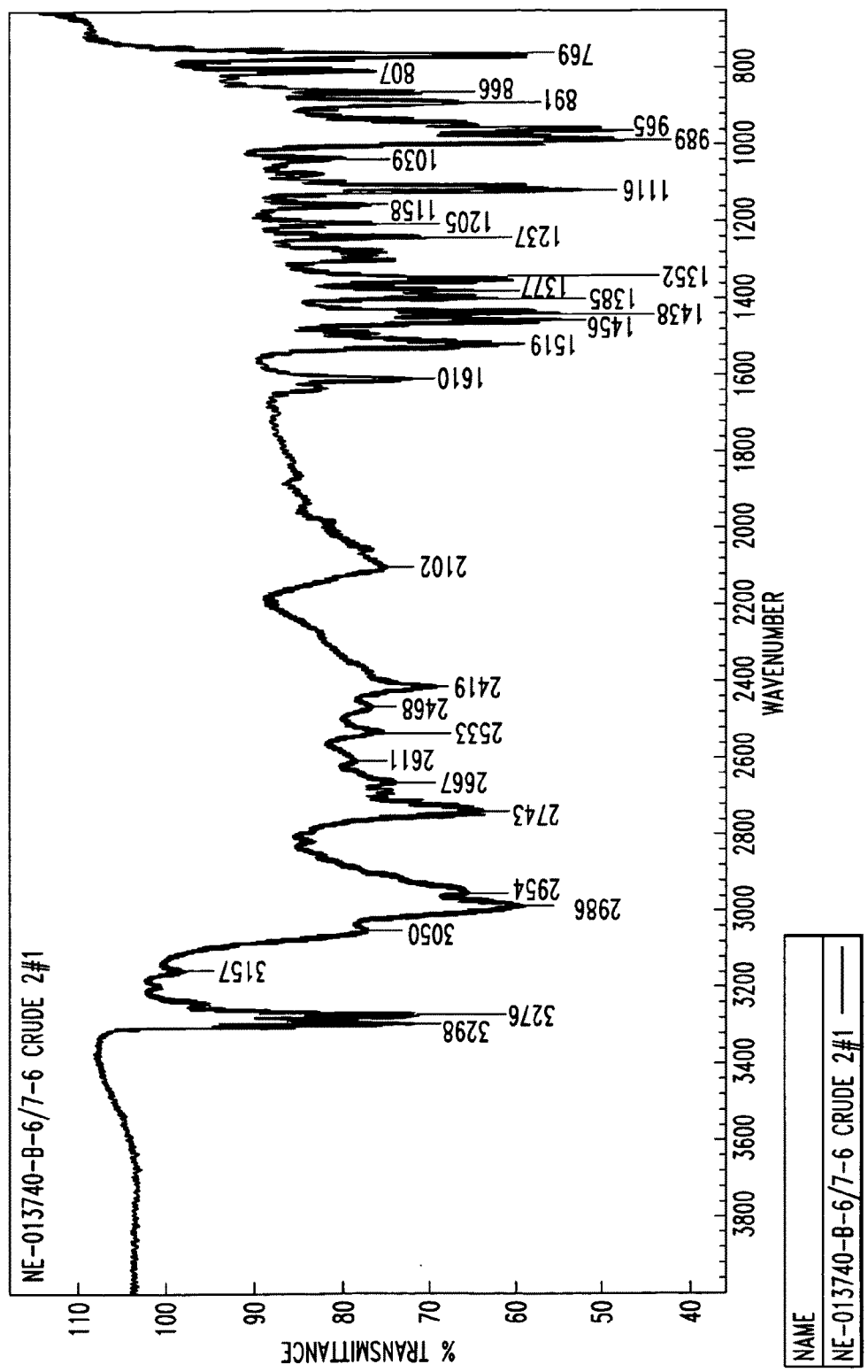
FIG. 11 shows an infrared spectrum of the Form II polymorph of triethylenetetramine dihydrochloride.
Figure 12:
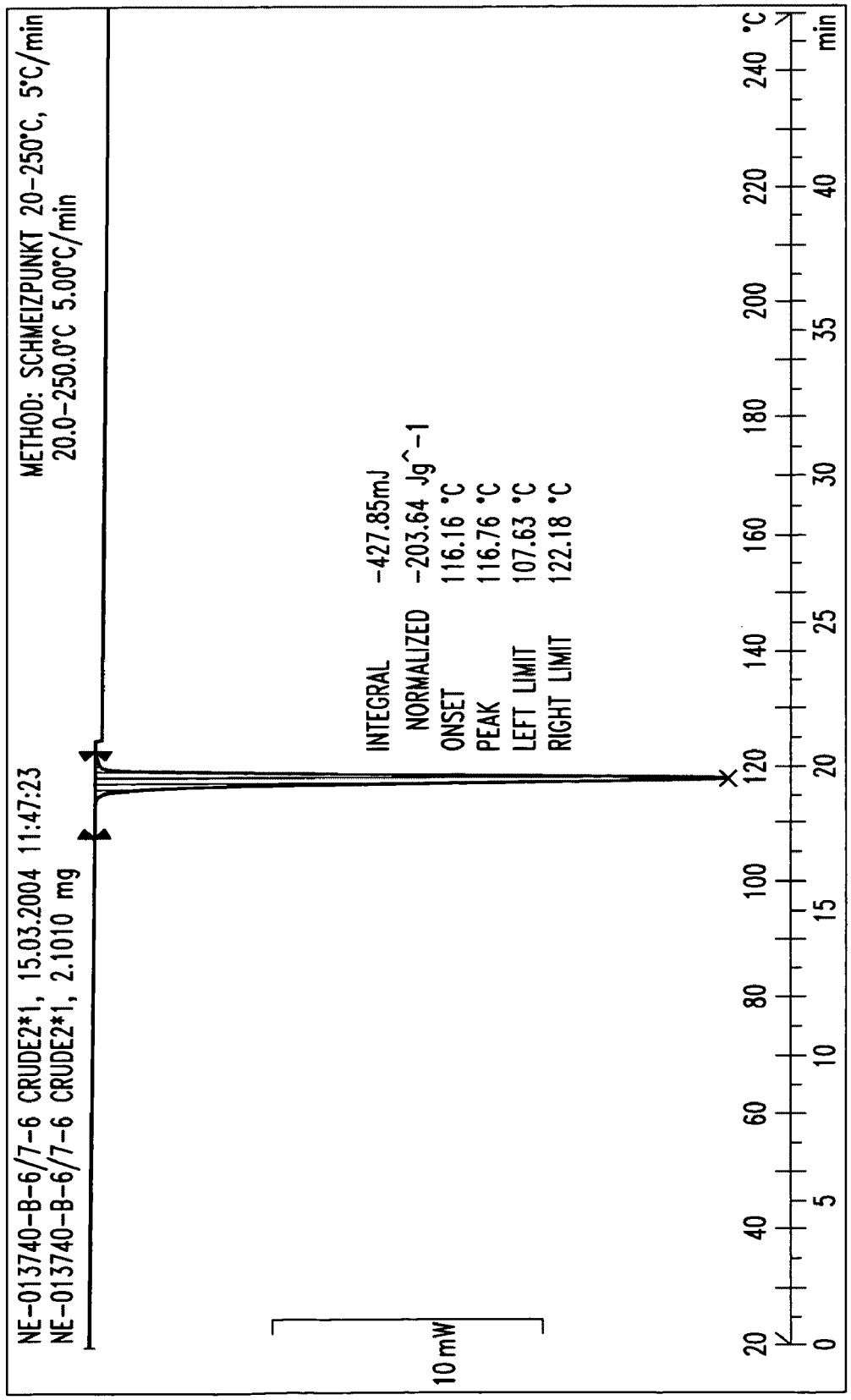
FIG. 12 shows a DSC graph of the Form II polymorph of triethylenetetramine dihydrochloride.

At least one kinetic and one thermodynamic polymorph of triethylenetetramine dihydrochloride may be formed by a process of the invention. Infrared analysis of the thermodynamic polymorph (the Form I triethylenetetramine dihydrochloride polymorph) is shown in FIG. 9. Infrared peaks are located at 825, 855, 925, 996, 1043, 1116, 1221, 1300, 1328, 1367, 1401, 1457, 1476, 1503, 1557, 1619, 1640, 2705, 2833, 2859, 2902, and 3216. DSC analysis of Form I triethylenetetramine dihydrochloride is shown in FIG. 10. Form I triethylenetetramine dihydrochloride has onset/peak melting points of 121.96/122.78° C. Infrared analysis of Form II triethylenetetramine dihydrochloride is shown in FIG. 11. Infrared peaks are located at wavenumbers 769, 807, 866, 891, 965, 989, 1039, 1116, 1158, 1205, 1237, 1352, 1377, 1395, 1438, 1456, 1519, 1610, 2102, 2419, 2468, 2533, 2611, 2667, 2743, 2954, 2986, 3050, 3157, 3276, and 3298. DSC analysis of Form II triethylenetetramine dihydrochloride has onset/peak melting points of 116.16/116.76° C., as shown in FIG. 12.

Formation of Form I triethylenetetramine dihydrochloride versus formation of Form II triethylenetetramine dihydrochloride may be mediated by altered reaction conditions including cooling rate, presence of seeding crystals, and number of equivalents of concentrated hydrochloric acid reacted with the free triethylenetetramine to form triethylenetetramine dihydrochloride. In one embodiment, mixture of one equivalent of triethylenetetramine with about 1.92 equivalents of concentrated hydrochloric acid in the presence of Form I seed crystals yields Form I triethylenetetramine dihydrochloride.

Example 9

This Example demonstrates the reduction of (3-cyanomethyl-2-phenyl-imidazolidin-1-yl)-acetonitrile (5) to intermediate 2-[3-(2-Amino-ethyl)-2-phenyl-imidazolidin-1-yl]-ethylamine (8). As shown in Scheme 9, intermediate (8) is treated with an acid to form a triethylenetetramine salt. The reduction is effected by LiAlH$_4$, the acid used is hydrochloric acid and the tetrahydrochloride salt of triethylenetetramine is produced.

Scheme 9

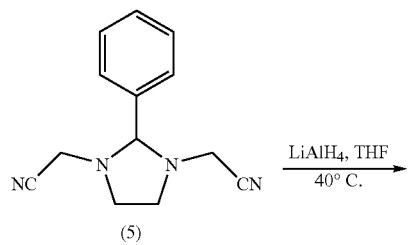

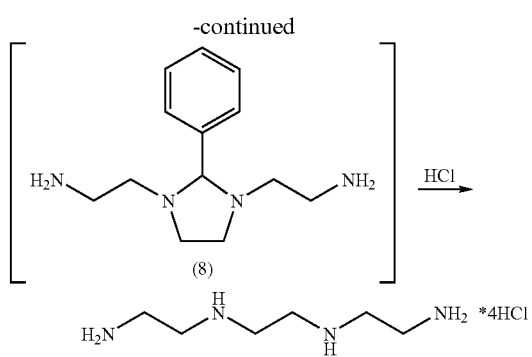

Example 10

This Example demonstrates preparation of triethylenetetramine via nitrile reduction using a Boc-protected intermediate. In the first step of the reaction potassium carbonate (101.2 g, 0.71 mol, 2.0 eq) was suspended in acetonitrile (200 mL). Ethylenediamine (21.34 g, 0.355 mol, 1.0 eq) was added. The suspension was cooled to 5-10° C. and a solution of chloroacetonitrile (57.02 g, 0.746 mol, 2.1 eq) in acetonitrile (40 mL) was added. The mixture was stirred overnight at 25° C., with care taken to prevent the reaction temperature from exceeding 35° C. Thin-layer chromatography showed almost complete conversion to the dinitrile intermediate [2-(cyanomethyl-amino)-ethylamino]-acetonitrile. The yellow suspension was cooled to 5° C. and Boc$_2$O (162.7 g, 0.746 mol, 2.1 eq) was added in portions. After one hour, thin layer chromatography showed complete conversion to Boc-protected dinitrile, [2-(tert-Butoxycarbonyl-cyanomethyl-amino)-ethyl]-cyanomethyl-carbamic acid tert-butyl ester. The suspension was filtered and the filter cake was washed with acetonitrile (800 mL). The filtrate was concentrated under reduced pressure at 40° C. The crude brown solid, [2-(tert-Butoxycarbonyl-cyanomethyl-amino)-ethyl]-cyanomethyl-carbamic acid tert-butyl ester (122.8 g, 103%), was crystallized from ethyl acetate/methylcyclohexane (180 mL/600 mL). 62.83 g of crystalline Boc-protected dinitrile [2-(tert-Butoxycarbonyl-cyanomethyl-amino)-ethyl]-cyanomethyl-carbamic acid tert-butyl ester was obtained as a white solid. The mother liquor was concentrated and again crystallized from ethyl acetate/methylcyclohexane (100 mL/180 mL). 26.07 g of crystalline product was obtained as a white solid. A third crystallization yielded 8.92 additional grams, resulting in a total yield of 81.3% of Boc-protected dinitrile [2-(tert-Butoxycarbonyl-cyanomethyl-amino)-ethyl]-cyanomethyl-carbamic acid tert-butyl ester.

The Boc-protected dinitrile was then converted to Boc-protected diamine, (2-amino-ethyl)-{2-[(2-amino-ethyl)-tert-butoxycarbonyl-amino]-ethyl}-carbamic acid tert-butyl ester. The dinitrile (13.83 g, 0.0408 mol) was dissolved in ethanol (150 mL) and NH$_3$ (25% in water) (12 mL). To the solution was added Raney nickel (12.8 g). The mixture was set under a hydrogen atmosphere (4-5 bar) for 15 hours. Thin-layer chromatography showed almost complete conversion. The mixture was filtered and the solid was washed with ethanol (350 mL). The filtrate was concentrated to dryness and the Boc-protected diamine (2-amino-ethyl)-{2-[(2-amino-ethyl)-tert-butoxycarbonyl-amino]-ethyl}-carbamic acid tert-butyl ester was obtained as 14.07 g of a white solid, a 99.5% yield.

The Boc-protected diamine (2-amino-ethyl)-{2-[(2-amino-ethyl)-tert-butoxycarbonyl-amino]-ethyl}-carbamic acid tert-butyl ester (2.83 g, 8.16 mmol) was dissolved in isopropanol (18 mL) and a mixture of concentrated HCl (5.5 mL, 48.9 mmol, 6 eq) in isopropanol (5.5 mL) was added. The mixture was heated to 70° C. for 30 minutes. The resulting suspension was cooled to 20-25° C. and filtered. The solid was washed with TBME (12 mL) and dried on a rotary evaporator. 2.16 g of triethylenetetramine tetrahydrochloride was obtained as a white solid.

Example 11

Triethylenetetramine synthesis was accomplished through the use of a [2-(cyanomethyl-amino)-ethylamino]-acetonitrile intermediate (2) prepared by reaction of ethylenediamine (1). To prevent decomposition, the [2-(cyanomethyl-amino)-ethylamino]-acetonitrile intermediate (2) was converted to a Boc-derivative (i.e., protected by tert-butoxycarbonyl groups) as shown in Scheme 10.

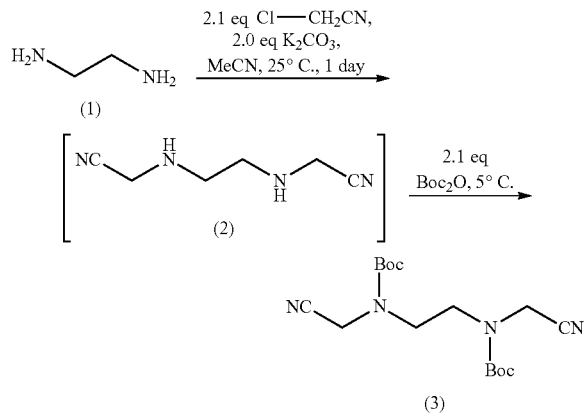

Alkylation was performed by adding a solution of 2.2 equivalents of chloroacetonitrile in acetonitrile to a mixture of 1 equivalent of ethylenediamine (1) and 2 equivalents of $K_2CO_3$ in acetonitrile over about 30 minutes at 25° C. The reaction was complete within about 21 hours. Upon complete conversion 1.2 equivalents of $Boc_2O$ were added to the reaction mixture. Thin-layer chromatography showed complete conversion to the Boc-protected intermediate (3), a [2-(tert-butoxycarbonyl-cyanomethyl-amino)-ethyl]-cyanomethyl-carbamic acid tert-butyl ester, after about 1 hour at 20° C. Work-up and crystallization from ethyl acetate/methylcyclohexane (3/10) gave Boc-protected intermediate (3) as a white solid in 81% yield.

Subsequent reaction of the Boc-protected dinitrile intermediate (3) was performed as shown in Scheme 11. A solution of the Boc-protected dinitrile intermediate (3) in aqueous ethanol/$NH_3$ was hydrogenated in the presence of Raney-nickel. A hydrogen atmosphere of 4-5 bar was used and the reaction was allowed to run for about 15 hours at 20-25° C. Work-up and concentration to dryness afforded intermediate (4), a (2-amino-ethyl)-{2-[(2-amino-ethyl)-tert-butoxycarbonyl-amino]-ethyl}-carbamic acid tert-butyl ester, in 99% yield.

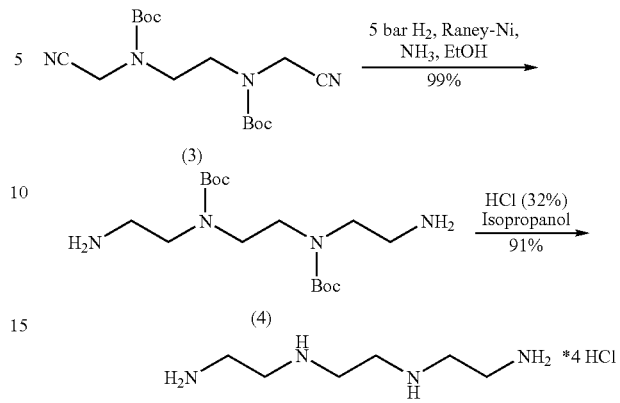

Heating a mixture of intermediate (4) and isopropanol with concentrated HCl to 70° C. for about 30 minutes cleaved the Boc-groups, as shown in Scheme 2. The tetrahydrochloride salt of triethylenetetramine was isolated by filtration in 91% yield. Presence of triethylenetetramine tetrahydrochloride salt was verified by NMR.

Example 12

This Example demonstrates the preparation of 3-cyanomethyl-2-phenyl-imidazolidin-1-yl)-acetonitrile. Equipment used included a 160 L reactor, a 50 L nutsch, and a rotary vaporator equipped with a 10 L round-bottom flask. The reactor was purged with nitrogen gas. The scrubber was charged with about 30 L of a solution of 10% NaOH. The reactor was charged with about 120.3 mol of ethylenediamine dihydrochloride, then charged with about 238.2 mol of KCN. The reactor was purged with nitrogen. The reaction was charged with about 60 L of water, and the internal temperature of the reactor dropped to about 9° C.

The reaction mixture was stirred for about 90 minutes at a maximum temperature of about 30° C., until a temperature of about 20° C. was reached, at which point the pH of the mixture was about 9.42. A 36% solution of formaldehyde in water (about 19.85 kg of the solution) was added with cooling over about 90 minutes. During the addition internal reaction temperature was maintained between about 20° C. and about 29° C. The pH of the reaction increased from about 9.12 to about 10.28. The reaction mixture was stirred for about 2.5 hours at a range of about 20° C. to about 25° C.

Within thirty minutes of completion of addition of formaldehyde, a 43.6% solution of $NaH_2PO_4$ in water (about 13.1 L of solution) was added to the reaction at an internal reaction temperature of about 10° C. to about 11° C. The pH of reaction mixture dropped from about 10.79 to about 6.22. About 31 L of n-butyl alcohol were added to the reaction mixture at an internal temperature of about 11° C. Within about thirty minutes of addition of n-butyl alcohol, about 120.3 moles of benzaldehyde were added to the reaction mixture at an internal temperature of about 11° C. to about 12° C. After about half of the benzaldehyde had been added, about 0.29 moles of 3-cyanomethyl-2-phenyl-imidazolidin-1-yl)-acetonitrile seed crystals were added. During the addition the pH dropped from about 6.22 to about 6.01. The reaction mixture was cooled to about −4° C. within about 5 hours then stirred at about −4° C. for about 8.5 hours.

The nutsch was purged with hydrogen, and the reaction mixture was filtered. The filter cake was washed with about 47 L of deionized water at about 15° C. in two portions, then washed with about 36 L of n-butyl alcohol at about −3° C. in two portions, then washed with about 36 L of isopropyl alcohol at about −2° C. in two portions. Crude (3-cyanomethyl-2-phenyl-imidazolidin-1-yl)-acetonitrile was transferred in four flasks and dried on a rotary evaporator at a temperature of about 40° C. and pressure less than or equal to about 20 mbar, producing about 6.46 kg of (3-cyanomethyl-2-phenyl-imidazolidin-1-yl)-acetonitrile at about 99.6% purity, about 8.12 kg (3-cyanomethyl-2-phenyl-imidazolidin-1-yl)-acetonitrile at about 99.2% purity, about 5.87 kg (3-cyanomethyl-2-phenyl-imidazolidin-1-yl)-acetonitrile at about 99.2% purity, and about 0.83 kg (3-cyanomethyl-2-phenyl-imidazolidin-1-yl)-acetonitrile at about 95.9% purity. All product was a white powder, and all purity measurements were conducted by gas chromatography. Total yield of (3-cyanomethyl-2-phenyl-imidazolidin-1-yl) -acetonitrile was about 21.28 kg, which was about 78.5% of maximum amount possible given the amount of starting materials used.

Example 13

This Example demonstrates the preparation of benzylidene-(2-{3-[2-(benzylidene-amino)-ethyl]-2-phenyl-imidazolidin-1-yl}-ethyl)-amine. Equipment used was the same as that used in Example 10, above.

The reactor was purged with nitrogen. The reactor was charged with about 5.00 kg of (3-cyanomethyl-2-phenyl-imidazolidin-1-yl)-acetonitrile and purged with nitrogen. About 22 L of THF was charged into the reactor, and the solution was transferred to a feeding vessel. The reactor was washed with about 13 L of THF, and that solution was also transferred to the feeding vessel.

The reactor was charged with about 46.2 kg of LiAlH$_4$ in 4% THF solution, which was cooled to an internal temperature of about 2.3° C. About 1.418 kg of methanol and about 27 L of THF were mixed in another feeding vessel, and within about 20 minutes the mixture was added to the reactor at an internal temperature of about 0 to about 22° C. The solution was then heated to an internal temperature of about 40° C.

Within about three hours the solution of (3-cyanomethyl-2-phenyl-imidazolidin-1-yl)-acetonitrile in THF was added at an internal temperature of about 40° C. A suspension was formed, and the reaction mixture was stirred at about 40° C. for about one hour. The reaction mixture was then cooled to an internal temperature of about 22° C. within about 30 minutes.

In process controls no longer detected (3-cyanomethyl-2-phenyl-imidazolidin-1-yl)-acetonitrile in solution. The reaction mixture was further cooled to about 4° C., and within about one hour about 6.9 L of a solution of 4% NaOH was added. During addition the temperature increased from about 4° C. to about 29° C. and hydrogen gas evolved. The reaction mixture was stirred at an internal temperature of about 10° C. overnight.

The nutsch was again purged with nitrogen, the suspension was filtered, and the filter cake was washed with THF. About 113 L of filtrate remained, and to this was added about 5.17 kg of benzaldehyde at 25° C. About 108 L THF was distilled from the solution at a temperature between about 13 to about 30° C., with a pressure between about 100 and 200 mbar.

About 40 L of isopropanol was added at about 40° C., and an additional 9 L of solvent was distilled off at an internal temperature between about 30 to about 37° C., under a pressure of about 90 to about 125 mbar. The reaction mixture was cooled to an internal temperature of about 3° C. within about 30 minutes. About 7 g of seed crystals of benzylidene-(2-{3-[2-(benzylidene-amino)-ethyl]-2-phenyl-imidazolidin-1-yl}-ethyl)-amine was added to the mixture at a temperature of about 30° C., and the reaction mixture was stirred at that temperature for about 30 minutes. The reaction mixture was then cooled to about −5° C. and stirred overnight.

The nutsch was again purged with nitrogen, the suspension was filtered, and the filter cake was washed with about 15 L of cold (about 0° C.) isopropanol. The product, benzylidene-(2-{3-[2-(benzylidene-amino)-ethyl]-2-phenyl -imidazolidin-1-yl}-ethyl)-amine, was dried in 2 round-bottom flasks on a rotary evaporator at a temperature of about 40° C. and a pressure less than or equal to 20 mbar. Flask 1 gave about 2.864 kg of benzylidene-(2-{3-[2-(benzylidene-amino)-ethyl]-2-phenyl-imidazolidin-1-yl}-ethyl)-amine as an off-white solid with a purity of about 99.06 area % by gas chromatography. Flask 2 gave about 3.195 kg of benzylidene-(2-{3-[2-(benzylidene-amino)-ethyl]-2-phenyl -imidazolidin-1-yl}-ethyl)-amine as an off-white solid with a purity of about 99.24 area % by gas chromatography. Total yield of benzylidene-(2-{3-[2-(benzylidene-amino)-ethyl]-2-phenyl -imidazolidin-1-yl}-ethyl)-amine based on starting materials was about 66.9%.

Example 14

This Example describes the preparation of triethylenetetramine disuccinate. Reaction equipment was the same as that used in Examples 12 and 13, above.

The reactor was purged with nitrogen. About 2.51 kg of benzylidene-(2-{3-[2-(benzylidene-amino)-ethyl]-2-phenyl-imidazolidin-1-yl}-ethyl)-amine and about 2.89 kg of succinic acid were added to a reactor. The reactor was again purged with nitrogen. About 13 L of water were added to the reactor, and the mixture was heated to about 60° C. and stirred for about 5 minutes. The mixture was cooled to about 20° C. About 13 L of tert-butylmethylether were added to the reaction mixture and stirred for about 5 minutes, forming a biphasic mixture, with benzaldehyde in the organic phase. The phases were separated and the organic layer discarded.

About 63 L of isopropanol were added to the aqueous phase at an internal temperature of about 20° C. within about 20 minutes. After about 25 L had been added, about 8 g of triethylenetetramine disuccinate seed crystals were added and addition of isopropanol continued. The reaction mixture was stirred at about 20° C. for about 70 minutes, and an about 13 L of isopropanol were added to the mixture.

The reaction mixture was cooled to about 0° C. to facilitate crystallization and stirred overnight. Triethylenetetramine disuccinate precipitated from the isopropanol solution. The nutsch was purged with nitrogen, and the suspension was filtered. The filter cake was washed with about 13 L of isopropanol. The product was then washed with about 6 L of tert -butylmethylether, then dried on a rotary vaporator at a temperature of about 40° C. and a pressure less than or equal to about 20 mbar.

The product, triethylenetetramine disuccinate, was an off-white solid produced in an amount of about 2.098 kg, with a purity of about 100 area % by gas chromatography. Yield was about 89.9%.

Example 15

This Example describes an additional preparation of triethylenetetramine disuccinate. Reaction equipment was the same as that used in Examples 12, 13, and 14, above.

The reactor was purged with nitrogen. About 2.65 kg of benzylidene-(2-{3-[2-(benzylidene-amino)-ethyl]-2-phenylimidazolidin-1-yl}-ethyl)-amine and about 3.05 kg of succinic acid were added to a reactor. The reactor was again purged with nitrogen. About 13 L of water were added to the reactor, and the mixture was heated to about 59° C. and stirred for about 5 minutes. The mixture was cooled to about 20° C. About 13 L of tert-butylmethylether were added to the reaction mixture and stirred for about 13 minutes, forming a biphasic mixture, with benzaldehyde in the organic phase. The phases were separated and the organic layer discarded.

About 66 L of isopropanol were added to the aqueous phase at an internal temperature of about 20° C. within about 21 minutes. After about 25 L had been added, about 9 g of triethylenetetramine disuccinate seed crystals were added and addition of isopropanol continued. The reaction mixture was stirred at about 19 to 22° C. for about 65 minutes, and an about 13 L of isopropanol was added to the mixture.

The reaction mixture was cooled to about 5° C. to facilitate crystallization and stirred overnight. Triethylenetetramine disuccinate precipitated from the isopropanol solution. The nutsch was purged with nitrogen, and the suspension was filtered. The filter cake was washed with about 14 L of isopropanol. The product was washed with about 7 L of tert-butylmethylether, then dried on a rotary vaporator at a temperature of about 40° C. and a pressure less than or equal to about 20 mbar.

The product, triethylenetetramine disuccinate, was an off-white solid produced in an amount of about 2.266 kg, with a purity of about 100 area % by gas chromatography. Yield was about 91.7%.

Example 16

This Example describes a further additional preparation of triethylenetetramine disuccinate. Reaction equipment was the same as that used in Examples 10, 11, 12, and 13 above.

1 equal mole of benzylidene-(2-{3-[2-(benzylidene-amino)-ethyl]-2-phenyl -imidazolidin-1-yl}-ethyl)-amine was added to the reactor, which was purged before and after with nitrogen. Isopropanol was added to the reactor, followed by the addition of water. The reaction mixture was then heated to 40° C. and then transferred into a second reactor via an inline -filter. 4 equal moles of succinic acid was added to the first reactor which was then purged with nitrogen, followed by addition of methanol and stirring for 40 minutes or until a clear solution was obtained. The succinic acid solution was then transferred to the second reactor via the inline-filter, at the same time of transferal the same volume of methanol added was distilled off at ET=50° C., p=>100 mbar and internal temperature (IT)=22-28° C. The mixture in the second reactor is stirred for about one hour at 40° C., cooled to IT=0° C. and then stirred overnight at this same temperature. The resultant suspension was filtered and isopropanol added through the inline filter, followed by the addition of tert-butyl methyl ether (TBME) via the inline-filter. The resultant triethylenetetramine disuccinate was then dried in a PROVATECH -dryer (ET=40° C., p≦20 mbar) in two portions.

The triethylenetetramine disuccinate was then re-crystallized to remove benzaldehyde. Dried disuccinate salt was placed back into the reactor, purged with nitrogen and water added and heated to IT=50° C. Methanol was inline-filtered and added to the reaction mixture followed by water. The mixture was then heated to IT=55° C. at which point a clear solution was obtained. Methanol was inline-filtered and added to the reaction mixture over 25 minutes at IT=55° C. and then cooled to 0° C. for 30 minutes. The resultant suspension was filtered and methanol was inline-filtered to the reactor. The resultant triethylenetetramine disuccinate was dried in the PROVATECH-dryer (ET=40° C., p≦20 mbar). This resulted in a white to off white solid, purity of 98.84 area % (Ion Chromatography) with a yield of 93.1%.

Example 17

This Example describes the preparation of triethylenetetramine tetrahydrochloride by a process of the invention. Reaction equipment was similar to that used in Example 15.

The reactor was purged with nitrogen and charged with about 9.46 kg of benzylidene-(2-{3-[2-(benzylidene-amino)-ethyl]-2-phenyl -imidazolidin-1-yl}-ethyl)-amine. The reactor was again purged with nitrogen, and about 15 L of water were introduced to the reactor. About 14.5 L of a 32% solution of HCl were added to the aqueous suspension with cooling between temperatures of about 17 to about 20° C. within 26 minutes.

The reaction mixture was cooled at about 17° C. for about fifteen minutes, until a clear solution was obtained. About 30 L of tert-butylmethyl ether were added to the reactor at a temperature of about 20° C., and the mixture was stirred at about that temperature for about 10 minutes. A biphasic mixture was formed. The organic layer was discarded.

Within 1.5 hours about 89 L of isopropanol were added to the aqueous solution at about 18-22° C. The suspension was stirred at about 23° C. for about 15 minutes. The nutsch was purged with nitrogen and the suspension was filtered. The filter cake was washed with about 30 L of isopropanol, washed with about 30 L of tert-butylmethyl ether, and again washed with about 30 L of tert-butylmethyl ether. The cake was dried on a rotary evaporator at about 40° C., at a pressure less than or equal to about 20 mbar in three lots.

Triethylenetetramine tetrahydrochloride was produced. In Flask 1, about 2.19 kg of an off-white solid with a purity of about 98.5 area % by gas chromatography and about 100.0% by chloride titration assay was obtained. In Flask 2, about 1.94 kg of an off-white solid with a purity of about 98.2 area % by gas chromatography and about 99.9% by chloride titration assay was obtained. In Flask 3, about 2.08 kg of an off-white solid with a purity of about 98.3 area % by gas chromatography and about 102.9% by chloride titration assay was obtained. This corresponded to a total yield of about 92.3%.

Example 18

This Example describes the preparation of triethylenetetramine dihydrochloride by a process of the invention. Equipment used was the same as that in Example 16.

The reactor was purged with nitrogen and charged with about 6.00 kg of triethylenetetramine tetrahydrochloride. The reactor was purged again with nitrogen, then about 60 L of ethanol were added. About 14.56 kg of NaOMe (about 30.5% in methanol) were diluted with about 25 L of ethanol. The diluted solution was added to the suspension in the reactor vessel at a temperature of about 19 to about 22° C. within 10 minutes. The feeding vessel of the NaOMe solution was washed with about 4.8 L of ethanol into the reactor.

The suspension was stirred at about 20° C. for about 11 minutes. About 24 L of tert-butylmethyl ether were charged into the reactor, and the suspension was stirred at about 20° C. for about three hours. The suspension was filtered. The filter cake was washed with about 24 L of a mixture of tert-butyl-methyl ether and ethanol. The filtrate was concentrated in the reactor vessel by distillation of about 130 L of solvent at about 19 to about 22° C., with a pressure of about 47 to about 120 mbar.

The reactor was charged with about 30 L of tert-butylmethyl ether. The mixture was stirred at about 23° C. for about 15 minutes. The suspension was filtered, and the filter cake was washed with about 6 liters of tert-butylmethyl ether. The filtrate was filtered into the reactor vessel through an inline filter, and the inline filter was rinsed with about 5 L of tert-butylmethyl ether. The filtrate was concentrated in the reactor vessel by distillation of about 32 L of solvent at an internal temperature of about 17 to 24° C. and a pressure of about 45 to 170 mbar.

The solution was cooled to about 20° C. within about 7 minutes. About 20 L of ethanol were added through an inline filter, and the solution was cooled to an internal temperature of about 0° C. within about 16 minutes. About 4.46 kg of HCl was added, with cooling, through an inline filter at an internal temperature of between about 0 and 15° C. within about 30 minutes.

The suspension was stirred at an internal temperature of about 15 to about 22° C. for about 10 minutes, then heated to about 48° C. for about 1 hour until a clear solution was obtained. About 133 L of ethanol were added through an inline filter. About 10 g of seed crystals of a thermodynamic polymorph of triethylenetetramine dihydrochloride were added at an internal temperature of about 32° C. The reaction mixture was stirred for about thirty minutes at about 29 to about 32° C. until a suspension formed. The suspension was cooled to an internal temperature of about 3° C. within 5 hours, then stirred at about 3° C. for about 11 hours. The nutsch was purged with nitrogen, and the suspension was filtered.

The filter cake was washed with about 15 L of ethanol, then washed with about 15 L of tert-butylmethyl ether. The filter was dried on a rotary vaporator at a temperature of about 40° C. and a pressure less than or equal to about 20 mbar. About 3.62 kg of triethylenetetramine dihydrochloride was obtained as a yellowish solid with a purity of about 100 area % by TLC. This corresponded to a yield of about 80.4%.

Example 19

This Example illustrates, triethylenetetramine tetramaleate, triethylenetetramine tetrafumarate and triethylenetetramine disuccinate, the synthesis of these salts according to the synthetic schemes described above. Crystals of X-ray quality for triethylenetetramine tetramaleate were grown by slow evaporation of a supersaturated solution of triethylenetetramine tetramaleate in water. The triethylenetetramine disuccinate and triethylenetetramine tetrafumarate were grown by slow evaporation of a solution of 12.58 mg triethylenetetramine disuccinate and 7.42 mg triethylenetetramine tetrafumarate in a water/ethanol mixture (1:1, 2 ml) over a period of 3 weeks. Crystal structure data (Tables 3-5) was obtained by single crystal x-ray diffraction measurement. For comparison, x-ray powder diffraction measurements were done with the accordant powder material.

Figure 13:
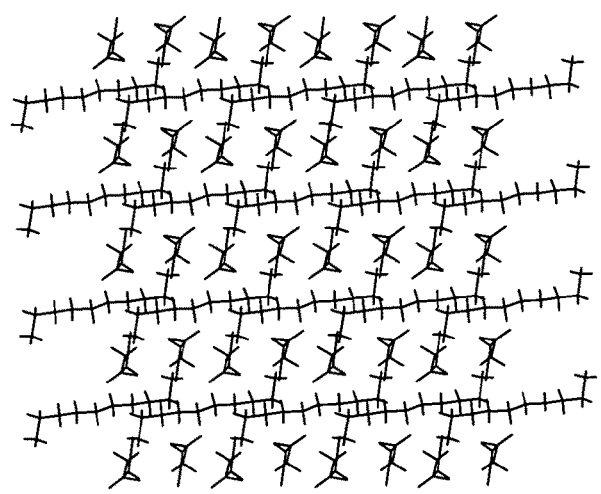
FIG. 13 shows a 2×2×2 unit cell of triethylenetetramine disuccinate with a view along (I) [010], (II) [100] and (III) [001].
Figure 13:
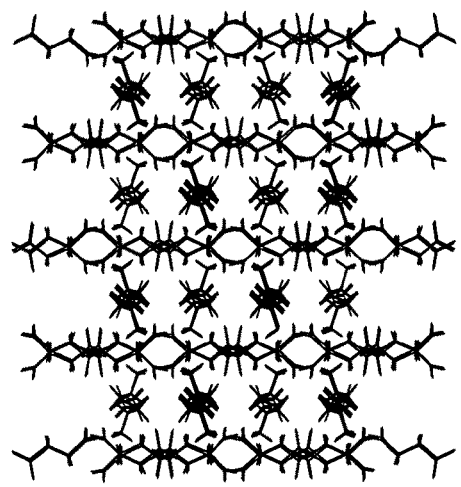
Figure 13:
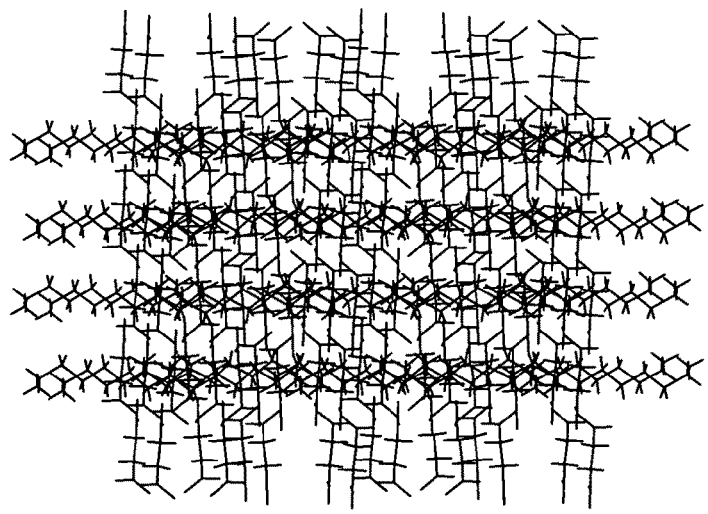
Figure 14:
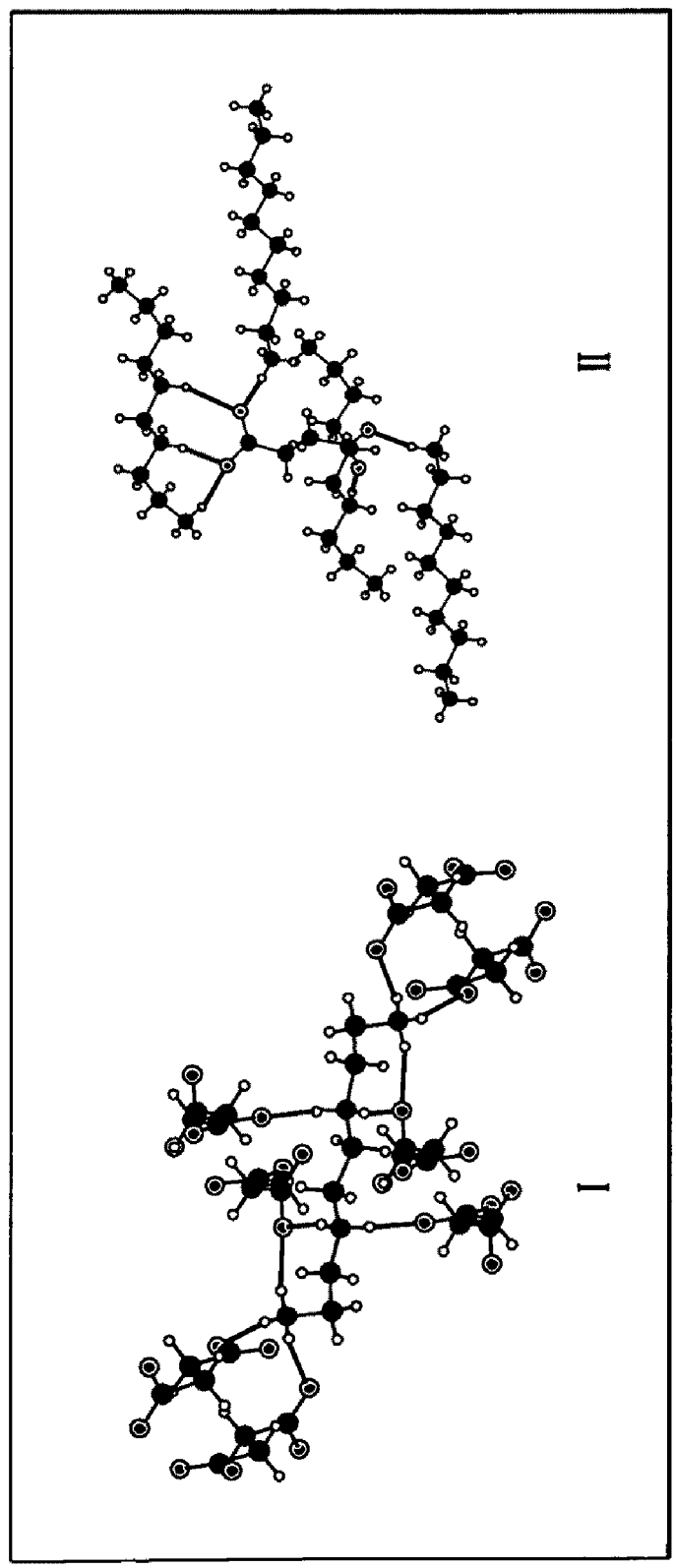
FIG. 14 shows a coordination sphere for (I) triethylenetetramine and (II) triethylenetetramine disuccinate.
Figure 15:
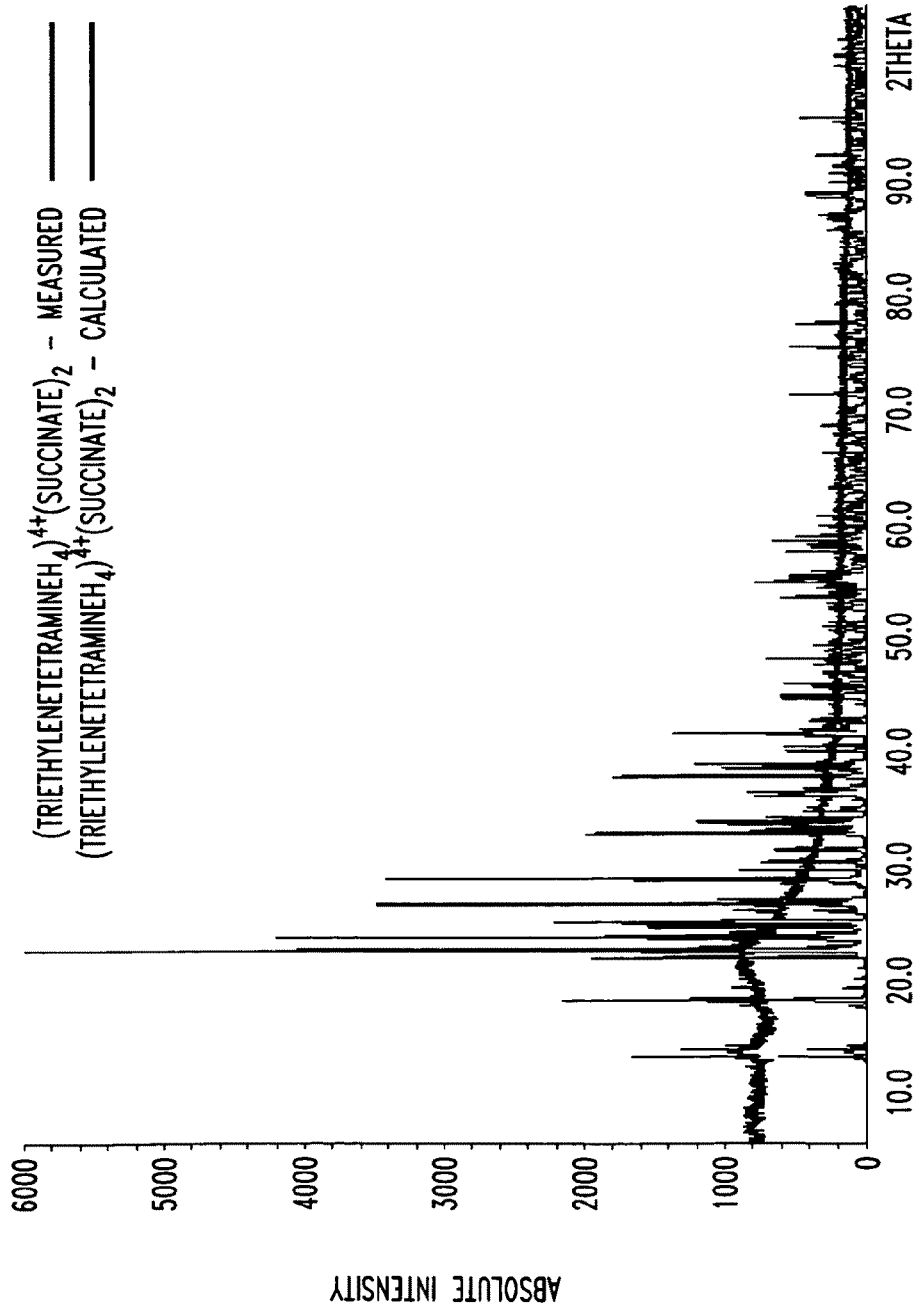
FIG. 15 shows an X-ray powder pattern of the triethylenetetramine disuccinate powder material in comparison with the calculated powder pattern obtained from the single crystal structure data for triethylenetetramine disuccinate.
Figure 16:
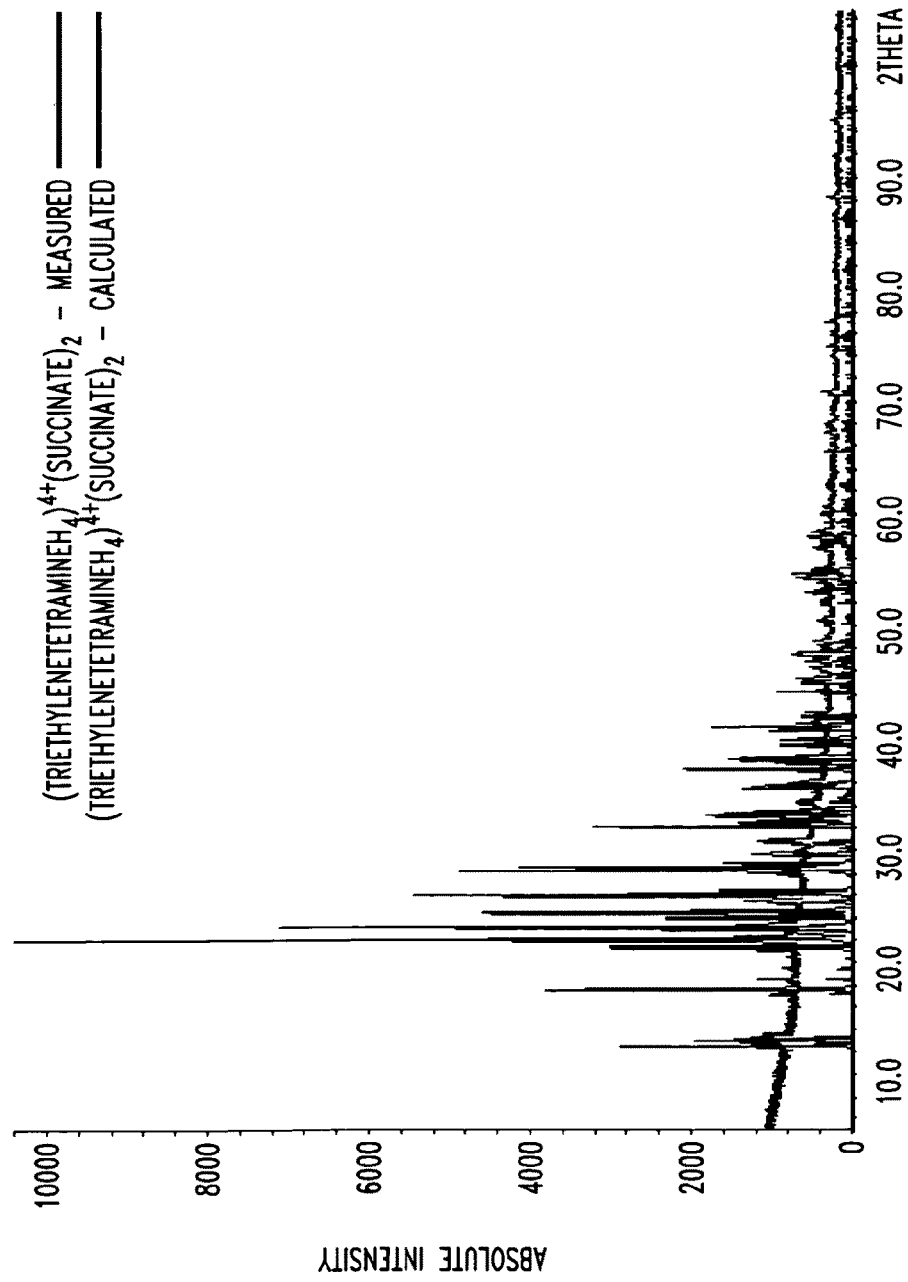
FIG. 16 shows an X-ray powder pattern of the re-crystallised triethylenetetramine disuccinate powder material in comparison with the calculated powder pattern obtained from the single crystal structure data for triethylenetetramine disuccinate.

FIG. 13 shows a crystal structure of triethylenetetramine disuccinate anhydrate. Based on the resolved structure, the composition ratio of triethylenetetramine:succinate was confirmed to be 1:2. The triethylenetetramine and the succinate molecules formed alternating layers which interact via strong hydrogen bonds. The positively charged triethylenetetramines do not interact with each other. FIG. 14 shows the triethylenetetramine molecule surrounded by eight succinate molecules. Six of these succinate molecules formed one very strong hydrogen bond between one of the negatively charged O-atoms and the H-atom of the protonated NH— or $NH_2$-groups. The other two succinate molecules formed two hydrogen bonds between their negatively charged O-atom and an H-atom of a protonated NH-group and another H-atom of the protonated $NH_2$-group. Water molecules are not necessary to complete the coordination sphere of the triethylenetetramine molecule. Each succinate molecule is coordinated via six hydrogen bonds to four triethylenetetramine molecules (FIG. 14 II). FIGS. 15 and 16 represent two X-ray powder diffraction patterns obtained from independently synthesized triethylenetetramine disuccinate powder material. Crystal quality may be enhanced by an additional recrystallisation.

TABLE 3A

Crystallographic and refinement data for triethylenetetramine disuccinate

| | |
|---|---|
| formula sum | $C_{14}H_{34}N_4O_8$ |
| formula weight | 386.44 |
| measurement temperature | 84(2) K |
| measurement device | Bruker SMART CCD |
| wavelength | 0.71076 Å (Mo-K☐-radiation) |
| crystal system | monoclinic |
| space group | C 2/c (no. 15) |
| unit cell dimensions | a = 14.059(5) Å |
| | b = 9.169(5) Å |
| | c = 13.647(5) Å |
| | β = 92.47(0)° |
| cell volume | 1757.56(130) Å$^3$ |
| Z | 4 |
| density, calculated | 1.007 g/cm$^3$ |
| $R_{All}$ | 0.043 |
| absorption coefficient ☐ | 0.077 mm$^{-1}$ |
| F(000) | 584 |
| ☐ range | 2.65-25.66° |
| $h_{min}$, $h_{max}$; $k_{min}$, $k_{max}$; $l_{min}$, $l_{max}$ | −17, 16; −6, 11; −14, 16 |
| reflections measured | 4899 [R(int) = 0.0322] |
| independent reflections | 1653 |
| observed reflections [I > 2s(i)] | 1455 |
| data/restraints/parameters | 1653/0/118 |
| Goodness-of-fit at F$^2$ | 1.053 |
| R indices [I > 2 sigma(I)] | R1 = 0.0366, wR2 = 0.0948 |
| R indices (all data) | R1 = 0.0431, wR2 = 0.0987 |
| largest diff. peak/hole | 0.266/−0.260 e · A$^{-3}$ |

TABLE 3B

Triethylenetetramine disuccinate atomic coordinates and isotropic displacement parameters (in Å$^2$)

| | x | y | z | $U_{eq}$ |
|---|---|---|---|---|
| C1 | 0.29558(10) | 0.26210(16) | 0.31932(10) | 0.0126(3) |
| H1A | 0.25420 | 0.34680 | 0.31880 | 0.01500 |
| H1B | 0.27720 | 0.19900 | 0.37230 | 0.01500 |
| C2 | 0.2803(1) | 0.18094(16) | 0.22253(10) | 0.0122(3) |
| H2A | 0.33450 | 0.11790 | 0.21290 | 0.01500 |
| H2B | 0.22430 | 0.11980 | 0.22590 | 0.01500 |
| C3 | 0.2663(1) | 0.19924(16) | 0.04178(9) | 0.0124(3) |
| H3A | 0.22310 | 0.11710 | 0.04510 | 0.01500 |
| H3B | 0.32940 | 0.16200 | 0.03010 | 0.01500 |
| C4 | 0.0209(1) | 0.46728(16) | 0.12805(9) | 0.0113(3) |
| C5 | −0.0467(1) | 0.33720(16) | 0.11701(10) | 0.0129(3) |
| H5A | −0.08810 | 0.35300 | 0.05930 | 0.01500 |
| H5B | −0.08650 | 0.33540 | 0.17330 | 0.01500 |
| C6 | −0.00004(10) | 0.18713(16) | 0.10792(10) | 0.0134(3) |
| H6A | 0.04010 | 0.18650 | 0.05180 | 0.01600 |
| H6B | 0.03980 | 0.16740 | 0.16620 | 0.01600 |
| C7 | −0.07602(10) | 0.06870(16) | 0.09545(10) | 0.0114(3) |
| N1 | 0.39566(8) | 0.31058(14) | 0.33899(8) | 0.0117(3) |
| H1C | 0.40020 | 0.35710 | 0.39620 | 0.01800 |
| H1D | 0.41260 | 0.37040 | 0.29140 | 0.01800 |
| H1E | 0.43390 | 0.23320 | 0.34110 | 0.01800 |
| N2 | 0.26795(8) | 0.28179(14) | 0.13633(8) | 0.0109(3) |
| H2C | 0.21310 | 0.33160 | 0.14060 | 0.01300 |
| H2D | 0.31610 | 0.34660 | 0.13740 | 0.01300 |
| O1 | −0.01814(7) | 0.59176(11) | 0.12409(7) | 0.0154(3) |
| O2 | 0.10919(7) | 0.44737(11) | 0.14249(7) | 0.0153(3) |

TABLE 3B-continued

Triethylenetetramine disuccinate atomic coordinates and isotropic displacement parameters (in Å²)

|    | x | y | z | $U_{eq}$ |
|----|---|---|---|---|
| O3 | −0.12598(8) | 0.06534(12) | 0.01693(7) | 0.0188(3) |
| O4 | −0.08767(7) | −0.01952(12) | 0.16553(7) | 0.0178(3) |

TABLE 3C

Triethylenetetramine disuccinate anisotropic displacement parameters (in Å²)

|    | $U_{11}$ | $U_{22}$ | $U_{33}$ | $U_{12}$ | $U_{13}$ | $U_{23}$ |
|----|---|---|---|---|---|---|
| C1 | 0.0120(7) | 0.0130(8) | 0.0129(7) | 0.0010(6) | 0.0011(5) | 0.0010(6) |
| C2 | 0.0135(7) | 0.0099(7) | 0.0130(7) | −0.0003(5) | −0.0007(5) | 0.0017(5) |
| C3 | 0.0133(7) | 0.0113(7) | 0.0125(7) | 0.0000(5) | −0.0007(5) | −0.0024(6) |
| C4 | 0.0132(7) | 0.0121(8) | 0.0087(6) | 0.0002(6) | 0.0016(5) | −0.0012(5) |
| C5 | 0.0106(7) | 0.0123(8) | 0.0158(7) | −0.0010(6) | 0.0007(5) | −0.0002(5) |
| C6 | 0.0125(7) | 0.0122(8) | 0.0154(7) | −0.0013(6) | 0.0011(5) | 0.0006(5) |
| C7 | 0.0128(7) | 0.0092(7) | 0.0123(6) | 0.0019(5) | 0.0018(5) | −0.0011(5) |
| N1 | 0.0136(6) | 0.0111(6) | 0.0104(5) | 0.0010(5) | −0.0008(4) | −0.0006(4) |
| N2 | 0.0108(6) | 0.0103(6) | 0.0115(6) | −0.0003(5) | −0.0005(4) | 0.0000(5) |
| O1 | 0.0139(5) | 0.0106(6) | 0.0216(5) | 0.0007(4) | −0.0008(4) | −0.0026(4) |
| O2 | 0.0107(5) | 0.0131(6) | 0.0219(5) | 0.0001(4) | 0.0001(4) | −0.0026(4) |
| O3 | 0.0241(6) | 0.0185(6) | 0.0132(5) | −0.0079(4) | −0.0044(4) | 0.0033(4) |
| O4 | 0.0206(6) | 0.0174(6) | 0.0150(5) | −0.0066(4) | −0.0032(4) | 0.0055(4) |

Example 20

Figure 17:
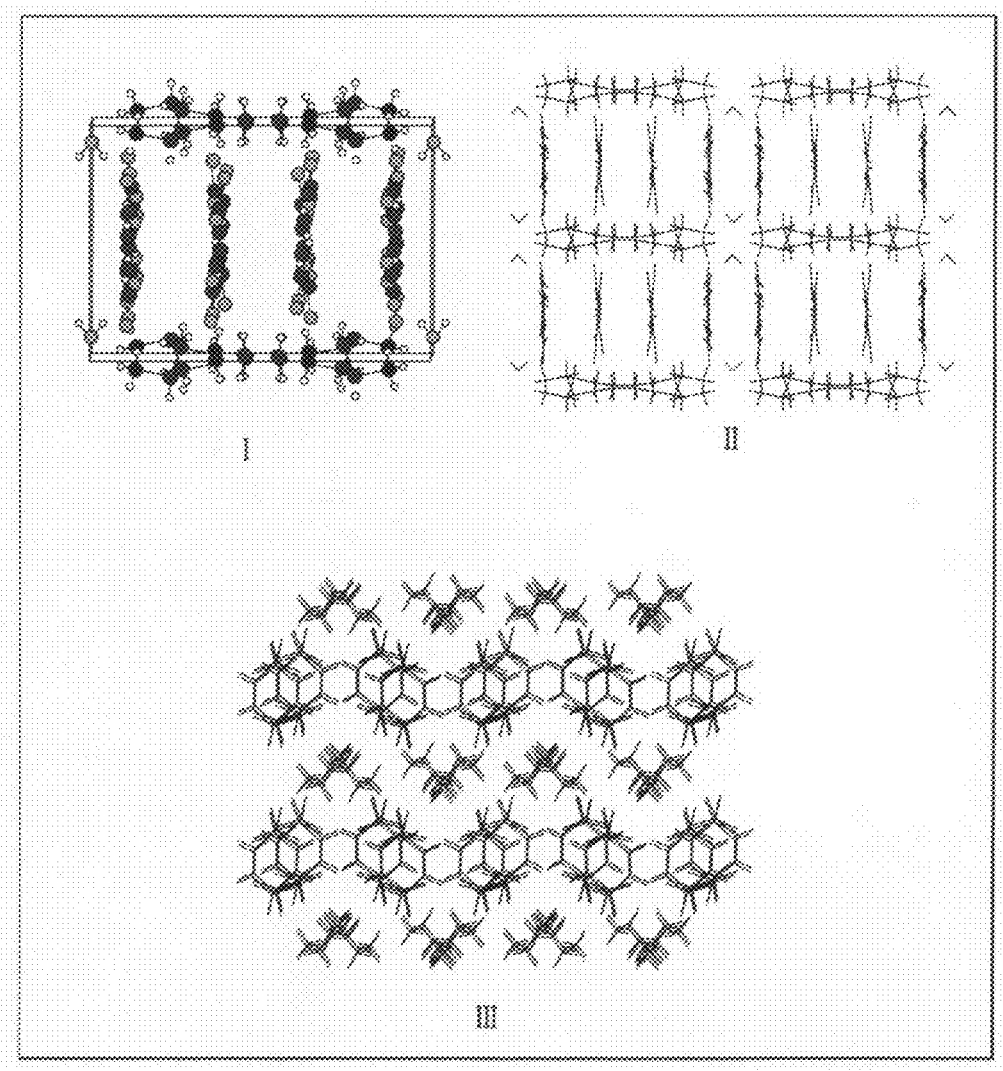
FIG. 17 shows (I) a unit cell of triethylenetetramine tetramaleate and (II) 2×2×2 unit cells of triethylenetetramine tetramaleate with view along [010], and (III) 2×2×2 unit cells of triethylenetetramine tetramaleate with view along [100].
Figure 18:
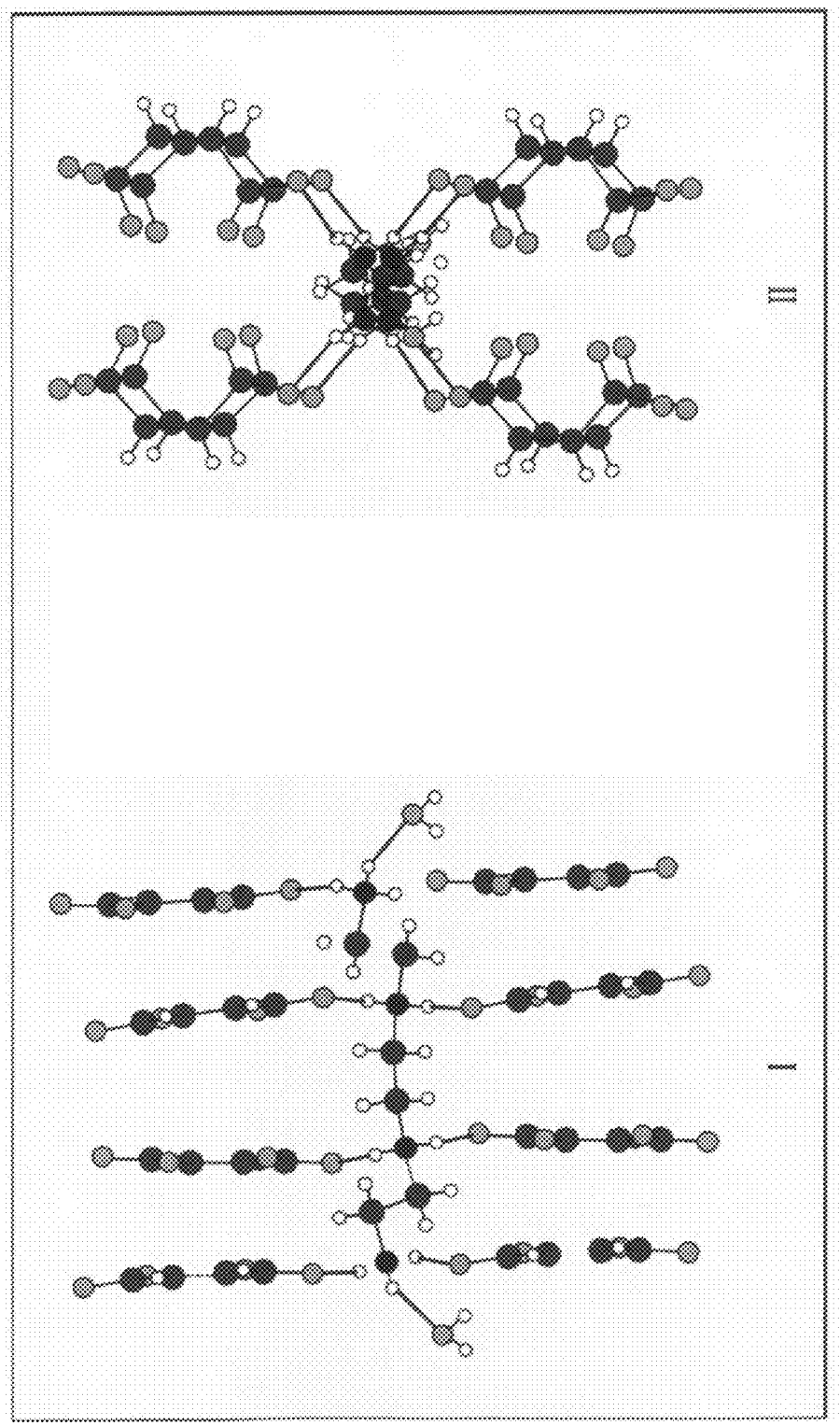
FIG. 18 shows the coordination sphere of triethylenetetramine tetramaleate with view along (I) [001] and (II) [110].
Figure 19:
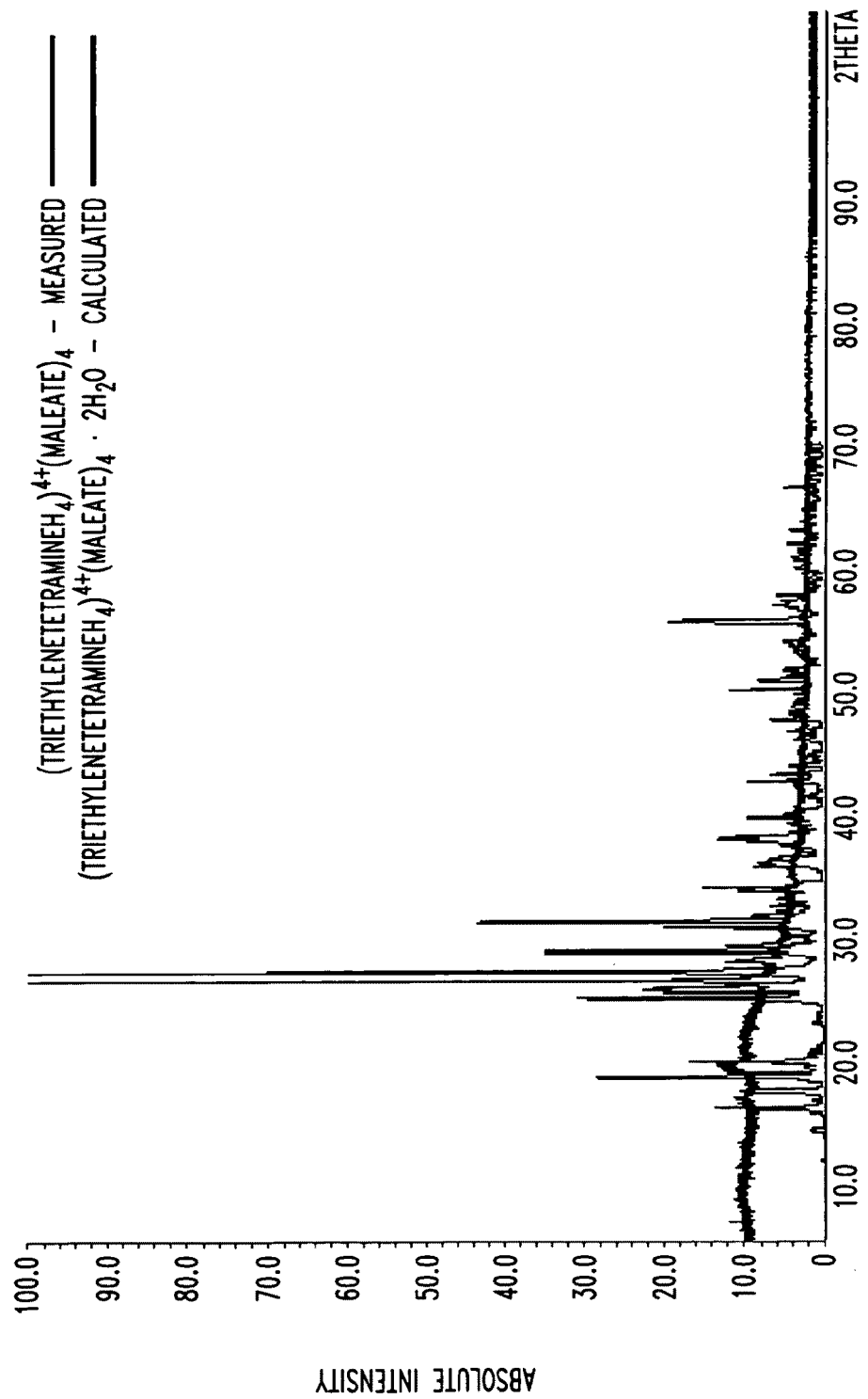
FIG. 19 shows the X-ray powder pattern of the triethylenetetramine tetramaleate powder in comparison with the calculated powder pattern obtained from the single crystal structure data for triethylenetetramine tetramaleate. $2H_2O$.

FIG. 17 shows a crystal structure with the composition of triethylenetetramine tetramaleate.2H₂O obtained from triethylenetetramine tetramaleate. X-ray diffraction measurements of the crystals confirmed the 1:4 ratio of triethylenetetramine:maleate present in the crystal based on the analysis of the powder material. FIG. 18 shows that the obtained crystal structure is characterized by a layer structure which contained alternating layers of triethylenetetramine and maleate molecules. FIG. 18 shows that the triethylenetetramine molecule is surrounded by eight maleate and two water molecules. Each maleate molecule possesses a mono negative charge and forms a strong hydrogen bond between the negatively charged O-atom of the maleate and the H-atom of the protonated NH— or NH₂-groups. The H-atom of the COOH-group of the maleate molecule also forms hydrogen bonds to another triethylenetetramine molecule, with slightly longer bond distances. Each H-atom of the protonated NH— or NH₂-groups forms a hydrogen bond to the O-atom of one maleate molecule, except for one H-atom of each $NH_3^+$-group at each end of the molecule, which form a hydrogen bond to an additional water molecule. Thus, these two water molecules complete the coordination sphere of the $NH_3^+$-groups of the triethylenetetramine molecule. As seen in FIG. 18, the triethylenetetramine molecules are only connected to each other via the additional water molecules (see FIG. 18, II) within the layers. Triethylenetetramine and maleate are connected via the hydrogen bonds described above. Inside the layer of the maleate there is no significant interaction between the molecules. FIG. 19 represents an x-ray powder diffraction pattern obtained from a synthesized triethylenetetramine. Crystal quality may be enhanced by an additional recrystallisation.

TABLE 4A

Crystallographic and refinement data for triethylenetetramine tetramaleate dihydrate

| | |
|---|---|
| formula sum | $C_{22}H_{38}N_4O_{18}$ |
| formula weight | 645.56 |
| measurement temperature | 83 K |
| measurement device | Bruker SMART CCD |
| wavelength | 0.71069 Å (Mo-K□-radiation) |
| crystal system | monoclinic |
| space group | P 2/c (no. 13) |
| unit cell dimensions | a = 13.261(5) Å |
| | b = 9.342(5) Å |
| | c = 11.266(5) Å |
| | β = 91.01(0)° |
| cell volume | 1395.46(110) Å³ |
| Z | 4 |
| density, calculated | 1.229 g/cm³ |
| $R_{All}$ | 0.047 |
| absorption coefficient □ | 0.130 mm⁻¹ |
| F(000) | 664 |
| □ range | 1.54-26.41° |
| $h_{min}, h_{max}; k_{min}, k_{max}; l_{min}, l_{max}$ | −16, 16; −8, 11; −14, 14 |
| reflections measured | 8095 [R(int) = 0.0198] |
| independent reflections | 2860 |
| observed reflections [I > 2s(i)] | 2457 |
| data/restraints/parameters | 2860/0/224 |
| Goodness-of-fit at F² | 1.103 |
| R indices [I > 2 sigma(I)] | R1 = 0.0937, wR2 = 0.0375 |
| R indices (all data) | R1 = 0.0998, wR2 = 0.0475 |
| largest diff. peak/hole | 0.279/−0.217 e · A⁻³ |

TABLE 4B

Triethylenetetramine tetramaleate atomic coordinates and isotropic displacement parameters (in Å²)

|     | x | y | z | $U_{eq}$ |
|-----|---|---|---|---|
| C1  | −0.1177(1) | 0.3688(2) | 0.0564(1) | 0.0176(3) |
| C2  | −0.1132(1) | 0.4687(2) | 0.1600(1) | 0.0209(3) |
| H2  | −0.1111 | 0.4243 | 0.2339 | 0.02500 |
| H2A | 0.1153 | −0.1147 | 0.0547 | 0.02900 |
| H2B | 0.1366 | 0.0378 | 0.0565 | 0.02900 |
| H2C | 0.0887 | −0.0293 | 0.1573 | 0.02900 |
| C3  | −0.1116(1) | 0.6113(2) | 0.1633(1) | 0.0208(3) |
| H3  | −0.1067 | 0.6502 | 0.2391 | 0.02500 |
| C4  | −0.1166(1) | 0.7188(2) | 0.0656(1) | 0.0203(3) |

TABLE 4B-continued

Triethylenetetramine tetramaleate atomic coordinates and isotropic displacement parameters (in Å²)

|      | x          | y           | z           | $U_{eq}$  |
|------|------------|-------------|-------------|-----------|
| C5   | 0.6193(1)  | 0.6463(2)   | 0.5558(1)   | 0.0178(3) |
| C6   | 0.6208(1)  | 0.5439(2)   | 0.4540(1)   | 0.0187(3) |
| H6   | 0.6160     | 0.5861      | 0.3794      | 0.02200   |
| C7   | 0.6279(1)  | 0.4015(2)   | 0.4531(1)   | 0.0191(3) |
| H7   | 0.6272     | 0.3604      | 0.3779      | 0.02300   |
| C8   | 0.6368(1)  | 0.2971(2)   | 0.5531(1)   | 0.0180(3) |
| C9   | 0.2656(1)  | 0.0548(2)   | 0.2328(1)   | 0.0173(3) |
| H9A  | 0.2704     | 0.1405      | 0.1846      | 0.02100   |
| H9B  | 0.2145     | 0.0712      | 0.2920      | 0.02100   |
| C10  | 0.2343(1)  | −0.0703(2)  | 0.1549(1)   | 0.0178(3) |
| H10A | 0.2834     | −0.0843     | 0.0932      | 0.02100   |
| H10B | 0.2316     | −0.1570     | 0.2022      | 0.02100   |
| C11  | 0.4516(1)  | 0.0112(2)   | 0.2127(1)   | 0.0180(3) |
| H11  | 0.4417(12) | −0.0783(18) | 0.1690(14)  | 0.016(4)  |
| H12  | 0.4482(12) | 0.0925(18)  | 0.1592(15)  | 0.018(4)  |
| H13  | −0.0348(16)| 0.158(2)    | 0.2007(18)  | 0.049(6)  |
| H14  | −0.1340(19)| 0.550(3)    | −0.047(2)   | 0.071(8)  |
| H15  | 0.6350(18) | 0.477(3)    | 0.668(2)    | 0.066(8)  |
| H16  | 0.3586(12) | −0.0514(19) | 0.3391(15)  | 0.019(4)  |
| H17  | 0.3759(13) | 0.108(2)    | 0.3430(16)  | 0.026(4)  |
| N1   | 0.3645(1)  | 0.0276(1)   | 0.2934(1)   | 0.0157(3) |
| N2   | 0.1336(1)  | −0.0412(1)  | 0.1004(1)   | 0.0191(3) |
| O1   | −0.1086(1) | 0.2382(1)   | 0.0779(1)   | 0.0220(2) |
| O2   | −0.1305(1) | 0.4170(1)   | −0.0485(1)  | 0.0240(3) |
| O3   | −0.1077(1) | 0.8469(1)   | 0.0914(1)   | 0.0271(3) |
| O4   | −0.1314(1) | 0.6768(1)   | −0.0434(1)  | 0.0244(3) |
| O5   | 0.6440(1)  | 0.1687(1)   | 0.5282(1)   | 0.0229(3) |
| O6   | 0.6372(1)  | 0.3416(1)   | 0.6613(1)   | 0.0284(3) |
| O7   | 0.6315(1)  | 0.6009(1)   | 0.6624(1)   | 0.0274(3) |
| O8   | 0.6062(1)  | 0.7750(1)   | 0.5322(1)   | 0.0216(2) |
| O9   | 0.0000     | 0.0994(2)   | 0.2500      | 0.0194(3) |

TABLE 4C

Triethylenetetramine tetramaleate anisotropic displacement parameters (in Å²)

|     | $U_{11}$   | $U_{22}$   | $U_{33}$   | $U_{12}$    | $U_{13}$    | $U_{23}$    |
|-----|------------|------------|------------|-------------|-------------|-------------|
| C1  | 0.0167(7)  | 0.0198(7)  | 0.0163(7)  | −0.0006(5)  | 0.0003(5)   | −0.0013(6)  |
| C2  | 0.0273(8)  | 0.0216(8)  | 0.0137(7)  | 0.0024(6)   | 0.0007(6)   | 0.0011(6)   |
| C3  | 0.0256(7)  | 0.0218(8)  | 0.0148(7)  | 0.0007(6)   | −0.0002(5)  | −0.0028(6)  |
| C4  | 0.0196(7)  | 0.0205(8)  | 0.0208(7)  | −0.0001(6)  | −0.0005(5)  | 0.0005(6)   |
| C5  | 0.0185(7)  | 0.0190(7)  | 0.0160(7)  | −0.0017(5)  | 0.0015(5)   | −0.0011(6)  |
| C6  | 0.0250(8)  | 0.0193(7)  | 0.0118(7)  | −0.0002(6)  | 0.0015(5)   | 0.0019(5)   |
| C7  | 0.0246(7)  | 0.0209(8)  | 0.0118(6)  | 0.0005(6)   | 0.0014(5)   | −0.0013(6)  |
| C8  | 0.0185(7)  | 0.0186(7)  | 0.0168(7)  | −0.0009(5)  | 0.0001(5)   | 0.0005(5)   |
| C9  | 0.0185(7)  | 0.0170(7)  | 0.0163(7)  | 0.0009(5)   | 0.0004(5)   | −0.0003(5)  |
| C10 | 0.0195(7)  | 0.0178(7)  | 0.0162(7)  | 0.0010(5)   | −0.0001(5)  | −0.0007(6)  |
| C11 | 0.0198(7)  | 0.0218(8)  | 0.0124(6)  | 0.0002(6)   | 0.0020(5)   | −0.0010(6)  |
| N1  | 0.0194(6)  | 0.0141(6)  | 0.0137(6)  | −0.0006(4)  | 0.0010(5)   | 0.0000(5)   |
| N2  | 0.0218(6)  | 0.0191(6)  | 0.0164(6)  | 0.0003(5)   | −0.0015(5)  | −0.0022(5)  |
| O1  | 0.0285(6)  | 0.0170(5)  | 0.0204(5)  | 0.0014(4)   | −0.0032(4)  | −0.0013(4)  |
| O2  | 0.0364(6)  | 0.0211(6)  | 0.0142(5)  | 0.0007(5)   | −0.0028(4)  | −0.0007(4)  |
| O3  | 0.0353(6)  | 0.0182(6)  | 0.0278(6)  | −0.0019(5)  | −0.0026(5)  | −0.0006(5)  |
| O4  | 0.0355(6)  | 0.0201(6)  | 0.0176(5)  | −0.0018(4)  | −0.0022(4)  | 0.0025(4)   |
| O5  | 0.0322(6)  | 0.0173(5)  | 0.0193(5)  | −0.0001(4)  | 0.0007(4)   | 0.0011(4)   |
| O6  | 0.0511(7)  | 0.0216(6)  | 0.0125(5)  | 0.0005(5)   | −0.0017(5)  | 0.0006(4)   |
| O7  | 0.0479(7)  | 0.0203(6)  | 0.0137(5)  | 0.0006(5)   | −0.0035(5)  | −0.0016(4)  |
| O8  | 0.0283(6)  | 0.0168(5)  | 0.0198(5)  | −0.0004(4)  | 0.0020(4)   | −0.0018(4)  |
| O9  | 0.0219(7)  | 0.0177(7)  | 0.0186(7)  | 0.00000     | −0.0018(6)  | 0.00000     |

Example 21

Figure 20:
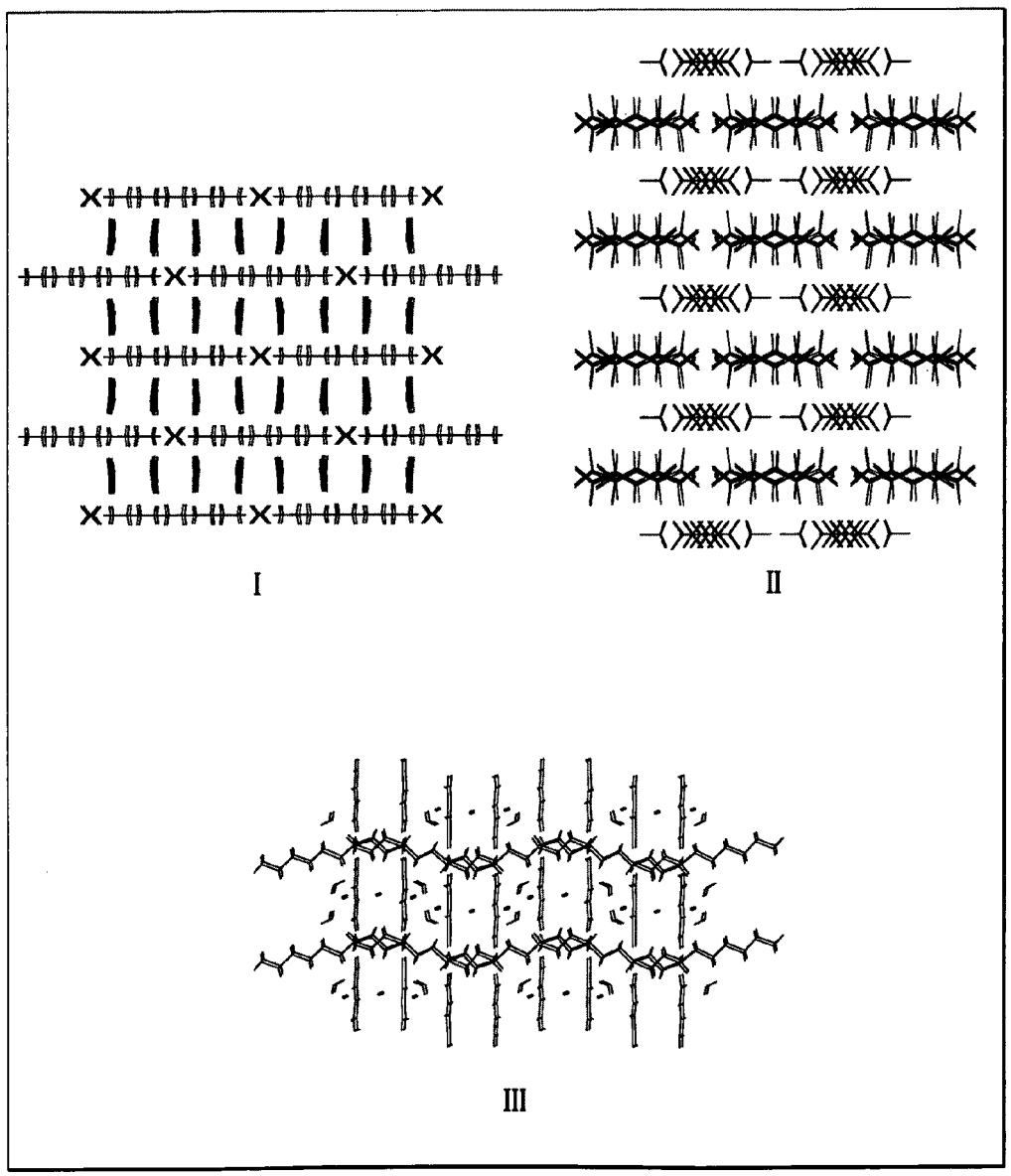
FIG. 20 shows 2×2×2 unit cells of triethylenetetramine tetrafumarate, with view along (I) [010], (II) [001] and (III) [100].
Figure 21:
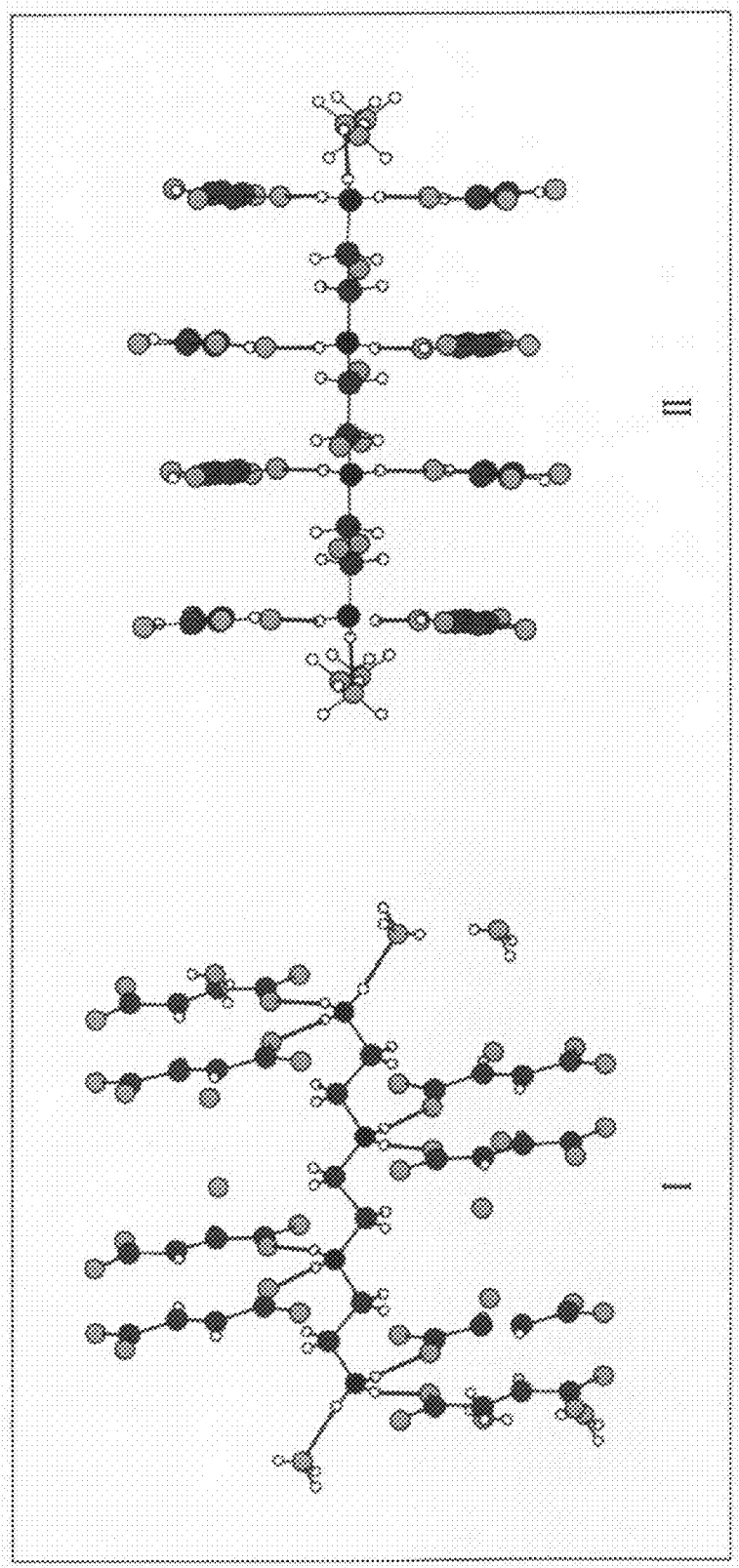
FIG. 21 shows a coordination sphere of triethylenetetramine with view along (I) [100] and (II) [010].
Figure 22:
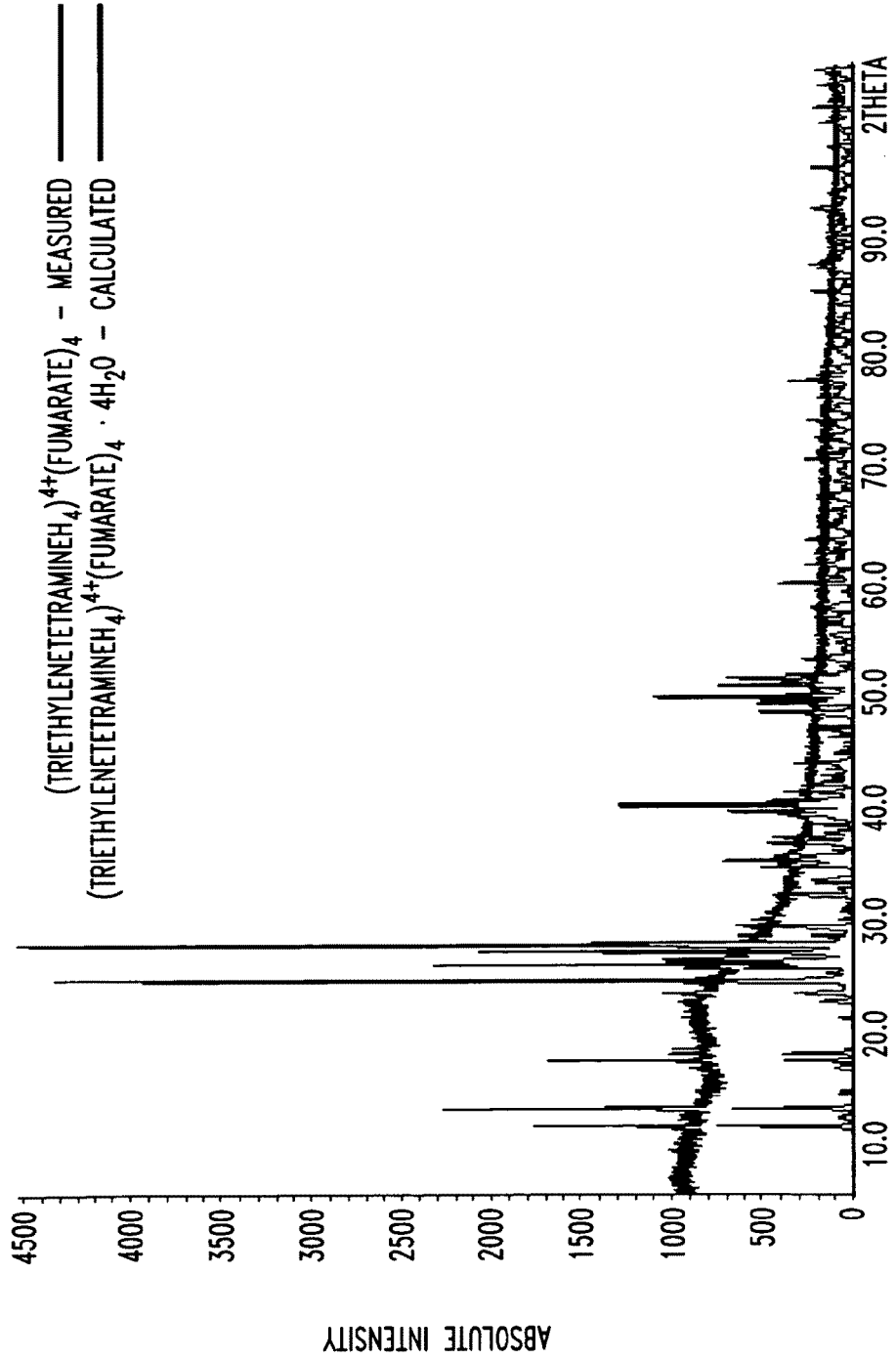
FIG. 22 shows an X-ray powder pattern of triethylenetetramine tetrafumarate powder material in comparison with the calculated powder pattern obtained from the single crystal structure data for triethylenetetramine tetrafumarate. $4H_2O$.

The crystal structure of the triethylenetetramine tetrafumarate is related to the structure of triethylenetetramine tetramaleate. The crystal structure data (FIG. 20) revealed a compound composition of triethylenetetramine tetrafumarate.4H$_2$O. Analysis of the structure confirmed the 1:4 ratio of triethylenetetramine:fumarate as four water molecules were found. The triethylenetetramine molecule interacts via strong hydrogen bonds between the H-atoms of the protonated NH— and NH$_2$-groups and the O-atoms of eight fumarate molecules, except for one H-atom of each NH$_3^+$-group at each end of the molecule which forms an additional bond to a water molecule. In this case, it appears that two water molecules may be necessary to complete the coordination sphere of the NH$_3^+$-groups of the triethylenetetramine molecule. See FIG. 21. Each fumarate molecule is connected to four different triethylenetetramine molecules via two short and two long hydrogen bonds. FIG. 20 shows that triethylenetetramine tetrafumarate forms a layered structure of triethylenetetramine and fumarate molecules. In contrast to triethylenetetramine tetramaleate, the triethylenetetramine layers of triethylenetetramine tetrafumarate are shifted along the c axis of c/2 against each other. Within the layers, the triethylenetetramine molecules are only connected to each other via the additional water molecules. The layers of triethylenetetramine and fumarate are also connected via hydrogen bonds. Within the fumarate layers, the molecules are arranged in pairs with alternating orientations and there are additional water molecules located between these molecules. There appears to be no significant interactions between the fumarate and the water molecules. In the case of triethylenetetramine tetrafumarate, a comparison of the powder pattern of triethylenetetramine tetrafumarate powder material with calculated data of the triethylenetetramine tetrafumarate.4H$_2$O crystal structure, which contains four additional water molecules, shows that there is a complete conformity of all reflexes between these two compounds. FIG. 22 represents an x-ray powder diffraction pattern obtained from a synthesized triethylenetetramine tetrafumarate. Crystal quality may be enhanced by an additional recrystallisation. A comparison with the analytical data shows that the compound is hygroscopic and the NMR, IR and DSC results also indicate that the compound contains water.

TABLE 5A

Crystallographic and refinement data for triethylenetetramine tetrafumarate tetrahydrate

| | |
|---|---|
| formula sum | C$_{44}$H$_{20}$N$_8$O$_{44}$ |
| formula weight | 1364.68 |
| measurement temperature | 84(2) K |
| measurement device | Bruker SMART CCD |
| wavelength | 0.71073 Å (Mo-K $\alpha$-radiation) |
| crystal system | orthorhombic |
| space group | P m n a (no. 53) |
| unit cell dimensions | a = 13.9031(3) Å |
| | b = 7.9589(2) Å |
| | c = 14.6554(3) Å |
| cell volume | 1621.67(6) Å$^3$ |
| Z | 1 |
| density, calculated | 1.397 g/cm$^3$ |
| R$_{All}$ | 0.075 |
| absorption coefficient $\mu$ | 0.130 mm$^{-1}$ |
| F(000) | 692 |
| $\theta$ range | 2.02-26.39° |
| h$_{min}$, h$_{max}$; k$_{min}$, k$_{max}$; l$_{min}$, l$_{max}$ | −17, 17; −8, 9; −18, 12 |
| reflections measured | 9146 [R(int) = 0.0573] |
| independent reflections | 1728 |
| observed reflections [I > 2s(i)] | 1541 |
| data/restraints/parameters | 1728/0/139 |
| Goodness-of-fit at F$^2$ | 1.187 |
| R indices [I > 2 sigma(I)] | R1 = 0.0678, wR2 = 0.1457 |
| R indices (all data) | R1 = 0.0754, wR2 = 0.1502 |
| largest diff. peak/hole | 0.455/−0.381 e · A$^{-3}$ |

TABLE 5B

Triethylenetetramine tetrafumarate atomic coordinates and isotropic displacement parameters (in Å$^2$)

| | x | y | z | U$_{eq}$ |
|---|---|---|---|---|
| N1 | 0 | 0.5928(3) | 0.1267(2) | 0.0252(6) |
| H1A | 0 | 0.67640 | 0.08640 | 0.0380 |
| H1B | −0.05230 | 0.52990 | 0.11880 | 0.0380 |
| H1C | 0.05230 | 0.52990 | 0.11880 | 0.0380 |
| N2 | 0 | 0.5907(3) | 0.3820(2) | 0.0232(6) |
| H2A | −0.05230 | 0.65600 | 0.38910 | 0.0280 |
| H2B | 0.05230 | 0.65600 | 0.38910 | 0.0280 |
| C1 | 0 | 0.6630(4) | 0.2203(2) | 0.0256(7) |
| H1D | −0.05650 | 0.73250 | 0.22920 | 0.0310 |
| H1E | 0.05650 | 0.73250 | 0.22920 | 0.0310 |
| C2 | 0 | 0.5204(4) | 0.2885(2) | 0.0242(7) |
| H2C | −0.05650 | 0.45090 | 0.27970 | 0.0290 |
| H2D | 0.05650 | 0.45090 | 0.27970 | 0.0290 |
| C3 | 0 | 0.4584(4) | 0.4541(3) | 0.0245(7) |
| H3A | 0.0559(19) | 0.393(3) | 0.4448(18) | 0.033(7) |
| C4 | 0.22620(16) | 0.3189(3) | 0.12220(19) | 0.0284(6) |
| C5 | 0.27015(17) | 0.1484(3) | 0.11941(18) | 0.0290(6) |
| H5A | 0.33670 | 0.14060 | 0.11490 | 0.0350 |
| C6 | 0.22071(16) | 0.0093(3) | 0.12297(18) | 0.0255(5) |
| H6A | 0.15410 | 0.01590 | 0.12780 | 0.0310 |
| C7 | 0.26664(16) | 0.8402(3) | 0.11968(18) | 0.0264(5) |
| O1 | 0.20734(12) | 0.7174(2) | 0.12499(15) | 0.0370(5) |
| H1F | 0.245(3) | 0.585(6) | 0.120(3) | 0.119(18) |
| O2 | 0.35426(12) | 0.8256(2) | 0.11207(17) | 0.0407(6) |
| O3 | 0.28558(12) | 0.4403(2) | 0.12399(16) | 0.0413(6) |
| O4 | 0.13799(13) | 0.3371(2) | 0.12186(17) | 0.0464(6) |
| O5 | 0 | 0.1729(4) | 0.0124(2) | 0.0322(6) |
| H5B | 0 | 0.095(10) | 0.004(7) | 0.14(4) |
| H5C | 0.053(4) | 0.209(6) | 0.052(3) | 0.022(13) |
| O6 | 0 | 1.0804(8) | 0.2523(9) | 0.134(6) |
| O7 | 0 | 1.0541(11) | 0.4360(14) | 0.143(10) |

TABLE 5C

Triethylenetetramine tetrafumarate anisotropic displacement parameters (in Å$^2$)

| | U$_{11}$ | U$_{22}$ | U$_{33}$ | U$_{12}$ | U$_{13}$ | U$_{23}$ |
|---|---|---|---|---|---|---|
| N1 | 0.0184(13) | 0.0167(13) | 0.0406(17) | 0.00000 | 0.00000 | −0.0023(12) |
| N2 | 0.0156(12) | 0.0107(12) | 0.0432(17) | 0.00000 | 0.00000 | 0.0006(12) |
| C1 | 0.0218(15) | 0.0148(14) | 0.0402(19) | 0.00000 | 0.00000 | −0.0030(14) |
| C2 | 0.0177(14) | 0.0127(14) | 0.042(2) | 0.00000 | 0.00000 | −0.0007(14) |
| C3 | 0.0199(15) | 0.0108(14) | 0.043(2) | 0.00000 | 0.00000 | 0.0002(14) |
| C4 | 0.0195(11) | 0.0147(10) | 0.0509(16) | 0.0006(9) | 0.0005(10) | −0.0024(10) |
| C5 | 0.0193(11) | 0.0146(11) | 0.0530(16) | 0.0024(8) | 0.0042(11) | −0.0002(11) |
| C6 | 0.0193(10) | 0.0150(11) | 0.0423(14) | 0.0013(9) | −0.0041(10) | 0.0013(10) |
| C7 | 0.0206(11) | 0.0139(10) | 0.0448(14) | 0.0005(8) | −0.0016(10) | 0.001(1) |
| O1 | 0.0189(8) | 0.0110(8) | 0.0812(15) | −0.0003(6) | 0.0009(9) | 0.0014(8) |
| O2 | 0.0189(9) | 0.0139(8) | 0.0894(16) | 0.0012(6) | 0.0012(9) | 0.0056(9) |
| O3 | 0.0204(9) | 0.0110(8) | 0.0925(17) | 0.0002(6) | 0.0010(9) | 0.0019(9) |
| O4 | 0.0207(9) | 0.0143(8) | 0.1042(18) | 0.0015(7) | 0.0032(10) | −0.0078(10) |
| O5 | 0.0287(13) | 0.0282(14) | 0.0395(16) | 0.00000 | 0.00000 | 0.0051(12) |
| O6 | 0.065(5) | 0.038(4) | 0.299(18) | 0.00000 | 0.00000 | −0.009(6) |
| O7 | 0.036(5) | 0.030(5) | 0.36(3) | 0.00000 | 0.00000 | −0.014(8) |

Patents, patent applications, publications, scientific articles, books, web sites, and other documents and materials referenced or mentioned herein are indicative of the levels of skill of those skilled in the art to which the inventions pertain. Each such referenced document and material is hereby incorporated by reference to the same extent as if it had been incorporated by reference in its entirety individually or set forth or reprinted herein in its entirety. Additionally, all claims in this application, and all priority applications, including but not limited to original claims, are hereby incorporated in their entirety into, and form a part of, the written description of the invention. Applicants reserve the right to physically incorporate into this specification any and all materials and information from any such patents, applications, publications, scientific articles, web sites, electronically available information, and other referenced materials or documents. Applicants reserve the right to physically incorporate into any part of this document, including any part of the written description, and the claims referred to above including but not limited to any original claims.

The inventions have been described broadly and generically herein. Each of the narrower species and subgeneric groupings falling within the generic disclosure also form part of these inventions. This includes the generic description of each invention which hereby include, including any claims thereto, a proviso or negative limitation removing or optionally allowing the removal of any subject matter from the genus, regardless of whether or not the excised materials or options were specifically recited or identified in haec verba herein, and all such variations form a part of the original written description of the inventions. In addition, where features or aspects of an invention are described in terms of a Markush group, the invention shall be understood thereby to be described in terms of each and every, and any, individual member or subgroup of members of the Markush group.

Although the invention has been described in terms of synthesis of triethylenetetramines and triethylenetetramine salts, it should be recognized that the routes, steps, and intermediates described in the disclosure are applicable to the synthesis of polyethylenepolyamines and polyethylenepolyamine salts of the formula $NH_2CH_2(CH_2NHCH_2CH_2NHCH_2)_nCH_2NH_2$ through synthesis, protection, and reduction as described herein of dinitrile intermediates of the general formula $NC(CH_2NHCH_2CH_2NHCH_2)_nCN$, where n is greater than or equal to 1.

The inventions illustratively described and claimed herein can suitably be practiced in the absence of any element or elements, limitation or limitations, not specifically disclosed herein or described herein as essential. Thus, for example, the terms "comprising," "including," "containing," "for example", etc., shall be read expansively and without limitation. The term "including" means "including but not limited to." The phrase "for example" is not limited to or by the items that follow the phrase. All references to things "known in the art" include all those things and equivalents and substitutes, whether now known or later discovered.

In claiming their inventions, the inventors reserve the right to substitute any transitional phrase with any other transitional phrase, and the inventions shall be understood to include such substituted transitions and form part of the original written description of the inventions. Thus, for example, the term "comprising" may be replaced with either of the transitional phrases "consisting essentially of" or "consisting of."

The methods and processes illustratively described herein may be suitably practiced in differing orders of steps. They are not necessarily restricted to the orders of steps indicated herein or in the claims.

As used herein and in the appended claims, the singular forms "a," "an," and "the" include plural reference unless the context clearly dictates otherwise.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement was specifically and without qualification or reservation expressly adopted by Applicants in a responsive writing specifically relating to the application that led to this patent prior to its issuance.

The terms and expressions employed herein have been used as terms of description and not of limitation, and there is no intention in the use of such terms and expressions, or any portions thereof, to exclude any equivalents now know or later developed, whether or not such equivalents are set forth or shown or described herein or whether or not such equivalents are viewed as predictable, but it is recognized that various modifications are within the scope of the invention claimed, whether or not those claims issued with or without alteration or amendment for any reason. Thus, it shall be understood that, although the present invention has been specifically disclosed by preferred embodiments and optional features, modifications and variations of the inventions embodied therein or herein disclosed can be resorted to by those skilled in the art, and such modifications and variations are considered to be within the scope of the inventions disclosed and claimed herein.

Specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. Where examples are given, the description shall be construed to include but not to be limited to only those examples. It will be readily apparent to one skilled in the art that varying substitutions and modifications may be made to the invention disclosed herein without departing from the scope and spirit of the invention, and from the description of the inventions, including those illustratively set forth herein, it is manifest that various modifications and equivalents can be used to implement the concepts of the present invention without departing from its scope. A person of ordinary skill in the art will recognize that changes can be made in form and detail without departing from the spirit and the scope of the invention. The described embodiments are to be considered in all respects as illustrative and not restrictive. Thus, for example, additional embodiments are within the scope of the invention and within the following claims.

The invention claimed is:

1. A polymorph of triethylenetetramine disuccinate, wherein said polymorph has a DSC extrapolated onset and peak melting temperatures of from between about 170° C. to about 190° C.

2. The polymorph of claim 1 wherein said DSC extrapolated onset and peak melting temperature are 180.05 and 179.91° C., respectively.

3. The polymorph of claim 1, wherein said polymorph has infrared peaks at wavenumbers at 3148, 1645, 1549, 1529, 1370, 1271, 1172, 1152, and 1033.

4. A Form I polymorph of triethylenetetramine dihydrochloride, wherein said Form I polymorph is characterized by a DSC extrapolated onset and peak melting temperatures of between about 111° C. to 132° C.

5. The Form I polymorph of claim 4 wherein said DSC extrapolated onset and peak melting temperatures are 121.96 and 122.78° C., respectively.

6. The Form I polymorph of claim 4, wherein said Form I polymorph is characterized by infrared peaks at wavenumbers 1043, 1116, 1300, 1328, 1557, 2833, 2895, 2902, and 3216.

7. A Form II polymorph of triethylenetetramine dihydrochloride, wherein said Form II polymorph is characterized by a DSC extrapolated onset and peak melting temperature of from between about 106° C. to about 126° C.

8. The Form II polymorph of claim 7 wherein said DSC extrapolated onset and peak melting temperatures are 116.16 and 116.76° C., respectively.

9. The Form II polymorph of claim 7, wherein said Form II polymorph is characterized by infrared peaks at wave numbers 1039, 1116, 1352, 1519, 2954, 2986, 3276, and 3298.

10. A pharmaceutical composition comprising substantially pure triethylenetetramine disuccinate of claim 1.

11. A pharmaceutical composition comprising substantially pure triethylenetetramine disuccinate of claim 1 and a pharmaceutically acceptable excipient.

12. A substantially pure triethylenetetramine disuccinate according to claim 1.

13. The polymorph of a triethylenetetramine disuccinate according to claim 1 wherein the polymorph is a crystal having the structure defined by the co-ordinates of Table 3B.

14. The polymorph of a triethylenetetramine disuccinate according to claim 1 wherein the polymorph is a crystal having the structure defined by the co-ordinates of Table 3C.

15. A crystalline form of triethylenetetramine disuccinate.

16. A polymorph according to claim 1 which exhibits an infrared spectrum substantially as depicted in FIG. 7.

17. A polymorph according to claim 1 which exhibits a DSC graph substantially as that depicted in FIG. 8.

18. The Form I polymorph according to claim 4 which exhibits an infrared spectrum substantially as depicted in FIG. 9.

19. The Form I polymorph according to claim 4 which exhibits a DSC graph substantially as that depicted in FIG. 10.

20. The Form II polymorph according to claim 7 which exhibits an infrared spectrum substantially as depicted in FIG. 11.

21. The Form II polymorph according to claim 7 which exhibits a DSC graph substantially that depicted in as FIG. 12.

22. The crystalline form of triethylenetetramine disuccinate according to claim 15 having the structure defined by the co-ordinates of Table 3B.

23. The crystalline form of triethylenetetramine disuccinate according to claim 15 having the structure defined by the co-ordinates of Table 3C.

24. The crystalline form of triethylenetetramine disuccinate according to claim 15 having a C 2/c (no. 15) space group with measured unit cell dimensions of a=14.059(5) Å, b=9,169(5) Å, c=13.647(5) Å, and β=92.47(0) Å.

25. The crystalline form of triethylenetetramine disuccinate according to claim 15 having the x-ray powder diffraction spectrum substantially as depicted in FIG. 16.

* * * * *